(12) United States Patent
Buckler et al.

(10) Patent No.: US 11,887,713 B2
(45) Date of Patent: Jan. 30, 2024

(54) NON-INVASIVE DETERMINATION OF LIKELY RESPONSE TO ANTI-DIABETIC THERAPIES FOR CARDIOVASCULAR DISEASE

(71) Applicant: Elucid Bioimaging Inc., Boston, MA (US)

(72) Inventors: Andrew J. Buckler, Boston, MA (US); Ulf Hedin, Ronninge (SE); Ljubica Matic, Solna (SE); Matthew Phillips, Boston, MA (US)

(73) Assignee: Elucid Bioimaging Inc., Boston, MA (US)

( * ) Notice: Subject to any disclaimer, the term of this patent is extended or adjusted under 35 U.S.C. 154(b) by 0 days.

(21) Appl. No.: 17/838,147

(22) Filed: Jun. 10, 2022

(65) Prior Publication Data

US 2023/0005583 A1    Jan. 5, 2023

Related U.S. Application Data

(63) Continuation-in-part of application No. 17/693,229, filed on Mar. 11, 2022.

(60) Provisional application No. 63/209,164, filed on Jun. 10, 2021.

(51) Int. Cl.
*G16H 20/10* (2018.01)
*G16B 5/00* (2019.01)

(52) U.S. Cl.
CPC ............. *G16H 20/10* (2018.01); *G16B 5/00* (2019.02)

(58) Field of Classification Search
CPC ........ G16H 10/00; G16H 10/40; G16H 15/00; G16H 20/00; G16H 20/10; G16H 20/13; G16H 20/17; G16H 30/00; G16H 40/00; G16H 50/00; G16H 70/00; G16H 80/00; G06Q 50/22–24; G16B 5/00
USPC .................................................. 705/2, 3, 20
See application file for complete search history.

(56) References Cited

U.S. PATENT DOCUMENTS

| | | |
|---|---|---|
| 6,245,016 B1 | 6/2001 | Daft et al. |
| 8,879,813 B1 | 11/2014 | Solanki et al. |
| 8,883,487 B2 | 11/2014 | Collier et al. |
| 9,235,887 B2 | 1/2016 | Buckler et al. |
| 9,761,048 B2 | 9/2017 | Igarashi |
| 9,858,529 B2 | 1/2018 | Adams et al. |

(Continued)

FOREIGN PATENT DOCUMENTS

| | | |
|---|---|---|
| WO | WO 2003/091391 | 11/2003 |
| WO | WO 2015/058151 | 4/2015 |

(Continued)

OTHER PUBLICATIONS

Wojcik, M. et al., "Molecular Mechanisms Underlying Curcumin-Mediated Therapeutic Effects in Type 2 Diabetes and Cancer," Oxid Med Cell Longev. Mar. 20, 2018;2018:9698258. doi: 10.1155/2018/9698258. PMID: 29743988; PMCID: PMC5884026.*

(Continued)

*Primary Examiner* — Robert W Morgan
*Assistant Examiner* — Charles P Coleman
(74) *Attorney, Agent, or Firm* — Fish & Richardson P.C.

(57) ABSTRACT

Provided herein are methods and systems for making patient-specific therapy recommendations of an anti-diabetic therapy for patients with known or suspected cardiovascular disease, such as atherosclerosis.

24 Claims, 39 Drawing Sheets
(28 of 39 Drawing Sheet(s) Filed in Color)

(56) References Cited

U.S. PATENT DOCUMENTS

| | | | |
|---|---|---|---|
| 10,176,408 | B2 | 1/2019 | Paik et al. |
| 10,740,880 | B2 | 8/2020 | Paik et al. |
| 10,755,810 | B2 | 8/2020 | Buckler et al. |
| 10,813,612 | B2 | 10/2020 | Min |
| 11,087,459 | B2 | 8/2021 | Buckler et al. |
| 11,087,460 | B2 | 8/2021 | Buckler et al. |
| 11,094,058 | B2 | 8/2021 | Buckler et al. |
| 11,113,812 | B2 | 9/2021 | Buckler et al. |
| 11,120,312 | B2 | 9/2021 | Buckler et al. |
| 11,257,584 | B2 | 2/2022 | Buckler et al. |
| 2005/0043614 | A1 | 2/2005 | Huizenga et al. |
| 2005/0118632 | A1 | 6/2005 | Chen et al. |
| 2005/0131663 | A1 | 6/2005 | Bangs et al. |
| 2006/0099148 | A1 | 5/2006 | Fisher et al. |
| 2007/0260141 | A1 | 11/2007 | Margolis et al. |
| 2008/0057590 | A1 | 3/2008 | Urdea et al. |
| 2009/0150134 | A1 | 6/2009 | De Leon et al. |
| 2009/0324126 | A1 | 12/2009 | Zitnick et al. |
| 2010/0063839 | A1 | 3/2010 | alSafadi |
| 2011/0026798 | A1 | 2/2011 | Madabhushi et al. |
| 2012/0232930 | A1 | 9/2012 | Schmidt et al. |
| 2012/0278060 | A1 | 11/2012 | Cancedda et al. |
| 2012/0329662 | A1 | 12/2012 | West et al. |
| 2014/0270440 | A1 | 9/2014 | Inglese et al. |
| 2014/0324460 | A1 | 10/2014 | Caffrey et al. |
| 2015/0272467 | A1 | 10/2015 | Warfield et al. |
| 2016/0042508 | A1 | 2/2016 | Novikov et al. |
| 2016/0097716 | A1 | 4/2016 | Gulati et al. |
| 2016/0310018 | A1 | 10/2016 | Fonte et al. |
| 2016/0314580 | A1 | 10/2016 | Lloyd et al. |
| 2016/0335412 | A1 | 11/2016 | Tucker et al. |
| 2017/0323078 | A1* | 11/2017 | Michon ............ G06Q 50/22 |
| 2017/0358079 | A1 | 12/2017 | Gillies et al. |
| 2018/0253591 | A1 | 9/2018 | Madabhushi et al. |
| 2018/0321347 | A1 | 11/2018 | Wang et al. |
| 2018/0330477 | A1 | 11/2018 | Paik et al. |
| 2018/0336319 | A1 | 11/2018 | Ito et al. |
| 2019/0019300 | A1 | 1/2019 | Simpson et al. |
| 2019/0244347 | A1 | 8/2019 | Buckler et al. |
| 2020/0227166 | A1 | 7/2020 | Rose et al. |
| 2020/0321096 | A1* | 10/2020 | Mould ............... G16H 50/20 |
| 2021/0104321 | A1 | 4/2021 | Lipsky et al. |
| 2021/0287763 | A1 | 9/2021 | Sharma |
| 2021/0298611 | A1 | 9/2021 | Stocker et al. |
| 2021/0390689 | A1 | 12/2021 | Buckler et al. |
| 2022/0157423 | A1 | 5/2022 | Nanji et al. |
| 2022/0400963 | A1 | 12/2022 | Buckler et al. |
| 2022/0406459 | A1 | 12/2022 | Buckler et al. |
| 2022/0409160 | A1 | 12/2022 | Buckler et al. |
| 2022/0415519 | A1 | 12/2022 | Buckler et al. |
| 2023/0005582 | A1 | 1/2023 | Buckler et al. |

FOREIGN PATENT DOCUMENTS

| | | |
|---|---|---|
| WO | WO 2015/095282 | 6/2015 |
| WO | WO 2021/237117 | 11/2021 |

OTHER PUBLICATIONS

Tiwari, P., "Recent Trends in Therapeutic Approaches for Diabetes Management: A Comprehensive Update," J Diabetes Res. 2015;2015:340838. doi: 10.1155/2015/340838. Epub Jul. 27, 2015. PMID: 26273667; PMCID: PMC4530263.*

[No Author Listed], "Taking personalized medicine to heart," Nature Medicine, Feb. 7, 2018, 4:113.

Abdelrahman et al., "Coronary Computed Tomography Angiography From Clinical Uses to Emerging Technologies: JACC State-of-the-Art Review," Journal of the American College of Cardiology, Sep. 2020, 76(10):1226-1243.

accessdata.fda.gov [online], "510(k) Premarket Notification: K183012," Oct. 31, 2018, retrieved on Jun. 28, 2022, retrieved from URL <https://www.accessdata.fda.gov/scripts/cdrh/cfdocs/cfpmn/pmn.cfm?ID=K183012>, 3 pages.

Adam et al., "Machine learning approaches to drug response prediction: challenges and recent progress," NPJ Precision Oncology, Jun. 15, 2020, 4(19):1-10.

Aday et al., "Antiinflammatory therapy in clinical care: the CANTOS trial and beyond," Frontiers in Cardiovascular Medicine, Jun. 5, 2018, 5:62, 6 pages.

Aghamiri et al., "Automated inference of Boolean models from molecular interaction maps using CaSQ," Bioinformatics, Aug. 15, 2020, 36(16):4473-82.

Alimohammadi et al., "Development of a Patient-Specific Multi-Scale Model to Understand Atherosclerosis and Calcification Locations: Comparison with In vivo Data in an Aortic Dissection," Frontiers in Physiology, Jun. 21, 2016, 7(238):1-15.

Altafini, "ODEs models in Systems Biology: Lecture 5 & 6," SISSA, Feb. 15, 2007, 27 pages.

Anlamlert et al., "Modeling fibrous cap formation in atherosclerotic plaque development: stability and oscillatory behavior," Advances in Difference Equations, Dec. 2017, 2017(1):1-5.

Auricchio et al., "Carotid artery stenting simulation: from patient-specific images to finite element analysis," Medical Engineering & Physics, Apr. 1, 2011, 33(3):281-9.

Barsky et al., "Cerebral: a Cytoscape plugin for layout of and interaction with biological networks using subcellular localization annotation," Bioinformatics, Apr. 15, 2007, 23(8):1040-2.

Bergmann et al., "COPASI and its applications in biotechnology," Journal of Biotechnology, Nov. 10, 2017, 261:215-220.

Bergstrom et al., "The Swedish CArdioPulmonary BioImage Study: objectives and design," Journal of Internal Medicine, Jun. 19, 2015, 278(6):645-659.

biospace.com [online], "HeartFlow Announces Positive Medical Coverage Decisions on Non-Invasive HeartFlow® FFRct Analysis from Anthem Blue Cross Blue Shield, Blue Shield of California and Blue Cross and Blue Shield of Alabama," Aug. 31, 2017, retrieved on Jun. 30, 2022, retrieved from URL <https://www.biospace.com/article/releases/heartflow-announces-positive-medical-coverage-decisions-on-non-invasive-heartflow-ffrct-analysis-from-b-anthem-blue-cross-blue-shield-blue-shield-of/>, 6 pages.

Briley-Saebo et al., "Imaging of oxidation-specific epitopes in atherosclerosis and macrophage-rich vulnerable plaques," Current Cardiovascular Imaging Reports, Feb. 2011, 4(1):4-16.

Brinjikji et al., "Contemporary carotid imaging: From degree of stenosis to plaque vulnerability," Journal of Neurosurgery, Jan. 2016, 124(1):27-42.

Büchel et al., "Path2Models: large-scale generation of computational models from biochemical pathway maps," BMC Systems Biology, Dec. 2013, 7(1):1-9.

Büchel et al., "Qualitative translation of relations from BioPAX to SBML qual. Bioinformatics," Oct. 15, 2012, 28(20):2648-53.

Buckler et al., "Quantitative Imaging Test Approval and Biomarker Qualification: Interrelated but Distinct Activities," Radiology, Jun. 2011, 259(3):875-884.

Buckler et al., "Virtual Transcriptomics: Noninvasive Phenotyping of Atherosclerosis by Decoding Plaque Biology From Computed Tomography Angiography Imaging," Arteriosclerosis, Thrombosis, and Vascular Biology, May 2021, 41(5):1738-1750.

Cappendijk et al., "Assessment of human atherosclerotic carotid plaque components with multisequence MR imaging: initial experience," Radiology-Radiological Society of North America, Feb. 1, 2005, 234(2), 15 pages.

Casarin et al., "A Computational Model-Based Framework to Plan Clinical Experiments—An Application to Vascular Adaptation Biology," International Conference on Computational Science—ICCS 2018, Jun. 2018, pp. 352-362.

Casarin et al., "A twofold usage of an agent-based model of vascular adaptation to design clinical experiments," Journal of Computational Science, Nov. 1, 2018, 29:59-69.

Casarin et al., "Single Gene Therapies to Improve the Longevity of Peripheral Bypasses: A Systems Biology-Multiscale Modelling Approach," EJVES Vascular Forum, Jan. 1, 2020, 48:53-4.

Castellano et al., "Texture analysis of medical images," Clinical Radiology, Dec. 1, 2004, 59(12):1061-9.

(56) References Cited

OTHER PUBLICATIONS celldesigner.org [online], "CellDesigner™: A Modeling tool of biochemical networks," Jan. 11, 2005, retrieved on Jun. 28, 2022, retrieved from URL <https://www.celldesigner.org/>, 3 pages.

Chan et al., "Variational image deblurring—a window into mathematical image processing," LectureNote Series, Institute for Mathematical Sciences, National University of Singapore, May 19, 2004, 5, 44 pages.

Chaouiya et al., "SBML qualitative models: a model representation format and infrastructure to foster interactions between qualitative modelling formalisms and tools," BMC Systems Biology, Dec. 2013, 7(1), 33 pages.

Chaouiya, "Net modelling of biological networks," Briefings in Bioinformatics, Jul. 1, 2007, 8(4):210-9.

Chappell et al., "Extensive Proliferation of a Subset of Differentiated, yet Plastic, Medial Vascular Smooth Muscle Cells Contributes to Neointimal Formation in Mouse Injury and Atherosclerosis Models," Circulation Research, Dec. 9, 2016; 119(12):1313-1323.

Chatzizisis et al., "Association of global and local low endothelial shear stress with high-risk plaque using intracoronary 3D optical coherence tomography: Introduction of 'shear stress score'," European Heart Journal Cardiovascular Imaging, Aug. 2017, 18(8):888-897.

Choi et al., "Multiscale image segmentation using wavelet-domain hidden Markov models," IEEE Transactions on Image Processing, Feb. 2001, 10(9):1309-1321.

Chrencik et al., "Quantitative assessment of carotid plaque morphology (geometry and tissue composition) using computed tomography angiography," Journal of Vascular Surgery, Sep. 2019, 70(3):858-868.

Corti et al., "Multiscale Computational Modeling of Vascular Adaptation: A Systems Biology Approach Using Agent-Based Models," Frontiers in Bioengineering and Biotechnology, Nov. 2021, 9(744560):1-27.

cytoscape.org [online], "Cytoscape," 2001, retrieved on Jun. 29, 2022, retrieved from URL <https://cytoscape.org/>, 15 pages.

Davies et al., "Radionuclide Imaging for the Detection of Inflammation in Vulnerable Plaques," Journal of the American College of Cardiology, Apr. 2006, 47(8, Supplement):C57-C68.

DeMarco et al., "Imaging of high-risk carotid artery plaques: current status and future directions," Neurosurgical Focus, Jan. 2014, 36(1): E1.

Diaz-Zamudio et al., "Automated Quantitative Plaque Burden from Coronary CT Angiography Noninvasively Predicts Hemodynamic Significance by Using Fractional Flow Reserve in Intermediate Coronary Lesions," Radiology, Aug. 2015, 276(2):408-415.

Douglas et al., "1-Year Outcomes of FFRCT-Guided Care in Patients With Suspected Coronary Disease: The Platform Study," Journal of the American College of Cardiology, Aug. 2016, 68(5):435-445.

Douglas et al., "Outcomes of Anatomical versus Functional Testing for Coronary Artery Disease," New England Journal of Medicine, Apr. 2, 2015, 372(14):1291-1300.

Dougoud et al., "Prognostic value of coronary CT angiography on long-term follow-up of 6.9 years," The International Journal of Cardiovascular Imaging, Apr. 8, 2014, 30:969-976.

Du et al., "A decision analysis model for KEGG pathway analysis," BMC Bioinformatics, Oct. 6, 2016, 17:407, 12 pages.

Eungdamrong et al., "Modeling Cell Signaling Networks," Biology of the Cell, Jun. 2004, 96(5):355-362.

evicore.com [online], "Clinical Guidelines: Cardiac Imaging Policy," May 17, 2018, retrieved on Jun. 30, 2022, retrieved from URL <https://www.evicore.com/-/media/files/evicore/clinical-guidelines/solution/cardiology-and-radiology/archive/2018-bcbs-al-cardiac.pdf>, 65 pages.

Funahashi et al., "CellDesigner 3.5: A Versatile Modeling Tool for Biochemical Networks," Proceedings of the IEEE, Jul. 16, 2008, 96(8):1254-1265.

Genkel et al., "Conceptualization of Heterogeneity of Chronic Diseases and Atherosclerosis as a Pathway to Precision Medicine: Endophenotype, Endotype, and Residual Cardiovascular Risk," International Journal of Chronic Diseases, Feb. 12, 2020, Article 5950813, 9 pages.

genome.jp [online], "KEGG Lipid and atherosclerosis—Reference pathway," May 17, 2021, retrieved on Jun. 28, 2022, retrieved from URL <https://www.genome.jp/pathway/map05417+C02530>, 2 pages.

Ghazalpour et al., "Thematic review series: The Pathogenesis of Atherosclerosis. Toward a biological network for atherosclerosis," Journal of Lipid Research, Oct. 2004, 45(10):1793-1805.

Glass et al., "The logical analysis of continuous, non-linear biochemical control networks," Journal of Theoretical Biology, Apr. 1973, 39(1):103-129.

Golriz Khatami et al. "Using predictive machine learning models for drug response simulation by calibrating patient-specific pathway signatures," npj Systems Biology and Applications, Oct. 27, 2021, 7:1-9.

Gomez-Cabrero et al., "Workflow for generating competing hypothesis from models with parameter uncertainty," Interface Focus, Mar. 30, 2011, 1(3):438-449.

Helmlinger et al., "Quantitative Systems Pharmacology: An Exemplar Model-Building Workflow With Applications in Cardiovascular, Metabolic, and Oncology Drug Development," CPT: Pharmacometrics & Systems Pharmacology, Jun. 2019, 8(6):380-395.

Hoffmann et al., "Prognostic Value of Noninvasive Cardiovascular Testing in Patients With Stable Chest Pain: Insights From the PROMISE Trial (Prospective Multicenter Imaging Study for Evaluation of Chest Pain)," Circulation, Jun. 13, 2017, 135(24):2320-2332.

Holzapfel, "Chapter 10: Biomechanics of soft tissue," The Handbook of Materials Behavior Models, vol. 3, Multiphysics Behaviors, Composite Media ed., 2001, pp. 1049-1063.

Hucka et al., "The systems biology markup language (SBML): a medium for representation and exchange of biochemical network models," Bioinformatics, Mar. 2003, 19(4):524-531.

Ibrahimi et al., "Coronary and carotid atherosclerosis: How useful is the imaging?," Atherosclerosis, Dec. 2013, 231(2):323-333.

Invitation to Pay Additional Fees and, Where Applicable, Protest Fee in International Appln. No. PCT/US2022/020068, dated Jun. 24, 2022, 2 pages.

Johnson et al., "Is Discordance of Coronary Flow Reserve and Fractional Flow Reserve Due to Methodology or Clinically Relevant Coronary Pathophysiology?," JACC: Cardiovascular Imaging, Feb. 2012, 5(2):193-202.

Joshi et al., "Non-invasive imaging of atherosclerosis," European Heart Journal: Cardiovascular Imaging, Mar. 2012, 13(3):205-218.

Kaazempur-Mofrad et al., "Characterization of the Atherosclerotic Carotid Bifurcation Using MRI, Finite Element Modeling, and Histology," Annals of Biomedical Engineering, Jul. 2004, 32(7):932-946.

Kanehisa et al., "KEGG: integrating viruses and cellular organisms," Nucleic Acids Research, Jan. 8, 2021, 49(D1):D545-D551.

Kanehisa et al., "KEGG: Kyoto Encyclopedia of Genes and Genomes," Nucleic Acids Research, Jan. 2000, 28(1):27-30.

Karlof et al., "Correlation of computed tomography with carotid plaque transcriptomes associates calcification with lesion-stabilization," Atherosclerosis, Sep. 2019, 288:175-185.

Kawahara et al., "The detection of carotid plaque rupture caused by intraplaque hemorrhage by serial high-resolution magnetic resonance imaging: a case report," Surgical Neurology, Dec. 2008, 70(6):634-639.

Keating et al., "SBML Level 3: an extensible format for the exchange and reuse of biological models," Molecular Systems Biology, Aug. 2020, 16(8):e9110, 21 pages.

Khan et al., "Robust Atlas-Based Brain Segmentation Using Multi-structure Confidence-Weighted Registration" Proceedings of the 12th International Conference on Medical Image Computing, Sep. 20, 2009, pp. 549-557.

Khatami et al., "Using predictive machine learning models for drug response simulation by calibrating patient-specific pathway signatures," npj Systems Biology and Applications, Oct. 27, 2021, 7(40):1-9.

(56) References Cited

OTHER PUBLICATIONS

King et al., "Pathway analysis of coronary atherosclerosis," Physiological Genomics, Sep. 21, 2005, 23(1):103-118.

Koplay et al., "Comparison Between Prospectively Electrocardiogram-Gated High-Pitch Mode and Retrospectively Electrocardiogram-Gated Mode for Dual-Source CT Coronary Angiography," Polish Journal of Radiology, Dec. 2015, 80:561-568.

Lambin et al., "Radiomics: the bridge between medical imaging and personalized medicine," Nature Reviews Clinical Oncology, 2017, 14(12):749-762.

Langley et al., "Extracellular matrix proteomics identifies molecular signature of symptomatic carotid plaques," The Journal of Clinical Investigation, Mar. 2017, 127(4):1546-1560.

Lee et al., "Radiomics and imaging genomics in precision medicine," Precision and Future Medicine, Mar. 31, 2017, 1(1):10-31.

Leipsic, "Acquisition and Reconstruction Techniques for Coronary CT Angiography: GE Healthcare Scanner Platforms," HeartFlow, Aug. 24, 2018, 18 pages.

Lu et al., "Finite element analysis of mechanics of neovessels with intraplaque hemorrhage in carotid atherosclerosis," BioMedical Engineering Online, Jan. 9, 2015, 14(Suppl 1):53, 11 pages.

maayanlab.cloud [online], "Impute Data", Sep. 4, 2020, retrieved on Jun. 29, 2022, retrieved from URL <amp.pharm.mssm.edu/Enrichr>, 1 page.

Macklin, "Key challenges facing data-driven multicellular systems biology," GigaScience, 2019, 8:1-8.

MacRae et al., "Reimagining What We Measure in Atherosclerosis—a "Phenotype Stack"," Circulation Research, Apr. 24, 2020, 126(9):1146-1158.

Martin et al., "Analysis of haemodynamic factors involved in carotid atherosclerosis using computational fluid dynamics," The British Journal of Radiology, Jan. 2009, 82(special_issue_1):S33-S38.

Matic et al., "Novel Multiomics Profiling of Human Carotid Atherosclerotic Plaques and Plasma Reveals Biliverdin Reductase B as a Marker of Intraplaque Hemorrhage," JACC: Basic to Translational Science, Aug. 2018, 3(4):464-480.

Monir et al., "Finite element modelling of the common carotid artery in the elderly with physiological intimal thickening using layer-specific stress-released geometries and nonlinear elastic properties," Computer Methods in Biomechanics and Biomedical Engineering, 2016, 19(12):1286-1296.

Morgan et al., "Mathematically Modelling the Dynamics of Cholesterol Metabolism and Ageing," Biosystems, 2016, 145:19-32.

Muntendam et al., "The BioImage Study: Novel approaches to risk assessment in the primary prevention of atherosclerotic cardiovascular disease—study design and objectives," American Heart Journal, Jul. 2010, 160(1):59-57.e1.

Newby et al., "Coronary CT Angiography and 5-Year Risk of Myocardial Infarction," The New England Journal of Medicine, 2018. 379(10):924-933.

Nguyen et al., "Identifying significantly impacted pathways: a comprehensive review and assessment," Genome Biology, Oct. 2019, 20(203):1-15.

Okuda et al., "KEGG Atlas mapping for global analysis of metabolic pathways," Nucleic Acids Research, Jul. 2008, 36(suppl 2):W423-426.

Olgac et al., "Patient-specific three-dimensional simulation of LDL accumulation in a human left coronary artery in its healthy and atherosclerotic states," American Journal of Physiology: Heart and Circulatory Physiology, Jun. 2009, 296(6):H1969-H1982.

Orre et al., "SubCellBarCode: Proteome-wide Mapping of Protein Localization and Relocalization," Molecular Cell, Jan. 3, 2019, 73(1):166-182.e167.

Pai et al., "netDx: interpretable patient classification using integrated patient similarity networks," Molecular Systems Biology, Mar. 2019, 15(3):e8497.

Parton et al., "New models of atherosclerosis and multi-drug therapeutic interventions," Bioinformatics, Jul. 2019, 35(14):2449-2457.

Parvu et al., "A Novel Method to Verify Multilevel Computational Models of Biological Systems Using Multiscale Spatio-Temporal Meta Model Checking," PloS One, May 2016, 11:e0154847, 43 pages.

Perisic et al., "Gene expression signatures, pathways and networks in carotid atherosclerosis," Journal of Internal Medicine, Mar. 2016, 279(3):293-308.

Peyvandipour et al., "A novel computational approach for drug repurposing using systems biology," Bioinformatics, Aug. 2018, 34(16):2817-2825.

Puchner et al., "High-Risk Plaque Detected on Coronary CT Angiography Predicts Acute Coronary Syndromes Independent of Significant Stenosis in Acute Chest Pain: Results From the ROMICAT-II Trial," Journal of the American College of Cardiology, Aug. 2014, 64(7):684-692.

Rafailidis et al., "Carotid plaque vulnerability: the correlation of plaque components as quantified based on Computed Tomography Angiography with neurologic symptoms," European Congress of Radiology, 2019, Poster No. C-0161, 19 pages.

Ramsey et al., "A systems biology approach to understanding atherosclerosis," EMBO Molecular Medicine, Mar. 2010, 2(3):79-89.

Reda et al., "Machine learning applications in drug development," Computational and Structural Biotechnology Journal, 2020, 18:241-252.

Rodriguez-Granillo et al., "Defining the non-vulnerable and vulnerable patients with computed tomography coronary angiography: evaluation of atherosclerotic plaque burden and composition," European Heart Journal—Cardiovascular Imaging, May 2016, 17(5):481-491.

Rudin, "Stop explaining black box machine learning models for high stakes decisions and use interpretable models instead," Nature Machine Intelligence, May 13, 2019, 1:206-215.

Saam et al., "Prevalence of American Heart Association Type VI Carotid Atherosclerotic Lesions Identified by Magnetic Resonance Imaging for Different Levels of Stenosis as Measured by Duplex Ultrasound," Journal of the American College of Cardiology, Mar. 2008, 51(10):1014-1021.

Saam et al., "The Vulnerable, or High-Risk, Atherosclerotic Plaque: Noninvasive MR Imaging for Characterization and Assessment," Radiology, 2007, 244(1):64-77.

Saba et al., "Imaging biomarkers of vulnerable carotid plaques for stroke risk prediction and their potential clinical implications," The Lancet Neurology, Jun. 2019, 18(6):559-572.

Sanak et al., "The role of magnetic resonance imaging for acute ischemic stroke," Biomed Pap Med Fac Univ Palacky Olomouc Czech Repub, 2009, 153(3):181-187.

Sawada et al., "From unbiased transcriptomics to understanding the molecular basis of atherosclerosis," Current Opinion in Lipidology, Oct. 2021, 32(5):328-329.

Shalhoub et al., "Systems Biology of Human Atherosclerosis," Vascular and Endovascular Surgery, 2014, 48(1):5-17.

Shen et al. "Variational PDE Models in Image Processing" Notices of the AMS, 2003, 50(1):14-26.

Simmons et al., "Omics-based approaches in understanding mechanosensitive endothelial biology and atherosclerosis," Wiley Interdiscip Rev Syst Biol Med, Sep. 2016, 8(5):378-401.

Smith et al. "Standard machine learning approaches outperform deep representation learning on phenotype prediction from transcriptomics data," BMC Bioinformatics, Mar. 20, 2020, 21:1-18.

Sorger et al., "Quantitative and Systems Pharmacology in the Post-genomic Era: New Approaches to Discovering Drugs and Understanding Therapeutic Mechanisms," QSP White Paper, Oct. 2011, 48 pages.

Sousa et al., "Computational simulation of carotid stenosis and flow dynamics based on patient ultrasound data—A new tool for risk assessment and surgical planning," Advances in Medical Sciences, Mar. 2016, 61(1):32-39.

Taylor et al., "Computational Fluid Dynamics Applied to Cardiac Computed Tomography for Noninvasive Quantification of Fractional Flow Reserve: Scientific Basis," Journal of the American College of Cardiology, Jun. 2013, 61(22):2233-2241.

(56) References Cited

OTHER PUBLICATIONS

Tedgui et al., "Cytokines in Atherosclerosis: Pathogenic and Regulatory Pathways," Physiological Reviews, Apr. 2006, 86(2):515-581.
Ten Kate et al., "Noninvasive Imaging of the Vulnerable Atherosclerotic Plaque," Current Problems in Cardiology, Nov. 2010, 35(11):556-591.
Tesche et al., "Prognostic implications of coronary CT angiography-derived quantitative markers for the prediction of major adverse cardiac events," Journal of Cardiovascular Computed Tomography, Nov.-Dec. 2016, 10(6):458-465.
Thomas, "Boolean formalization of genetic control circuits," Journal of Theoretical Biology, Dec. 1973, 42(3):563-585.
Tian et al., "Integrating proteomic or transcriptomic data into metabolic models using linear bound flux balance analysis," Bioinformatics, Nov. 15, 2018, 34(22):3882-3888.
Tonino et al., "Angiographic Versus Functional Severity of Coronary Artery Stenoses in the FAME Study: Fractional Flow Reserve Versus Angiography in Multivessel Evaluation," Journal of the American College of Cardiology, Jun. 2010, 55(25):2816-2821.
Underhill et al., "A Noninvasive Imaging Approach to Assess Plaque Severity: The Carotid Atherosclerosis Score," American Journal of Neuroradiology, Jun. 2010, 31(6):1068-1075.
Van Assen et al., "Automated plaque analysis for the prognostication of major adverse cardiac events," European Society of Cardiology, Jul. 2019, 116:76-83.
Wang et al., "Computer-Aided Image Analysis Algorithm to Enhance In Vivo Diagnosis of Plaque Erosion by Intravascular Optical Coherence Tomography," Circulation: Cardiovascular Imaging, Sep. 2014, 7(5):805-810.
Watanabe et al., "MR plaque imaging of the carotid artery," Neuroradiology, Feb. 13, 2010, 52(4):253-274.
Watterson et al., "Logic models of pathway biology," Drug Discovery Today, May 2008, 13(9-10):447-456.
Wrzodek et al., "Precise generation of systems biology models from KEGG pathways," BMC Systems Biology, Feb. 21, 2013, 7:15, 12 pages.
Yoon et al., "Noninvasive Diagnosis of Ischemia-Causing Coronary Stenosis Using CT Angiography: Diagnostic Value of Transluminal Attenuation Gradient and Fractional Flow Reserve Computed From Coronary CT Angiography Compared to Invasively Measured Fractional Flow Reserve," JACC: Cardiovascular Imaging, Nov. 2012, 5(11): 1088-1096.
Yuan et al., "Carotid Atherosclerotic Plaque: Noninvasive MR Characterization and Identification of Vulnerable Lesions," Radiology, Nov. 2001, 221(2):285-299.
Zhu et al., "Semiautomated Characterization of Carotid Artery Plaque Features From Computed Tomography Angiography to Predict Atherosclerotic Cardiovascular Disease Risk Score," J Comput Assist Tomogr., May-Jun. 2019, 43(3):452-459.
PCT International Search Report and Written Opinion in International Appln. No. PCT/US2022/033115, dated Aug. 25, 2022, 14 pages.
PCT International Search Report and Written Opinion in International Appin. No. PCT/US2022/020068, dated Aug. 30, 2022, 14 pages.
Libby, "Targeting Inflammatory Pathway in Cardiovascular Disease: The Inflammasome, Interleukin-1, Interleukin-6 and Beyond," Cells, Apr. 20, 2021, 10(4):951, 21 pages.
U.S. Appl. No. 17/693,229, filed Mar. 11, 2022, Buckler et al.
Gadkar et al., "A Mechanistic Systems Pharmacology Model for Prediction of LDL Cholesterol Lowering by PCSK9 Antagonism in Human Dyslipidemic Populations," CPT: Pharmacometrics & Systems Pharmacology, Nov. 2014, 3(11):1-9.
Infante et al., "Evidence of association of circulating epigenetic-sensitive biomarkers with suspected coronary heart disease evaluated by Cardiac Computed Tomography," PLoS One, Jan. 2019, 14(1):1-17.
International Preliminary Report on Patentability in International Appln. No. PCT/US2022/033115, dated May 8, 2023, 8 pages.
Pichardo-Almarza et al., "From PK/PD to QSP: Understanding the Dynamic Effect of Cholesterol-Lowering Drugs on Atherosclerosis Progression and Stratified Medicine," Current Pharmaceutical Design, Dec. 2016, 22(46):6903-6910.
Van Stee et al., "Actions of Metformin and Statins on Lipid and Glucose Metabolism and Possible Benefit of Combination Therapy," Cardiovascular Diabetology, Dec. 2018, 17(1):1-22.
Benson et al., "Is systems pharmacology ready to impact upon therapy development? A study on the cholesterol biosynthesis pathway," British Journal of Pharmacology, Sep. 2017, 174(23):4362-4382.
Chang et al., "Dyslipidemia management update," Current Opinion in Pharmacology, Apr. 2017, 33:47-55.
Office Action in U.S. Appl. No. 17/838,129, dated Jun. 28, 2023, 20 pages.
Office Action in U.S. Appl. No. 17/838,129, dated Mar. 6, 2023, 16 pages.
Office Action in U.S. Appl. No. 17/838,140, dated Feb. 2, 2023, 7 pages.
Office Action in U.S. Appl. No. 17/838,146, dated Feb. 14, 2023, 10 pages.
Office Action in U.S. Appl. No. 17/838,146, dated Sep. 20, 2022, 14 pages.
Office Action in U.S. Appl. No. 17/838,148, dated Mar. 9, 2023, 19 pages.
Office Action in U.S. Appl. No. 18/115,924, dated Sep. 19, 2023, 18 pages.

* cited by examiner

NON-INVASIVE DETERMINATION OF LIKELY RESPONSE TO ANTI-DIABETIC THERAPIES FOR CARDIOVASCULAR DISEASE

CLAIM OF PRIORITY

This application claims the benefit of U.S. Provisional Application Ser. No. 63/209,164, filed on Jun. 10, 2021 and U.S. patent application Ser. No. 17/693,229, filed on Mar. 11, 2022. The entire contents of the foregoing are incorporated herein by reference.

TECHNICAL FIELD

This disclosure relates to methods and systems for making patient-specific therapy recommendations for patients with known or suspected cardiovascular disease, such as atherosclerosis.

BACKGROUND

Myocardial infarction (MI) and ischemic stroke (IS), major consequences of unstable atherosclerotic lesions, are the most common causes of death worldwide worldwide (World Health Organization (WHO). Cardiovascular diseases (CVDs) Fact Sheet, 2017, 23 Apr. 2020; available online at who.int/en/news-room/fact-sheets/detail/cardiovascular-diseases-(cvds)). Guidance for prevention of MI and IS is currently based on treatment efficacy at the group level.

According to the World Health Organization (WHO), cardiovascular disease (CVD), encompassing, coronary, and lower extremity artery disease, is the leading cause of death and disability globally (*The Atlas of Heart Disease and Stroke*, W.H. Organization, Editor, 2014), mainly by myocardial infarction and ischemic stroke from unstable atherosclerosis worldwide (World Health Organization (WHO). *Cardiovascular diseases (CVDs) Fact Sheet*, 2017, 23 Apr. 2020; Available from: www.who.int/en/news-room/fact-sheets/detail/cardiovascular-diseases-(cvds)). New treatments have been revolutionary over the last 30 years, yet CVD still exerts an exorbitantly high financial costs (Bloom et al., *The Global Economic Burden of Noncommunicable Diseases*, W.E. Forum, Editor. 2011: Geneva), with a $320 billion annual burden on the U.S. economy alone (Mozaffarian et al., *Heart Disease and Stroke Statistics*-2015 *Update: A Report from the American Heart Association*. Circulation, 2015. 131(4): p. e29). This is exacerbated by aging and changing ethnic mix (Gierada et al., *Projected outcomes using different nodule sizes to define a positive CT lung cancer screening examination*. Journal of the National Cancer Institute, 2014. 106(11): p. dju284; Warner, J. *Stroke Costs Reaching Trillions: Without Action, Financial Costs of Strokes to Reach* $2.2 *Trillion by* 2050. Stroke Health Center 2006 (cited 2014 Nov. 14, 2014); Available from: www.webmd.com/stroke/news/20060816/stroke-costs-reaching-trillions), as well as affecting an increasing proportion of people globally as economic development continues to narrow the gap between the developed and developing word populations.

In the U.S., the American Heart Association (AHA) projects that over 9% of adults are at significant (more than 20%) risk of adverse events within 10 years and over 25% more are at a moderate risk (Association, A.H., *AHA STATISTICAL UPDATE Heart Disease and Stroke Statistics—2018 Update*. Circulation Journal, 2018. 137). This yields 23 million high risk patients and 57 million moderate risk people. Of these, approximately 30 million people in the U.S. are currently on statin therapy in an attempt to avoid new or recurrent CV events, and the 16.5 million with a current CVD diagnosis are almost all on maintenance medications (Ross, G., *Too Few Americans Take Statins, CDC Study Reveals*. American Council on Science and Health, 2015; Vishwanath, R. and L. C. Hemphill, *Familial hypercholesterolemia and estimation of US patients eligible for low-density lipoprotein apheresis after maximally tolerated lipid-lowering therapy*. Journal of Clinical Lipidology, 2014. 8: p. 18-28; Herper, M. *How Many People Take Cholesterol Drugs?* Forbes, 2008; Pearson et al., *Markers of Inflammation and Cardiovascular Disease: Application to Clinical and Public Health Practice: A Statement for Healthcare Professionals From the Centers for Disease Control and Prevention and the American Heart Association*. Circulation, 2003. 107(3): p. 499-511).

According to the WHO, stroke accounts for 10% of all deaths across the globe, causing at least 5.5 million deaths annually (*The Atlas of Heart Disease and Stroke*, W.H. Organization, Editor. 2014). Of the approximately 800,000 annual strokes in the U.S., 87% are ischemic, and approximately 15% of all strokes are heralded by a transient ischemic attack (TIA) (Writing Group, M., D. Mozaffarian et al., *Heart Disease and Stroke Statistics*-2016 *Update: A Report From the American Heart Association*. Circulation, 2016. 133(4): p. e38-360; Bruce Ovbiagele, *Stroke Epidemiology: Advancing Our Understanding of Disease Mechanism and Therapy*. Neurotherapeutics, 2011. 2011(8): p. 319-329). Many ischemic stroke events are caused by atherosclerosis (Barrett et al., *Stroke Caused by Extracranial Disease*. Circ Res, 2017. 120(3): p. 496-501). 2.3 million subjects in the US are believed to have clinically significant stenosis (>50%), 19% of which have over 70% stenosis (de Weerd et al., *Prevalence of Asymptomatic Carotid Artery Stenosis in the General Population: An Individual Participant Data Meta-Analysis*. Stroke, 2010. 41(6): p. 1294-1297). Stroke also results in enormous costs for society, accounting for $36.5 (Go et al., *Heart Disease and Stroke Statistics* 2014 *Update: A Report From the American Heart Association*. Circulation, 2014. 129(3): p. e28-e292) to $74 billion annually (D. L. Brown et a., *Projected costs of ischemic stroke in the United States*. Neurology, 2006), estimated to reach $2.2 trillion by 2050 (PTINR.com-Staff $2.2 *trillion stroke cost projected.* 2006; Brown et al., *Projected costs of ischemic stroke in the United States*. Neurology, 2006. 67(8): p. 1390-1395).

According to the WHO, "coronary heart disease is now the leading cause of death worldwide. It is on the rise and has become a true pandemic that respects no borders" (*The Atlas of Heart Disease and Stroke*, W.H. Organization, Editor. 2014). Of the approximately 1.2 million annual coronary attacks in the U.S., ~66,000 are new, ~305,000 are recurrent, and ~160,000 are silent myocardial infarctions (MIs) (Writing Group, Mozaffarian et al., *Heart Disease and Stroke Statistics*-2016 *Update: A Report From the American Heart Association*. Circulation, 2016. 133(4): p. e38-360; Bruce Ovbiagele, *Stroke Epidemiology: Advancing Our Understanding of Disease Mechanism and Therapy*. Neurotherapeutics, 2011. 2011(8): p. 319-329. Coronary heart disease caused by atherosclerosis is the most common type of heart disease, killing 365,914 people in 2017 (Benjamin et al., *Heart Disease and Stroke Statistics*-2019 *Update: A Report From the American Heart Association*. Circulation, 2019. 139(10): p. e56-e528).

The relative risk levels for varying degrees of obstruction remains equivocal, with some reports seeming to support the notion that clinically non-obstructive coronary artery disease (CAD) actually harbors more high-risk plaque than more occlusive plaques, where others suggest that the stenotic plaques do have higher event rates (Chang et al., *Coronary Atherosclerotic Precursors of Acute Coronary Syndromes*. JOURNAL OF THE AMERICAN COLLEGE OF CARDIOLOGY (JACC), 2018. 71(22); Gaston A. Rodriguez-Granillo et al., *Defining the non-vulnerable and vulnerable patients with computed tomography coronary angiography: evaluation of atherosclerotic plaque burden and composition*. European Heart Journal— Cardiovascular Imaging, 2016. 2016(17): p. 481-491; Ahmadi et al., *Do plaques rapidly progress prior to myocardial infarction? The interplay between plaque vulnerability and progression*. Circulation research, 2015. 117(1): p. 99-104; Bittencourt et al., *Prognostic Value of Nonobstructive and Obstructive Coronary Artery Disease Detected by Coronary Computed Tomography Angiography to Identify Cardiovascular Events*. Circulation: Cardiovascular Imaging, 2014. 7(2): p. 282-291; Virmani et al., *Pathology of the Vulnerable Plaque*. JACC, 2006. 47(8): p. C13-8; F D Kolodgie et al., *Pathologic assessment of the vulnerable human coronary plaque*. Heart, 2004. 90; Virmani et al., *Lessons from sudden coronary death: a comprehensive morphological classification scheme for atherosclerotic lesions*. Arterioscler Thromb Vasc Biol, 2000. 20(5): p. 1262-75).

There is a significant need to help healthcare providers make therapeutic recommendations that are tailored to specific patients rather than taking a "one size fits all" approach with the available and future therapies for cardiovascular disease.

SUMMARY

The present disclosure provides methods and systems for selecting and recommending a suitable therapeutic treatment plan for a patient with cardiovascular disease, such as atherosclerosis. For example, physicians and other healthcare providers can use the new methods and systems to analyze and process non-invasively obtained data, such as imaging data, e.g., computed tomography angiography (CTA) data, of arteries from patients with atherosclerosis to obtain predicted proteomic and genomic information. Based on this information, various potential therapies, e.g., pharmacotherapies and/or procedural interventions, can be simulated based on their mechanisms of action in in silico systems biology models as described herein to enable the health care provider to provide a report to the patient recommending one or more specific pharmacotherapies and/or procedural interventions to be used to treat the patient.

This disclosure also provides methods for obtaining proteomic and/or genetic information and methods for building in silico systems biology models.

The in silico systems biology models are initially generated or trained with two types of data. First, one uses experimentally determined data from biological specimens from development subjects. Development subjects are people for whom actual proteomic data is available that shows differentially expressed protein levels that are linked to the specific characteristics and morphology of the plaques in each of those subjects. Second, one uses results from searches of public literature, experimental results, and/or other databases to find journal articles and the like to obtain detailed information about the proteins in the model. These two sources of data are used to create the initial in silico systems biology model.

The initial in silico systems biology model is then updated with calibration data, such as 'omics data, from test subjects to validate and refine the initial model. The calibration data is again based on actual biological samples that show differentially expressed protein and/or transcription levels that are linked to the specific characteristics and morphology of the plaques in each of those test subjects. This update of the initial model provides a calibrated in silico systems biology model. This step confirms that the model works as intended and also augments and renders the model more robust, given the calibration data from many test subjects.

Then in operation, the calibrated in silico systems biology model is again updated, but now with patient-specific personalized data based on imaging of the patient's plaque without the need to perform an invasive blood test or biopsy. The calibrated in silico systems biology model is also updated with the predicted effects of two or more different therapies. The methods and systems described herein use the patient's non-invasively obtained data, e.g., imaging data to provide a therapy recommendation based upon an automated comparison of the two or more different therapies whose predicted effects are programmed into the model.

In one aspect, the disclosure features methods of providing a recommendation of an anti-diabetic therapy for a patient with known or suspected atherosclerotic cardiovascular disease, the method including: receiving non-invasively obtained data related to a plaque from the patient; accessing a systems biology model of atherosclerotic cardiovascular disease, wherein (i) the systems biology model represents a plurality of pathways associated with atherosclerotic cardiovascular disease, (ii) the plurality of pathways correspond to one or more of MTOR, NFκβ1, ICAM1, or VCAM1, and (iii) the systems biology model includes a disease-associated molecule level for each molecule in the systems biology model; updating the systems biology model using personalized molecule levels derived from the non-invasively obtained data from the patient to generate a patient-specific systems biology model; updating the patient-specific systems biology model with information relating to an effect on glucose levels by an anti-diabetic agent based on a known mechanism of action of the anti-diabetic agent; simulating a therapeutic response by the patient to the anti-diabetic agent in the updated patient-specific systems biology model to obtain a simulated therapeutic effect; comparing the updated patient-specific systems biology model with and without the simulated therapeutic effect; and providing a report recommending the anti-diabetic agent for the patient when the comparison indicates an improvement for the patient.

In some aspects, the molecule is a gene, a protein, or a metabolite. In some aspects, simulating the therapeutic response comprises setting decreased levels of molecules related to plaque instability and setting increased levels of molecules related to plaque stability in the at least one network.

In some aspects, updating the systems biology model using personalized molecule levels comprises using disease gene transcript levels, disease protein levels, or a combination of both derived from the non-invasively obtained data.

In some aspects, the non-invasively obtained data is imaging data, such as radiological imaging data that can be obtained by computed tomography (CT), dual energy computed tomography (DECT), spectral computed tomography (spectral CT), computed tomography angiography (CTA), cardiac computed tomography angiography (CCTA), magnetic resonance imaging (MRI), multi-contrast magnetic resonance imaging (multi-contrast MRI), ultrasound (US), positron emission tomography (PET), intra-vascular ultrasound (IVUS), optical coherence tomography (OCT), near-infrared radiation spectroscopy (NIRS), or single-photon emission tomography (SPECT) diagnostic images, or any combination thereof.

In some embodiments, the methods further include processing the non-invasively obtained imaging data to obtain quantitative plaque morphology data including structural anatomy data, tissue composition data, or both. For example, the structural anatomy data can include data relating to a level of any one or more of remodeling, wall thickening, ulceration, stenosis, dilation, or plaque burden. In some embodiments, the tissue composition data includes data relating to a level of any one or more of calcification, lipid-rich necrotic core (LRNC), intraplaque hemorrhage (IPH), matrix, fibrous cap, or perivascular adipose tissue (PVAT).

In some aspects, the pathways are compartmentalized into cell-specific networks. For example, the cell-specific networks can include at least an endothelial cell network, a macrophage network, and a vascular smooth muscle cell network.

In some aspects, the anti-diabetic agent is metformin.

In some aspects, the method further includes recommending a combination of the anti-diabetic agent and one or both of a lipid-lowering drug and an anti-inflammatory drug.

In some embodiments, simulating the therapeutic response for the anti-diabetic agent in the patient-specific systems biology model includes: determining a set of molecules known to be affected by the anti-diabetic agent; defining a therapeutic effect molecule level for each molecule in the set of molecules based on one or more known mechanisms of action of the anti-diabetic agent on the set of molecules; and estimating a therapeutic effect molecule level for molecules represented in the patient-specific systems biology model other than in the set of molecules, based on a simulated effect of the defined therapeutic effect molecule levels of the set of molecules on one or more of the other molecules represented in the network.

In some aspects, the at least one network includes one or more pathways represented in Table 5 or Table 6 that are affected by glucose levels.

In another aspect, the disclosure also provides methods of identifying one or more contraindications associated with an anti-diabetic therapy for a patient diagnosed with atherosclerotic cardiovascular disease, the methods including: receiving non-invasively obtained data related to a plaque from the patient; accessing a systems biology model of atherosclerotic cardiovascular disease, wherein (i) the systems biology model represents a plurality of pathways associated with atherosclerotic cardiovascular disease, (ii) the plurality of pathways correspond to one or more of MTOR, NFκβ1, ICAM1, or VCAM1, and (iii) the systems biology model includes a disease-associated molecule level for each molecule in the systems biology model; updating the systems biology model using personalized levels of molecules derived from the non-invasively obtained data from the patient to generate a patient-specific systems biology model; updating the patient-specific systems biology model with information relating to an effect on glucose levels by an anti-diabetic agent based on a known mechanism of action of the anti-diabetic agent; simulating a therapeutic response by the patient to the anti-diabetic agent in the updated patient-specific systems biology model to obtain a simulated therapeutic effect; comparing the updated patient-specific systems biology model with and without the simulated therapeutic effect; identifying any one or more contraindications associated with the anti-diabetic agent based on the comparison; and providing a report indicating contraindications associated with the anti-diabetic agent for the patient.

In some embodiments, the molecule is a gene, a protein, or a metabolite.

In certain embodiments of the methods, the anti-diabetic agent is metformin.

In some embodiments, the at least one network includes one or more pathways represented in Table 5 or Table 6 that are affected by glucose levels.

Also provided herein are methods of screening a candidate anti-diabetic agent for atherosclerotic cardiovascular disease, the method including: receiving non-invasively obtained data related to a plaque from each of a plurality of test subjects who have been diagnosed with atherosclerotic cardiovascular disease; accessing a systems biology model of atherosclerotic cardiovascular disease, wherein (i) the systems biology model represents a plurality of pathways associated with atherosclerotic cardiovascular disease, (ii) the plurality of pathways include one or more pathways corresponding to potential targets of the candidate anti-diabetic agent, and (iii) the at least one network includes a disease-associated molecule level for each molecule in the systems biology model; updating the systems biology model using disease-associated molecule levels derived from the non-invasively obtained data from the test subjects to generate a validated systems biology model; updating the validated systems biology model with information relating to an effect on glucose levels by a candidate anti-diabetic agent based on a known mechanism of action of the candidate anti-diabetic agent; simulating a therapeutic response to the candidate anti-diabetic agent in the updated and validated systems biology model to obtain a simulated therapeutic effect; comparing a therapeutic effect in the updated and validated systems biology model before and after simulating the therapeutic response by the candidate anti-diabetic agent; and providing a report indicating the candidate anti-diabetic agent is a potential therapeutic agent when the comparison indicates the candidate anti-diabetic agent provides an glucose lowering effect.

In some embodiments, the molecule is a gene, a protein, or a metabolite.

In certain embodiments, the anti-diabetic agent is metformin.

In some embodiments, the at least one network includes one or more pathways represented in Table 5 or Table 6 that are affected by glucose levels.

In another aspect, the disclosure also provides methods of screening a potential subject for enrollment in a clinical trial testing safety or efficacy, or both, of a candidate anti-diabetic agent for atherosclerotic cardiovascular disease, the methods including: receiving non-invasively obtained data related to a plaque from the potential subject; accessing a systems biology model of atherosclerotic cardiovascular disease; updating the systems biology model using personalized molecule levels derived from the non-invasively obtained data from the potential subject to generate a subject-specific systems biology model; updating the subject-specific systems biology model with predicted molecular levels derived from information relating to an effect on glucose by a candidate anti-diabetic agent based on a known mechanism of action of the candidate anti-diabetic agent; simulating a therapeutic response by the potential subject to the candidate anti-diabetic agent in the updated subject-specific systems biology model to obtain a simulated therapeutic effect; comparing the updated subject-specific systems biology model with and without the simulated therapeutic effect; and providing a report indicating whether the potential subject's atherosclerotic cardiovascular disease would likely be improved or unaffected by the candidate anti-diabetic agent, and/or whether the potential subject would suffer an adverse effect from the candidate anti-diabetic agent.

Definitions

A "computational model" uses computer programs to simulate and study complex systems using an algorithmic or mechanistic approach.

A "predictive model" is a mathematical formulation often described as artificial intelligence, machine learning, or deep learning that computes one or more outputs ("response variables") form one or more inputs ("predictors"). In the present application, predictive models may be used for characterizing tissue (as a "virtual tissue model"), for predicting molecular levels form characterized tissues, or predicting outcome form either tissue characterizations and/or virtual 'omics.

A "systems biology model" refers to a model that is used to represent a set of interconnected biological pathways potentially used to simulate changes across those pathways under defined conditions.

An "in silico systems biology model" refers to a computational representation of a biological system, e.g., wherein the biological system is atherosclerotic cardiovascular disease.

An "initial in silico systems biology model" refers to an in silico systems biology model generated or trained with actual proteomic data obtained from development subjects and information obtained from literature searches.

A "calibrated in silico systems biology model" refers to an initial in silico systems biology model that is updated using measured calibration data, such as 'omics data, from a given subject (e.g., a test subject) who has been diagnosed with cardiovascular disease or from a patient with known or suspected cardiovascular disease.

"Calibration data" refers to test subject-derived data or patient-specific data that can be used to update an in silico systems biology model. Examples include measured 'omics data, such as, transcriptomics data, proteomics data, and/or metabolomics data, e.g., obtained non-invasively. Calibration data can also be obtained from molecular or tissue assays, e.g., biopsies.

"'Omics data" refers to biologically relevant quantities of gene expression, transcriptomics, proteomics, or metabolomics, based on directly measured molecular expression levels, e.g., by blood tests, molecular assays, or tissue biopsy.

"Virtual 'omics data" refers to computationally predicted levels of biologically relevant quantities of gene expression, transcriptomics, proteomics, or metabolomics (e.g., based on patient-derived imaging data) instead of directly measured molecular expression levels, e.g., by blood tests, molecular assays, or tissue biopsy.

A "network" refers to a graphical representation of interactions (edges) between various molecules (nodes).

An "artificial neural network" refers to a type of computational model, wherein the computational model is structured analogously to the human brain, as a series of interconnected "neurons" or mathematically as summations by weights and thus providing means to represent complex relationships with high degrees of non-linearity.

"Direction (of the edge)" refers to an orientation of an interaction between a pair of molecules (e.g., when molecule A activates molecule B, the direction would be A to B).

A "biological pathway" refers to a series of actions among molecules that leads to a certain product or a change.

"Baseline level" (of a molecule) refers to the biological state (e.g., expression level) of a molecule before perturbation in a systems biology model (e.g., in a healthy person or subject, before a test subject or patient was afflicted with a disease, or before a patient started a new treatment for a diagnosed disease).

A "disease-associated level" (of a molecule) refers to the quantitative amount of a molecule (gene transcript, protein, or metabolite) from an individual test-subject who has been diagnosed with a specific disease. In some instances, disease-associated levels of a molecule can be determined based on virtual 'omics data, which can include data obtained from plaque tissue, and may also include data from minimal disease tissue, as long as the data is taken from a test subject who has been diagnosed with the disease, e.g., a cardiovascular disease. Note that during model generation, disease-associated levels from test subjects are utilized, but during operation in the clinic personalized levels are used, where the word "calibration" applies to both in context.

A "personalized level" (of a molecule) refers to the quantitative amount of a molecule (transcript, protein, or metabolite) from an individual patient. In some instances, personalized levels of a molecule can be determined based on virtual 'omics data. Note that during model generation, disease-associated levels from test subjects are utilized, but during operation in the clinic personalized levels are used, where the word "calibration" applies to both in context.

A "phenotype" refers to the set of observable characteristics of an individual resulting from the interaction of its genotype with the environment. In this specification, it can be understood as also referring to "endotype" (a subtype of a disease condition, which is defined by a distinct pathophysiological mechanism), or "theratype" (a means to group according to their response to specific therapeutic alternatives), terms that are sometimes used in the field of precision medicine pertaining to the categorization or typing performed without loss of generality by the methods and systems described herein.

A "biochemical reaction" refers to an interaction among molecular quantities such as molecules (e.g., transcripts, RNAs, proteins, metabolites, inorganic compounds, etc.). Specifically, it refers to the transformation of one molecule to a different molecule inside a cell, usually (though not necessarily) annotated with quantitative coefficients or terms that allow effects to propagate across networks.

A "biochemical relation" is a semi-quantitative approximation to a biochemical reaction. "Reaction" and "relation" are used as alternatives in this disclosure (i.e., interchangeably) without loss of generality.

The new methods and systems described herein provide numerous advantages and benefits as well as improvements in the ability to provide patient-specific recommendations of therapies for atherosclerotic cardiovascular disease.

The number of people with atherosclerosis is very high. Most patients are unaware of their disease progression until onset of symptoms. Risk management of patients is largely dependent on population-based scoring methods such as Framingham Risk Score (Newby et al., *Coronary CT Angiography and 5-Year Risk of Myocardial Infarction*. N Engl J Med, 2018. 379(10): p. 924-933; Bergstrom et al.,

*The Swedish CArdioPulmonary BioImage Study: objectives and design.* J Intern Med, 2015. 278(6): p. 645-59) and development of diagnostics for more precise patient categorization is warranted. As treatment options for patients with CVD have become available, stratifying patients increasingly needs to be based on per-patient rather than population-based risk factors/scoring or simplistic imaging methods. For example, accessing a degree of stenosis, calcium scoring, or even fractional flow reserve (FFR) are not sufficiently specific for determining individual patient disease category at a level necessary to identify what treatment will best serve them, that is, to select among waiting, pharmacotherapy, procedural intervention, surgery, or a specific treatment within one of these categories. This is important economically as well as clinically, because recent advances in pharmaceuticals targeting specific mechanisms with increasing efficacy are generally more expensive than earlier generation drugs such as statins and are too expensive for use in broad populations. These new drugs are also not necessarily the best therapy for all patients and the present methods and systems can be used to match the right patients with the best therapies.

One current difficulty is that an ability to measure a response to a specific drug therapy remains elusive, and both under-treatment as well as over-treatment remain common problems, which can result in high numbers of patients that are needlessly treated while at the same time consuming financial resources and causing patients to go through needlessly invasive procedures for the results obtained. Likewise, to the extent that methods are proposed to assess vulnerable plaque, there remains the issue that just because a vulnerable plaque can be found, the causes for it are systemic rather than focal; often resulting in focal treatment being mismatched with the actual cause of the plaque, which can rather warrant systemic treatment. The concept of the "vulnerable patient" has been discussed, but we need markers to identify such individuals, and we need the ability to categorize the specific mechanism causing their vulnerability at an individual level, if we are to make demonstrable improvements in outcomes for given societal cost, for example by tailored therapeutics. Each of these needs and opportunities presents a challenge to the methods that have been developed so far, but are addressed by the methods and systems described herein.

The present disclosure fills gaps in understanding the extent and rate of progression of atherosclerosis under differing potential treatment alternatives. Advanced software-based techniques to extract data embedded in images, which are otherwise not readily appreciated visually or quantitatively, provide biomarkers to identify patients with unstable atherosclerosis and imaging to localize unstable atherosclerotic plaques, and provide more accurate characterizations extending from clinical care to developing drugs that are more effective for patients at risk of ischemic events.

The new methods and systems described herein provide outcome and cost improvements including improved non-invasive diagnostics to identify which patients have progressing disease, and the ability to provide automated recommendations of the best therapy or combination therapy for each specific patient based on simulations of how a specific therapy is likely to affect the specific patient and how the patient will respond given a specific therapy. The methods and systems can also be used to select or modulate doses of specific medications based on simulated patient responses, as well as be used to simulate the effects of new drug candidates, i.e., virtual clinical trials.

The presently described virtual biomarkers can go beyond indicating that there is a problem, to categorizing patients specifically as to the most effective way to treat the problem. Moreover, manifestations of conditions are considered both in terms of dynamic insufficiency (e.g., stress-induced ischemia of perfused tissues) as well as disruptive events such as thrombosis and rupture (i.e., causing infarction). Plasma biomarkers serve an important role as a screening tool, but by themselves are neither as sensitive nor as specific as knowing what is happening within a tissue, e.g., within and surrounding a plaque (i.e., the transcriptomics and proteomics of the tissue and the blood).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

This patent or application file contains at least one drawing executed in color. Copies of this patent or patent application publication with color drawing(s) will be provided by the Office upon request and payment of the necessary fee.

FIG. 6A is a schematic overview that shows how a specific systems biology model as described herein is created from molecular data and literature-based sources, then how that model can be updated based on test subject data to calibrate the initial model, and then how to update the calibrated model with patient imaging data and with data of the mode of action (MOA) of specific drugs that may be useful for a given patient to perturb the system to provide a per-patient simulated treatment response and a resulting therapy recommendation for that patient. Specific numbers shown are examples, without loss of generality.

FIG. 6B is a schematic that shows how three types of biological data can be derived from non-invasive radiology data using machine learning according to different reference truth bases. Input 1 from the figure represents patient data (CTAs) used not in the modeling, but to validate the models. Result 2 from the figure is a set of structural anatomic and tissue characterizations (quantitative plaque morphology) defined by histopathology. Results 3 and 4 represent virtual transcriptomics and virtual proteomics data defined by and validated from inputs "B" and "C" respectively. Without loss of generality, the input in "B" can be microarray or RNA seq data, or other means to assay coding or non-coding RNAs, and input in "C" can be liquid chromatography mass spectrometry or other means to assay protein levels.

FIG. 6C is a schematic that shows how the results from FIG. 6B can be used to calibrate reaction or relation quantities in a systems biology model. Here we focus on the molecular level, where item 2 (quantitative plaque morphology) is retained for continuity with FIG. 6B. Expression data 3 can be used to calibrate rate constants or the relative magnitude or weights in relations that pertain to how one molecule effects another. Level data 4 can be used to calibrate level of molecules. Together these reactions/relations are interconnected to comprise the systems biology model 5.

FIG. 13A is a map that represents those molecules that had direct measurements for the EC core network. FIG. 13B represents interpolated values that demonstrate propagation of levels from non-interpolated proteins according to type and weight of relation drawn from the pathway specification.

DETAILED DESCRIPTION

The methods and systems described herein not only characterize atherosclerosis in terms of morphology and stability based on non-invasively obtained data, e.g., non-invasive imaging data, of a patient's arteries (using, e.g., CT angiography), but further provide therapy recommendations for individual patients, based on the nature and stability of their plaques, all using only non-invasively obtained data from the patient, e.g., imaging data, such as arterial imaging data. For instance, by obtaining genotypic and/or phenotypic information (i.e., through virtual 'omics modeling, or based on actual measurements) for a given patient, the new methods and systems described herein can be used to model a patient's expected response to various therapies, including medicinal/pharmaceutical and interventional or procedural therapies, to recommend the therapy that is predicted to provide a superior outcome for that specific patient.

Figure 1:
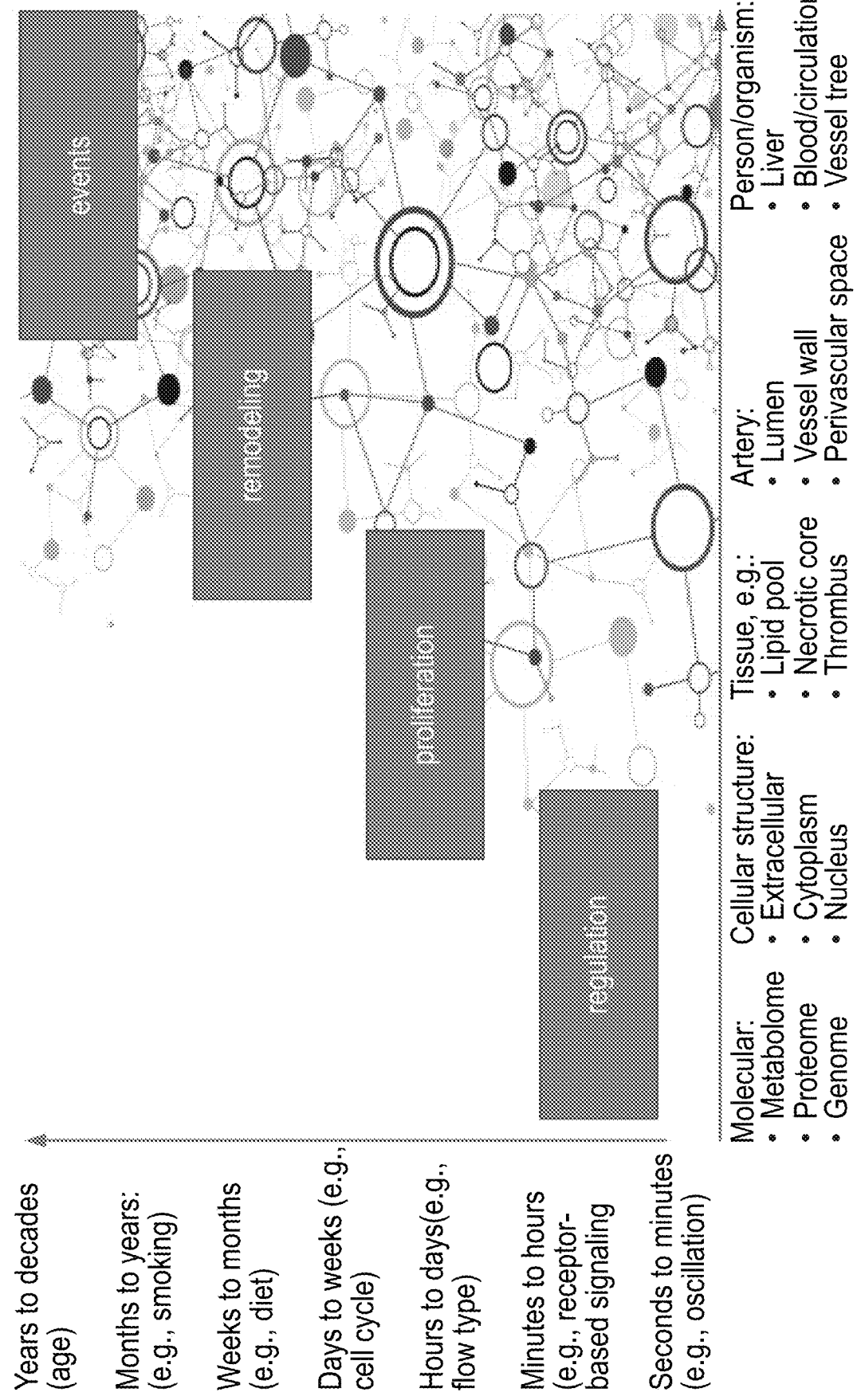
FIG. 1 is a high-level schematic flowchart showing how computational modelling can be used to express relationships among clinical, physiological, and molecular entities or concepts to describe pathogenesis in diseases such as atherosclerosis spanning multiple time scales and spatial scales.

Diagnostic accuracy is improved as the morphological and biological features of atherosclerotic plaques can be determined by non-invasive imaging. To do this, we have established a quantitative linkage between scales. Specifically, as shown in FIG. 1, as time progresses, atherosclerosis progresses on a spatial scale starting at the molecular level on a time scale of seconds to minutes, and progressing to the entire person level on a time scale of months, years, and decades. As described herein, we have used computational modelling techniques to express relationships that span multiple time- and spatial-scales.

The need for the new methods and systems is clear. Myocardial infarction (MI) and ischemic stroke (IS), major consequences of unstable atherosclerotic lesions, are the most common causes of death worldwide. However, any recommendations available for the prevention of MI and IS are currently based only on treatment efficacy at the group level, and practical means to tailor treatment for individual patients are a presently not available. To date, personalized treatment strategies for atherosclerotic cardiovascular disease (CVD) have not been possible. Other adverse outcomes from atherosclerosis include, without loss of generality, claudication, amputation, and various presentations of aorta disease such as aneurysm.

In the setting of CVD, we have used existing biobanks containing detailed disease-specific information at varying morphological and molecular scales to create dedicated in silico systems biology models, with applications including evaluation of drug side effects, consideration of drug combinations, and modelling of the effect of drugs and procedural interventions on a specific patient. The ability to identify in advance, whether an individual patient may or may not respond to a drug has a strong value. Our inclusion of broad molecular pathway analysis provides an advantage by addressing fundamental complexities needed for many clinical scenarios, when measurements of molecular species in plasma or tissue biopsies are not possible.

Incorporating molecular pathway analysis into an in silico setting however requires appreciation of the numerous structural and biological features that characterize the unstable atheroma, where a number of different pathways interleave in a complex set of interactions. For example: collagen fibers confer structural stability (World Health Organization (WHO). *Cardiovascular diseases (CVDs) Fact Sheet*, see, who.int/en/news-room/fact-sheets/detail/cardiovascular-diseases-(cvds) (2017)); collagen degradation the converse (Lambin et al., Radiomics: the bridge between medical imaging and personalized medicine. *Nature Reviews Clinical Oncology* 14, 749-762, doi:10.1038/nrclinonc.2017.141 (2017)). Reductions in atherogenic lipoproteins resulting from phospholipid and cholesterol efflux improve stability (Lee et al., Radiomics and imaging genomics in precision medicine. *Precision and Future Medicine* 1, 10-31 (2017)); endothelial to mesenchymal transition can influence tissue structure with both stabilizing and destabilizing effects (Buckler et al., Virtual Transcriptomics: Non-Invasive Phenotyping of Atherosclerosis by Decoding Plaque Biology From Computed Tomography Angiography Imaging. *Arteriosclerosis, thrombosis, and vascular biology*, Atvbaha121315969, doi:10.1161/atvbaha.121.315969 (2021); Peyvandipour et al., Novel computational approach for drug repurposing using systems biology. *Bioinformatics* 34, 2817-2825 (2018)); and perivascular adipose tissue has been suggested to increase plaque inflammation (Nguyen et al., Identifying significantly impacted pathways: a comprehensive review and assessment. *Genome biology* 20, 1-15 (2019); Réda et al., Machine learning applications in drug development. *Computational and structural biotechnology journal* 18, 241-252 (2020); Pai et al., netDx: interpretable patient classification using integrated patient similarity networks. *Molecular systems biology* 15, e8497 (2019)), resulting in atherothrombosis, MI, or IS (Adam et al., Machine learning approaches to drug response prediction: challenges and recent progress. *NPJ precision oncology* 4, 1-10 (2020)).

According to the present disclosure, given the complexity and multifactorial biology of atherosclerosis, comprehensive disease modelling as presented herein required the consideration of more complete biological networks than have been reported to date. To capture sufficiently granular information including prediction of disease-critical biological responses to different drugs, we included biological processes represented by pathway networks of molecular interactions essential for disease progression.

In the present disclosure, we describe comprehensive in silico systems biology models of atherosclerosis using curated networks of molecular pathways to effectively describe and predict unstable disease. Using molecular data from plaque specimens from test subjects, we incorporated disease-specific pathways across multiple cell types to develop an integrated in silico systems biology model, we can then use this calibrated in silico systems biology model to make therapy recommendations for individual patients. We evaluated the potential of the model by simulating the effects of different pharmacological treatments on molecular processes relevant for stabilization of atherosclerotic lesions, effectively predicting personalized pharmacological effects and highlighting a potential for clinical utility and tailored therapy for prevention or inhibition of adverse events such as MI and IS.

The present disclosure also provides systems and methods of using these models to provide patient-specific therapy recommendations for individual patients based only on non-invasive arterial imaging data.

I. Methods of Obtaining
Phenotypic/Endotypic/Theratypic Data Based on
Virtual 'omics Modeling Information about prevalent biological processes that are related to plaque characterization and stability can be obtained non-invasively through virtual 'omics methods. Briefly, methods include receiving a non-invasively obtained imaging dataset for an atherosclerotic plaque from a subject; processing the non-invasively obtained imaging dataset to obtain quantitative plaque morphology data; processing the quantitative plaque morphology data with a virtual expression model to obtain estimated protein and/or gene expression data for the plaque from the subject; and generating phenotypic data for the atherosclerotic plaque from the subject based on the molecular data.

The phenotypic data refers to the set of observable characteristics of an individual patient, test subject, or development subjects, resulting from the interaction of their genotype with the environment. In particular, the phenotypic data can include endotypic data, which relates to a subtype of a disease condition that is defined by a distinct pathophysiological mechanism, and/or theratypic data, which is used to group patients or test subjects according to their response to specific therapeutic alternatives.

Non-Invasively Obtained Data

The first step in obtaining patient or subject data for the methods and systems described herein is to obtain data non-invasively. For example, that data can be imaging data, i.e., image(s) of the plaques in arteries, and can be obtained by various methods that are well known in the art. In some embodiments the imaging dataset is obtained by radiological methods. For instance, any of the following can be employed: computed tomography (CT), dual energy computed tomography (DECT), spectral computed tomography (spectral CT), computed tomography angiography (CTA), cardiac computed tomography angiography (CCTA), magnetic resonance imaging (MRI), multi-contrast magnetic resonance imaging (multi-contrast MRI), ultrasound (US), positron emission tomography (PET), intra-vascular ultrasound (IVUS), optical coherence tomography (OCT), near-infrared radiation spectroscopy (NIRS), or single-photon emission tomography (SPECT). In a particular embodiment, CTA is utilized.

For example, in one embodiment, CTA can be performed as a pre-operative routine procedure in the hospital using site-specific image acquisition protocols. CTA exams can be performed with 100 or 120 kVp, variation of $CTDIvol16cm$ between 13.9 and 36.9 mGy or $CTDIvol32cm$ 7.9-28.3 mGy. Contrast injection rates and amounts followed by a saline chaser can be used as required. In general, a caudocranial scanning direction can be selected from the aortic arch to the vertex, using intravenous contrast. An axial image reconstruction of about 0.5 to about 1.0 mm, e.g., 0.65 mm, 0.9 mm, or 1.0 mm can be used, and transferred into a digital workstation for vascular CTA image analysis.

Variations of these examples of non-invasive imaging are contemplated and could be used by those of skill in the art.

Tissue Models

Data, such as imaging data obtained from the non-invasive imaging methods described herein are loaded into an image processing software, e.g., ElucidVivo® (Elucid Bioimaging Inc., Boston, Mass.) software, which outlines (segments) the luminal and outer wall surfaces of the common, internal, and external arteries to provide quantitative plaque morphology data. See also, U.S. Pat. Nos. 10,176,408, 10,740,880, 11,094,058, and 11,087,460, each of which is incorporated herein by reference. Specifically, the software creates fully 3-dimensional segmentations of lumen, wall, and each tissue type at an effective resolution≈3× higher than the reconstructed voxel size with improved soft tissue plaque component differentiation relative to manual inspection. The common and internal artery are defined as a target with lumen and wall evaluated automatically and, when needed, edited manually.

The software provides vessel structure measurements including the degree of stenosis (calculated both by area or diameter), wall thickness (distance between the lumen boundary to outer vessel wall boundary), and remodeling index (the ratio of vessel area with plaque to a vessel area without plaque used as reference). Investigations in animal models and histological analyses of human plaque lesions have characterized distinct, but common, structural and biological tissue characteristics such as enhanced inflammation, accumulation of a large lipid-rich and necrotic central core (LRNC), intra-plaque hemorrhage (IPH), a thin and rupture-prone fibrous cap from extracellular matrix (ECM) degradation, apoptosis of smooth muscle cells (SMCs), level of calcification (CALC), matrix/fibrous tissue (MATX), and fibrous cap/perivascular adipose tissue (FC/PVAT).

The software includes algorithms to decrease blur caused by image formation in the scanner. A patient-specific 3-dimensional point spread function is adaptively determined so that image intensities are restored to represent the original materials imaged more closely, which mitigates artefacts such as calcium blooming, and enables discrimination of less prominent tissue types. In particular, the image restoration is undertaken in concert with tissue characterization based on expert-annotated histology (which includes both proteome and transcriptome information), e.g., as described in U.S. Pat. Nos. 10,176,408, 10,740,880, 11,094,058, and 11,087,460, each of which is incorporated herein by reference.

Figure 2A:
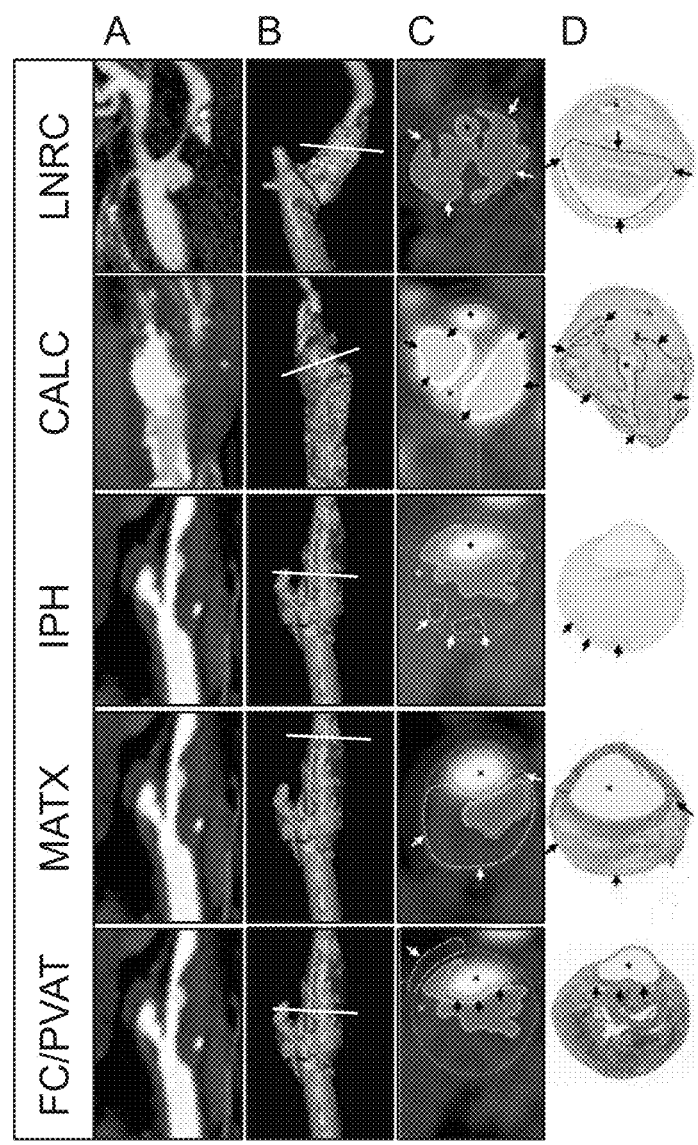
FIG. 2A is a series of non-invasive computed tomography angiography (CTA) images of an artery (left most column, labeled as column A), 3D image generated from the CTA (column B), 2D/axial images of the CTA images (column C, where the white line in the images in column B indicate the position of the section), and histological images (column D) of tissues that have the following characteristics lipid-rich necrotic core plaque (LRNC), calcification (CALC), intra-plaque hemorrhage (IPH), matrix/fibrous tissue (MATX), and fibrous cap/perivascular adipose tissue (FC/PVAT). Specific tissues shown are examples, without loss of generality.

As shown in FIG. 2A, CTA can be processed to obtain 3D images. FIG. 2A includes four columns of images (from left to right) that show CTA images (column A), processed images (columns B and C, and corresponding histopathology annotation (column D). Specifically, as described above, the images in column A were processed using the ElucidVivo® software to create fully 3-dimensional segmentations of lumen, wall, and each tissue type at a high resolution, as shown in columns B and C of FIG. 2A. Finally, column D of FIG. 2A shows the corresponding histological sections stained with Hematoxylin (LRNC, CALC), Perl's blue (IPH; arrows) and Masson's Trichrome to visualize fibrous tissue (MATX).

Figure 2B:
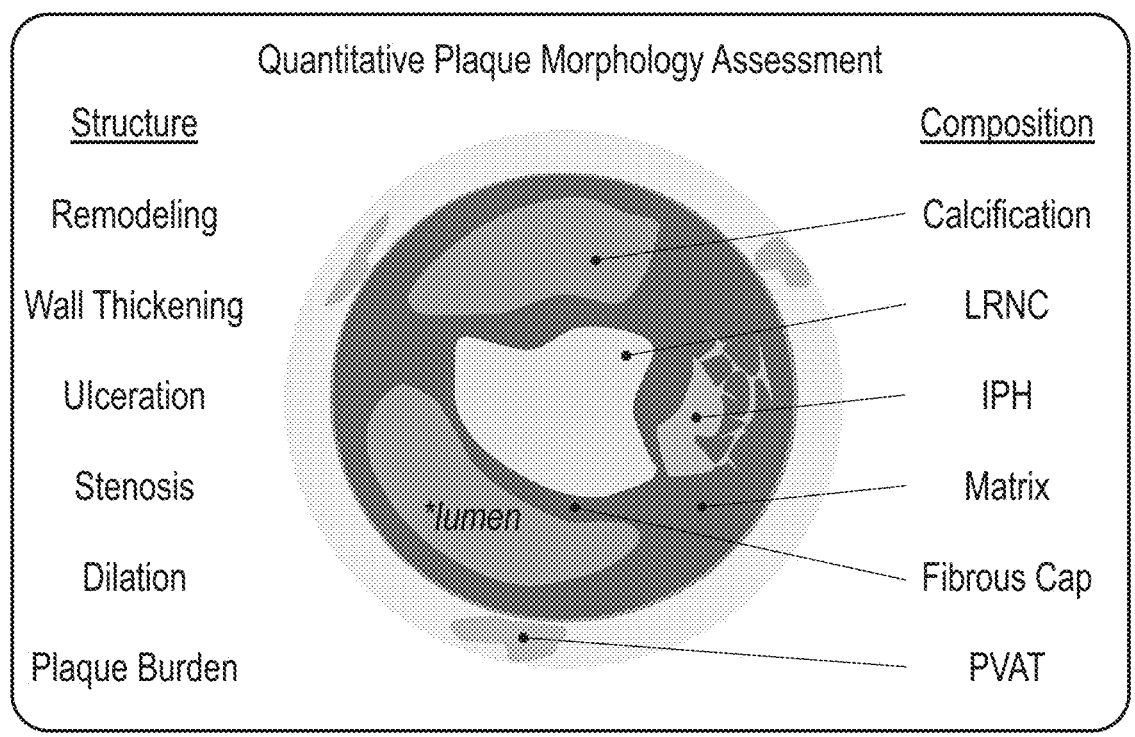
FIG. 2B is a schematic image showing multiple objectively validated measurements to characterize plaque morphology by analysis software. Among those measurements, tissue can be differently colored elements to define its type, for example to be one of the following categories: LRNC, CALC, IPH, matrix, fibrous cap, and PVAT, or other relevant tissue types as needed. Specific tissues shown are examples, without loss of generality.

Processing of the CTA images allows for multiple objectively validated measurements to be made, thereby permitting the characterization of plaque morphology by CTA analysis software. These assessments included structural anatomy ("structure") and tissue characterization ("composition") as shown in FIG. 2B. FIGS. 2A and 2B both show tissues that have a lipid-rich necrotic core (LRNC), calcification (CALC), intra-plaque hemorrhage (IPH), matrix/fibrous tissue (MATX), and fibrous cap/perivascular adipose tissue (FC/PVAT). These specific tissues types are provided as examples without loss of generality.

The overlapping densities of tissues such as LRNC and IPH, for example, necessitate a method for accurate classification. To avoid limitations of conventional analysis of CTA utilizing fixed thresholds, the accuracy required for elucidating molecular pathways was achieved by algorithms that account for distributions of tissue constituents rather than assuming constant material density ranges. In this way, the software makes mathematical judgments to interpret the Hounsfield units (HU) of adjacent voxels by maximizing criteria that mimic expert annotation at microscopy, simultaneously mitigating variation between scanners, reconstruction kernels, and contrast levels. In this way, the software fundamentally addresses subjectivity intrinsic to other analysis methods.

Processing the non-invasively obtained image data with the software provides output information relating to quantitative plaque morphology, such as structural anatomy data and tissue composition data. For example, structural anatomy data includes measuring any one or more of the following in the lumen and wall: remodeling, wall thickening, ulceration, stenosis, dilation, plaque burden, or any of the measurands listed in the Table 1 below.

As outlined in Table 1, vessel structure measurements include the degree of stenosis (calculated both by area or diameter), wall thickness (distance between the lumen boundary to outer vessel wall boundary), and remodeling index (the ratio of vessel area with plaque to a vessel area without plaque used as reference).

TABLE 1

Structural Calculations of Vessel Anatomy

| Measurand | Description | Type and Units |
|---|---|---|
| Lumen Area | Cross-sectional area of blood channel along the vessel centerline | mm² |
| % Stenosis (Max Stenosis) | (1 - ratio of minimum lumen with plaque to reference lumen without plaque) ×100, both by area and by diameter | % |
| Wall Area | Cross-sectional area of vessel minus the Lumen Area along the vessel centerline | mm² |
| Wall Thickness | Maximum cross-sectional wall thickness along the vessel centerline | mm |
| Max Wall Thickness | Largest value of the wall thickness | mm |
| Plaque Burden | Wall Area/(Wall Area + Lumen Area) | Unit-less ratio |

Tissue composition data includes calcification (CALC), lipid-rich necrotic core plaque (LRNC), intra-plaque hemorrhage (IPH), and matrix/fibrous tissue (MATX), see Table 2 below.

TABLE 2

Calculations of Tissue Characteristics

| Measurand | Biological Evidence on Histopathology |
|---|---|
| Calcification | intimal/medial spaces with evidence of calcium primarily in the form of hydroxyapatite<br>osteoblasts or osteoid present in above spaces<br>no appreciable lipid or necrotic tissue in above spaces |
| Lipid-rich Necrotic Core (LRNC) | lipid droplets intermixed ECM (appear clear due to removal)<br>necrotic amorphous eosinophilic material<br>acellular<br>often surrounded by fibrotic tissue generated by smooth muscle cells/fibroblasts<br>lack of microvasculature |
| Intra-plaque Hemorrhage (IPH) | erythrocytes in the deeper regions of the plaque with or without communication to lumen or neovasculature<br>Fresh: RBC is intact and unorganized<br>Recent (5+ days): inflammatory response organizes the RBC via hemolysis, fibroblast activity, macrophage activity |
| Matrix | Note elongated striated appearance which describe: intimal meshwork of dense or loose, homogeneous/organized collagen ECM (appear striated)<br>embedded smooth muscle cells/fibroblasts (note elongated nuclei)<br>no appreciable lipid or necrotic tissue<br>may have microvasculature |

Volume measurements, either in place of or additive to area measurements can also be utilized. Likewise, various forms of spatially labelled data that represent these can also be used. These specific tissues types are provided as examples without loss of generality.

Figure 3A:
FIGS. 3A-3F are a series of histology images (left column) and images of non-invasive computed tomography analyses (middle column) of two subjects in a study cohort with unstable (A-C) and stable (D-F) atherosclerosis. The middle column (FIGS. 3B and 3E) show a 3D view provided by imaging software. The right column (FIGS. 3C and 3F) show classifier output for stability phenotypes aligned with the 3D images, where red signifies an unstable plaque, yellow a stable plaque, and green minimal disease.
Figure 3B:
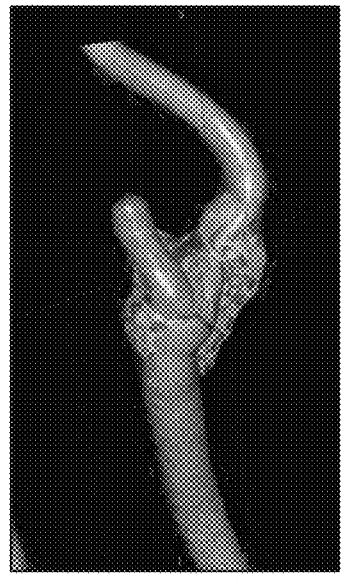
Figure 3C:
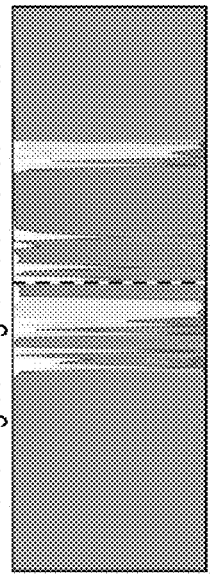
Figure 3D:
Figure 3E:
Figure 3F:
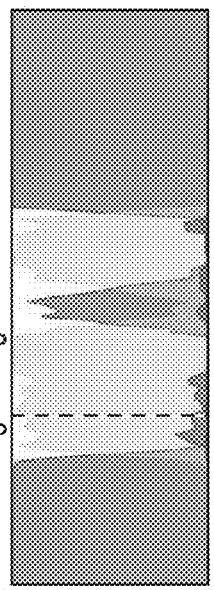

FIGS. 3A-3F show an exemplary embodiment of histology and non-invasive computed tomography analysis of two patients in the study cohort described in the Examples below with unstable (FIGS. 3A-3C) and stable (FIGS. 3D-3F) atherosclerosis. Histology with Masson Tri Chrome staining of the CEA specimens (FIG. 3A) showed extensive lipid-rich necrotic core with rupture of the fibrous cap in the unstable lesion, whereas the stable example was dominated by fibrosis and abundant collagen (FIG. 3D). The histological presentation of the two phenotypes corresponded to results of non-invasive CTA analysis with the ElucidVivo software, visualized in 3D view (FIGS. 3B and 3E), and with classifier output for stability phenotype (FIGS. 3C and 3F; originally in color where red=unstable plaque features, yellow=stable plaque features, green=minimal disease). Other stains such as H&E, Movat, or others can be used without loss of generality.

Virtual 'Omics Models

As described in further detail below, the virtual 'omics models are built from a variety of machine learning models. Briefly, any of several methods, devices, and/or other features are used to perform a specific informational task (such as classification or regression) using a number of examples of data of a given form, and are then capable of exercising this same task on unknown data of the same type and form from a new patient or subject. The machine (e.g., a computer or processor) will "learn," for example, by identifying patterns, categories, statistical relationships, etc., exhibited by training data. The result of the learning is then used to predict whether new data exhibits the same patterns, categories, and statistical relationships.

Examples of such models include neural networks, support vector machines (SVMs), decision trees, hidden Markov models, Bayesian networks, Gram Schmidt models, reinforcement-based learning, genetic algorithms, and cluster-based learning. Multiple can be used to create the pool of trained machines from which the choice is made. These can include methods of feature selection and reduction, ranking of features, random generation of feature sets, correlations among features, PCA (Principal Component Analysis), ICA (Individual Component Analysis), parameter variation, and any methods known to those skilled in the art.

Supervised learning occurs when training data is labelled to reflect the "correct" result, i.e., that the data belongs to a certain class or exhibits a pattern. Supervised learning techniques include neural networks, SVMs, decision trees, hidden Markov models, Bayesian networks, etc. Test data sets encompassing known class(es) can be used to determine if a trained learning machine is able to identify patterns in data and/or classify data. The test data set is preferably generated independently from the training data set. Training Data sets (of known or unknown classes) are used to train a learning machine. Regardless of whether the class of the data is known or unknown, the data can be adequate for training a learning machine. Unsupervised learning occurs when training data is not labelled to reflect the "correct" result, i.e., there is no indication within the data itself as to whether the data belongs to a class or exhibits a pattern. Unsupervised learning techniques include Gram Schmidt, reinforcement-based learning, cluster-based learning, etc.

Thus, certain embodiments of the present invention can utilize machine learning methods and/or deep learning methods, although these methods are not always required in all embodiments.

Figure 6A:
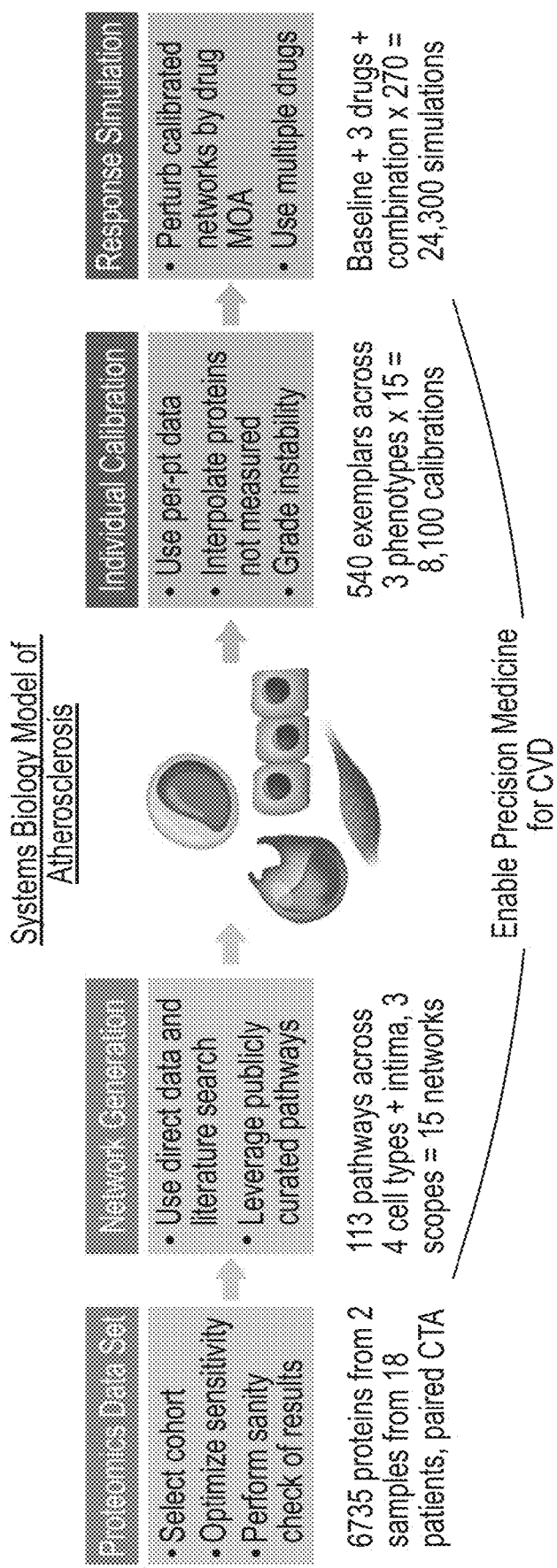
FIGS. 6A-6C, collectively, are images showing the workflow steps taken to create an in silico systems biology model of atherosclerosis for simulation of individual subject responses to different therapies, e.g., pharmacotherapies and/or procedural interventions.
Figure 6B:
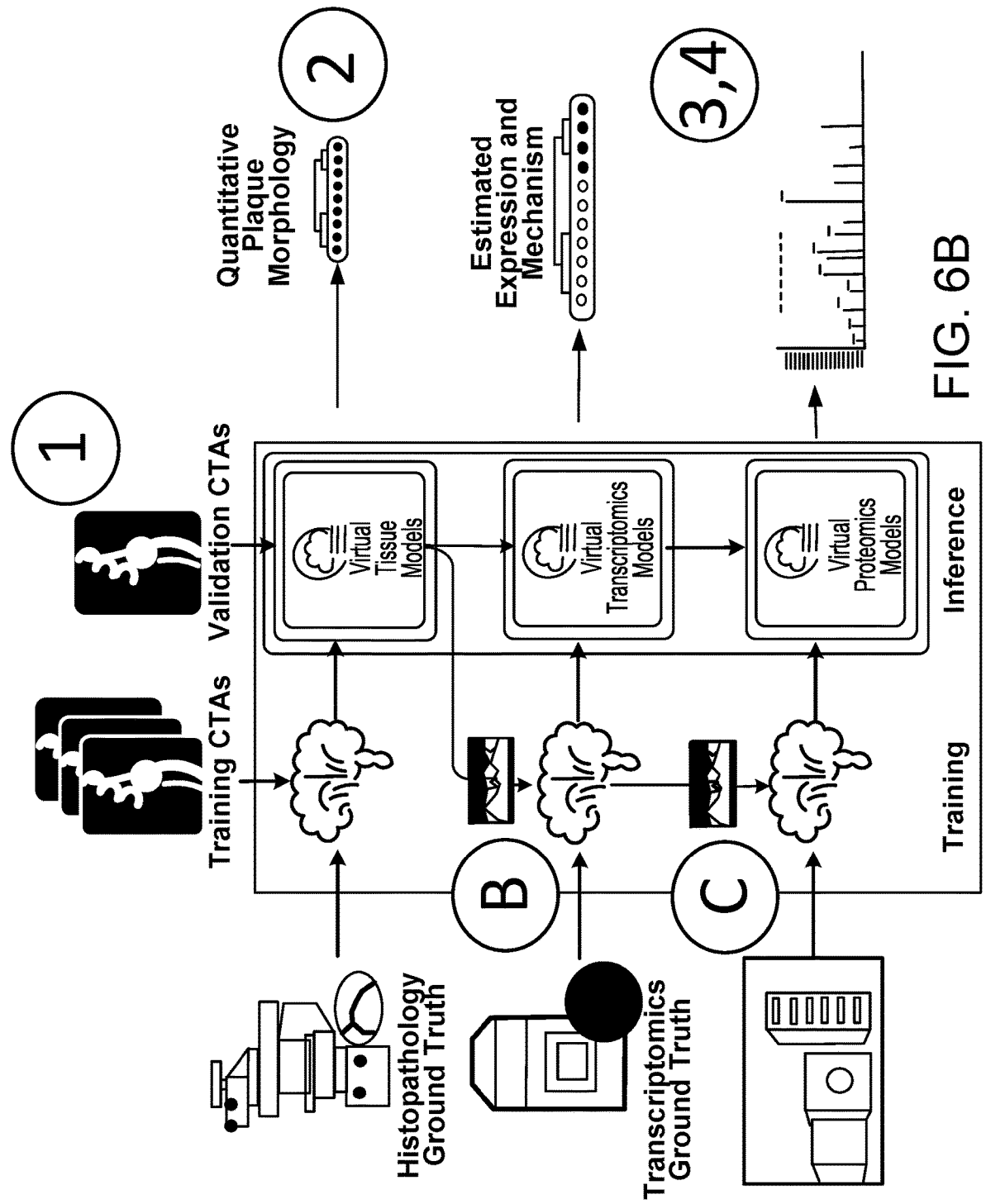

In one embodiment, one or more neural network(s) can be generated and/or updated with virtual 'omics from vascular CT images processed as described in FIGS. 2A and 2B according to the Virtual Tissue Models in FIG. 6B and together comprising the Quantitative Plaque Morphology data in FIG. 6B and optionally additional covariates. One or more neural networks ingest the 3D vessel image and, across multiple layers, combine the spatially-resolved signal with the covariate information encoded as scalars (for example, vessel location, patient demographics, etc., without loss of generality), to provide calibration data according to the Virtual Expression and Virtual Proteomics models in FIG. 6B producing the individual patient calibration data comprising molecular level information utilized by the systems biology model.

This method overcomes two problems. First, the quantity of annotated data, required for training, is both low and high dimensional of the CT image volume. The present disclosure exploits the dimensionality reduction provided by the Virtual Tissue Models, which also provide an opportunity for objective validation. We also leverage the large quantity of unlabeled vessels which is enabled from the use of this validated image processing step, from which the virtual 'omics networks can learn a rich representation of vessel structure in a semi- or self-supervised manner. Second, the output has high dimensionality. We address this by employing a neural architecture that constructs a common representation of the input, which is shared across the components which predict individual 'omics levels.

In another embodiment, one or more deep learning network(s) can be used for adverse event prediction and/or drug interaction effects. The common representation described herein can be imported into a new model, which will use the features it provides to predict adverse events directly or after further fine-tuning with labelled data. These features can also be fused with numerical predictions from the systems biology model to estimate drug interaction effects.

In another embodiment, neural networks can be used to implement portions or the whole of the therapy effect simulations, noting that portions of the systems biology model itself may be differentiable. Reaction kinetics networks are comprised fundamentally of systems of coupled ODEs and PDEs which may be implemented within neural networks to enable speedups in both model training and model inference. Neural networks can be employed to find favorable initializations of such reaction networks to allow optimal solutions efficiently.

Generating Phenotypic, Endotypic, and/or Theratypic Data for Atherosclerotic Plaques The quantitative plaque morphology data (which relates, e.g., to the profile, characterization, type of plaque) received from the processing of CTA images, as described in the section "Tissue Models" above, is processed against one or more virtual proteomic/transcriptomic models, as described above, to obtain estimated/predicted gene expression and/or protein level data for the plaque from the subject. In other words, the tissue models are further processed against known gene-expression and/or known protein levels patterns (that is, the tissue models based on the imaging data are correlated to gene-expression and/or protein levels patterns) to generate a predicted 'omics model.

The predicted 'omics model then, in turn, allows the clinician to predict which 1) gene transcript levels are likely elevated and which gene levels are likely decreased in the plaque and/or 2) protein levels are likely elevated and which protein levels are likely decreased in the plaque. 'Omics levels (elevated/decreased/unchanged) are in reference to a non-atherosclerotic patient. As a result, this data provides information about the mechanisms related to plaque pathophysiology, plaque instability, or other relevant biological insight, thereby generating phenotypic, endotypic, and/or theratypic data for the atherosclerotic plaque from the subject.

II. Methods of Generating an in Silico Systems Biology Models

Generating and Training an in Silico Systems Biology Model

The in silico systems biology model is initially generated or trained with two types of data. First, we use experimentally determined data from biological specimens from development subjects. Development subjects are people for whom actual proteomic data is available that shows differentially expressed protein levels that are linked to the specific characteristics and morphology of the plaques in each of those subjects. Second, we use results from searches of public literature, experimental results, and/or other databases to find journal articles and the like to obtain detailed information about the proteins in the model. These two sources of data are used to create the initial model.

An example of a mathematical framework for multi-scale analysis is shown below:

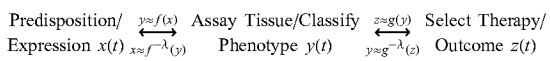

The function y(t) refers to a phenotype y at time t. Function x is the cellular and molecular level at time t, and z represents the patient-level outcome or state at time t. The present disclosure provides systems of equations, or non-linear models, $f$ and $g$, where $f$ decreases in scale and $g$ increases in scale. One example of function $f$ is a predictive modeling paradigm, where y can be expressed as scalar, vector, or multidimensional data as pictured, to derive expression profiles, protein concentrations, or other lower level information. One example of function g can also be a predictive model, but a different model than $f$, one that increases in scale. Inverse functions for $f$ and g can also be derived.

Figure 4:
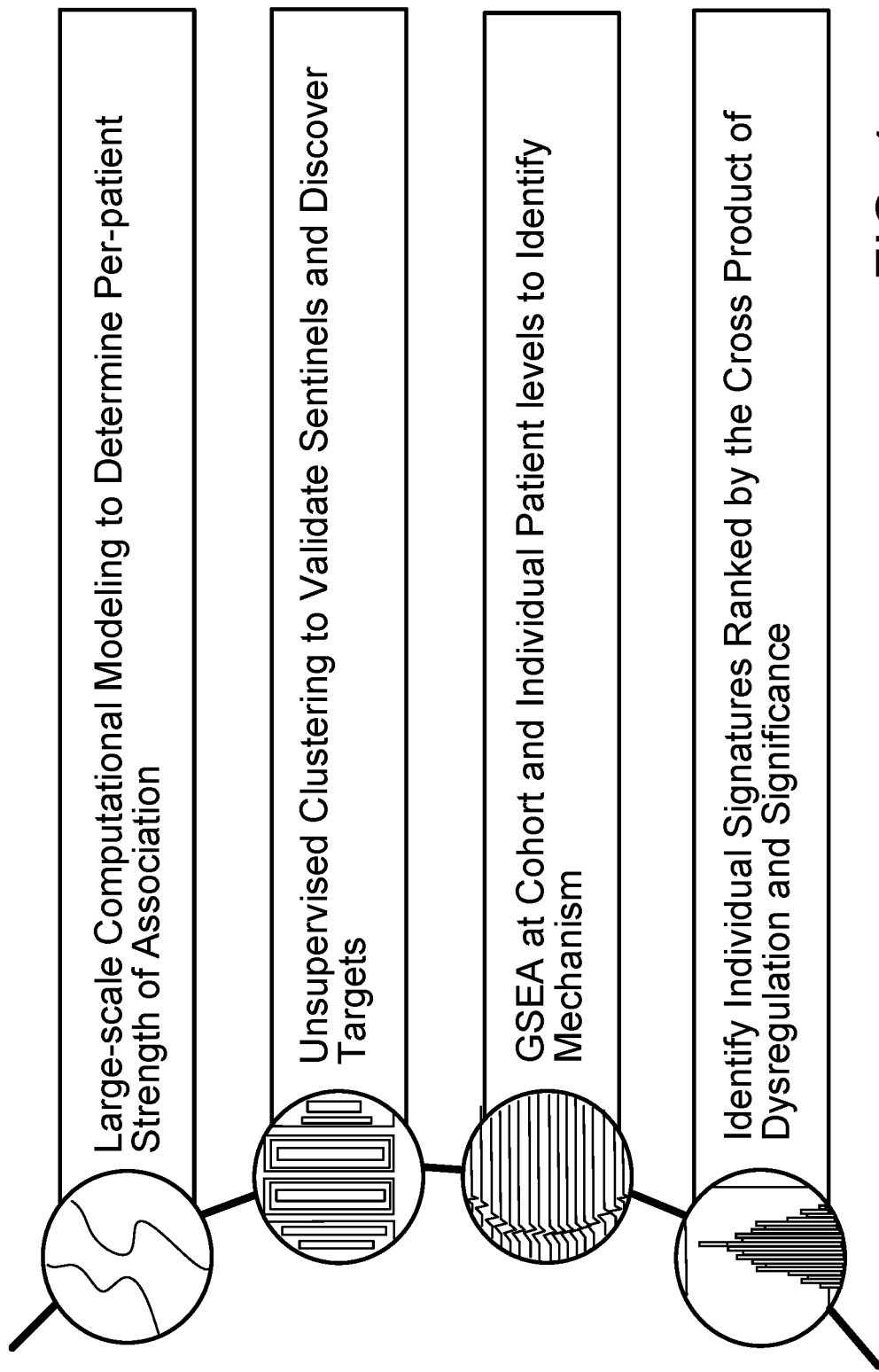
FIG. 4 is a workflow outlining the steps for determining a function ƒ, using training data sets to optimize models of various types, and the results can be further applied to supervised or unsupervised clustering for use in virtual 'omics.

Further detail is given in FIG. 4. Here, steps are outlined for determining the function $f$. Training data sets are used to optimize models of various types, and the results can be further applied to supervised or unsupervised clustering. The resulting associations, at the cohort or individual level, can be analyzed using techniques such as gene-set enrichment analysis (GSEA) to elucidate biological processes and molecular pathways at the cohort level, and/or in individual patients. GSEA can be conducted, for example, using EnrichR (see, amp.pharm.mssm.edu/Enrichr), further passing results from Gene Ontology Biological process, and further by passing data to other systems such as Revigo (revigo.irb.hr) to determine, for example, non-duplicative processes. Individual patient level inference can be applied where both degree of dysregulation as well as statistical model significance can be taken into account. This can be variously described as virtual 'omics.

The virtual 'omics models themselves can be utilized, without loss of generality, for example, as follows. All or a selection of probes from a microarray, or species from mass spectrometry, or other assay method for obtaining so-called 'omics data, can be selected. Single as well as multiple variable regression models covering linear and non-linear modelling techniques can be performed on predictor sets constructed from a development cohort including plaque morphology, demographics, clinical (laboratory) values, and/or other variables, in part to recognize that clinical factors can affect the expression data or models, and to inspect what is the added value of morphology over clinical and demographic data, and to identify when morphology and other variables have independent information content, different predictor sets can be used, some only using plaque morphology, but others also using lab values, demographic, and other values in composite models. Each model result can be output and tabulated to identify the highest-achieved performance on a species-by-species basis.

Predictive performance can be determined based on the accuracy of the prediction relative to the true or reference values. Models can be built with variations, for example, differing sets of morphological measurements according to hypothesized physiological rationale, automated optimization using for example cross validation while simultaneously varying tuning parameter values; and/or, partitioning data such that a training set on which the cross-validation was performed was strictly separated from a sequestered validation data set to test performance using locked-down models. Use of histologically validated plaque features, for example, can produce interpretable models, and when coupled with cross-validation, can mitigate overfitting.

Supervised model quality (MQ) can be determined, by way of example, but not only by this method, as the product of two measures for each model type. MQ for continuous estimation models was computed as the product of concordance correlation coefficient (CCC) and regression slope of predicted vs. observed for continuous value estimation (the former to measure the tightness of fit, but augmented by the latter to ensure proportional prediction relative to observed). MQ for dichotomized categorical prediction models was computed as the product of area under the receiver characteristic curve (AUC) times Kappa for dichotomized prediction (the former to measure the net classification performance, but augmented by the latter to ensure performance in both high and low expression classes).

The forgoing can be implemented using deep learning networks of various network topologies, and using either raw imagery, or enriched images identified with tissue type annotations, and/or that result from spatial normalizations such as, but not limited to, unwrapping.

Recognizing the existence of the various virtual 'omics processing steps, the present disclosure builds on that base with further steps that provide further utility. For example, models of the complex biological behavior sometimes referred to as pathways or cell signaling networks are described with mathematical formalisms using differential equations or other mathematical formalisms that capture behavior such as mass transfer, reaction dynamics that stem from enzymes, various inhibitory processes, and other approximations to biochemical reactions/relations.

Figure 5:
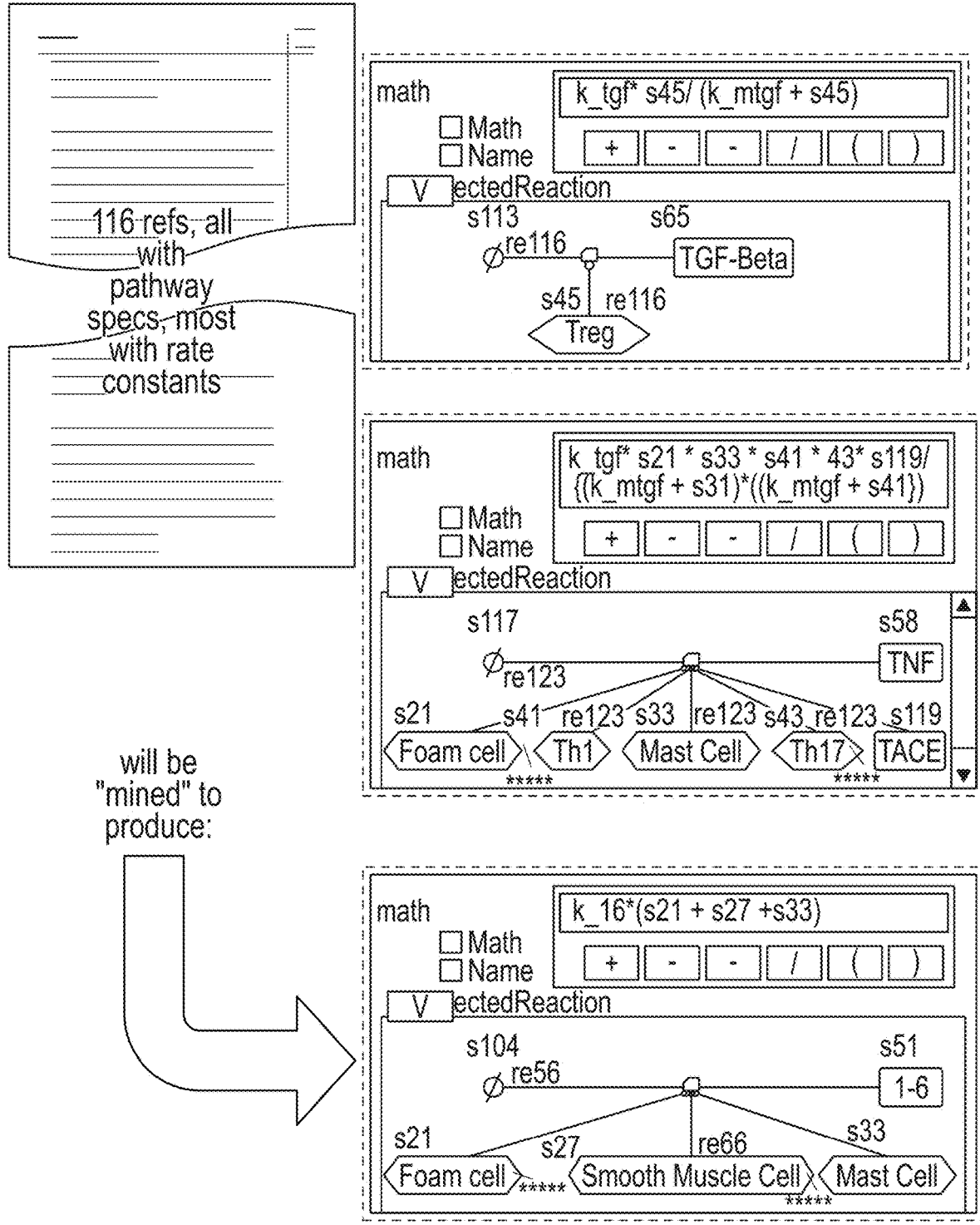
FIG. 5 is a workflow showing an example of how reactions or relations (i.e., interactions along biological pathways) are identified and concentrations/rate constants, or other quantitative relationships are enumerated. Note that the number 116 is an example but either more or less references may be used without loss of generality, and it should also be noted that whereas many resources are in the public domain, proprietary or unpublished resources can also be used without loss of generality.

In general, the numeric variables identified are descriptive of the behavior expected in groups of patients or animals, that is, in general, they are not applicable to a specific individual; but they do provide a structure and calibration levels for patient groups. One example embodiment is diagrammed in FIG. 5, where literature references and/or in vitro studies are mined or conducted respectively to elucidate terms in the systems biology equations, for example, concentrations, levels, and/or rate constants. Specifically, as shown in FIG. 5, the literature is mined to identify reactions between biological molecules (left part of the figure). It should be noted that there are a number of software tools capable of representing this information visually and programmatically including such tools as Cell Designer (https://www.celldesigner.org/), cytoscape (see, cytoscape.org), etc. Specific sources and reactions shown are examples, without loss of generality.

On the right side of FIG. 5, the reactions are mapped. On the top right, shown is the relationship between TGFβ and Treg. On the middle right, shown is the relationship between TNF and foam cells, Th1, mast cells, Th17, and TACE. On the bottom right, shown is the relationship between TL-6, foam cells, smooth muscle cells, and mast cells. By this method, as described in more detail below, these reactions were modeled and tied together in multi-compartment systems biology models, in general with compartments for other organs, the plasma, etc., to the extent that they have an effect on atherosclerotic development. Parton et al., New models of atherosclerosis and multi-drug therapeutic interventions. *Bioinformatics* 35, 2449-2457, doi:10.1093/bioinformatics/bty980 (2018)).

The present disclosure moves beyond patient groups to provide the facility to reach individual patient-level results. As shown in FIG. 6A, the present disclosure provides methods to use results vectors of virtual 'omics and virtual 'omics data from individual patients (whether they be test subjects to validate the method or of course the intended patients seen in clinical practice this invention seeks to support) with known or suspected CVD to train and update individual level rate constants and concentrations respectively in the in silico systems biology model. This has the effect of using a systems biology model developed with generalized data (e.g., updated or calibrated using data from test subjects), to be further updated or calibrated for an individual patient at a given point in time. This can be simulated out into the future, to identify an "untreated or baseline" condition for the patient, with or without additional simulations that perturb the model according to a given candidate treatment's mechanism, thereby simulating the effect as if untreated or baseline, but also as if treated by specific pharmacologic or device interventions, thereby creating a simulation for likely effect (response) of various specific treatments. Further, the use of outcome data, compiled by machine learned or other predictive models can be coupled with the mentioned per-treatment type simulation to generate personalized patient event-free survival curves.

Specifically, first, as shown in FIG. 6B, there is a development cohort, shown on the left side of the image. For the development cohort, research CTA images and clinical CTA were fed into the modeling software. Tissue measurements made at the first level of processing included structural anatomy and tissue characterization, using tissue modeling software, which were trained using pathologist annotated specimens (noted as "Training CTAs" in FIG. 6B). This generated quantitative plaque morphology data. These data were then fed forward as inputs to the models to elucidate molecular profiles determining plaque phenotype. Once a plaque is profiled and established, the experimental workflow utilizes a set of cases with paired transcriptomic and/or proteomic data from microarrays in a development cohort. These truth data were used to build the virtual transcriptomic and/or proteomic models in the development cohort, then locked down for application to the sequestered test patients as a validation of model capability (noted as "Validation CTAs" in FIG. 6B).

Updating the Initial in Silico Systems Biology Model

The initial model is then updated with calibration data, such as 'omics data, from test subjects to validate and refine the initial model. The calibration data is again based on actual biological samples that show differentially expressed protein and/or transcription levels that are linked to the specific characteristics and morphology of the plaques in each of those test subjects. This update of the initial model provides a calibrated model. This step confirms that the model works as intended and also augments and renders the model more robust, given the data from many test subjects.

Figure 6C:
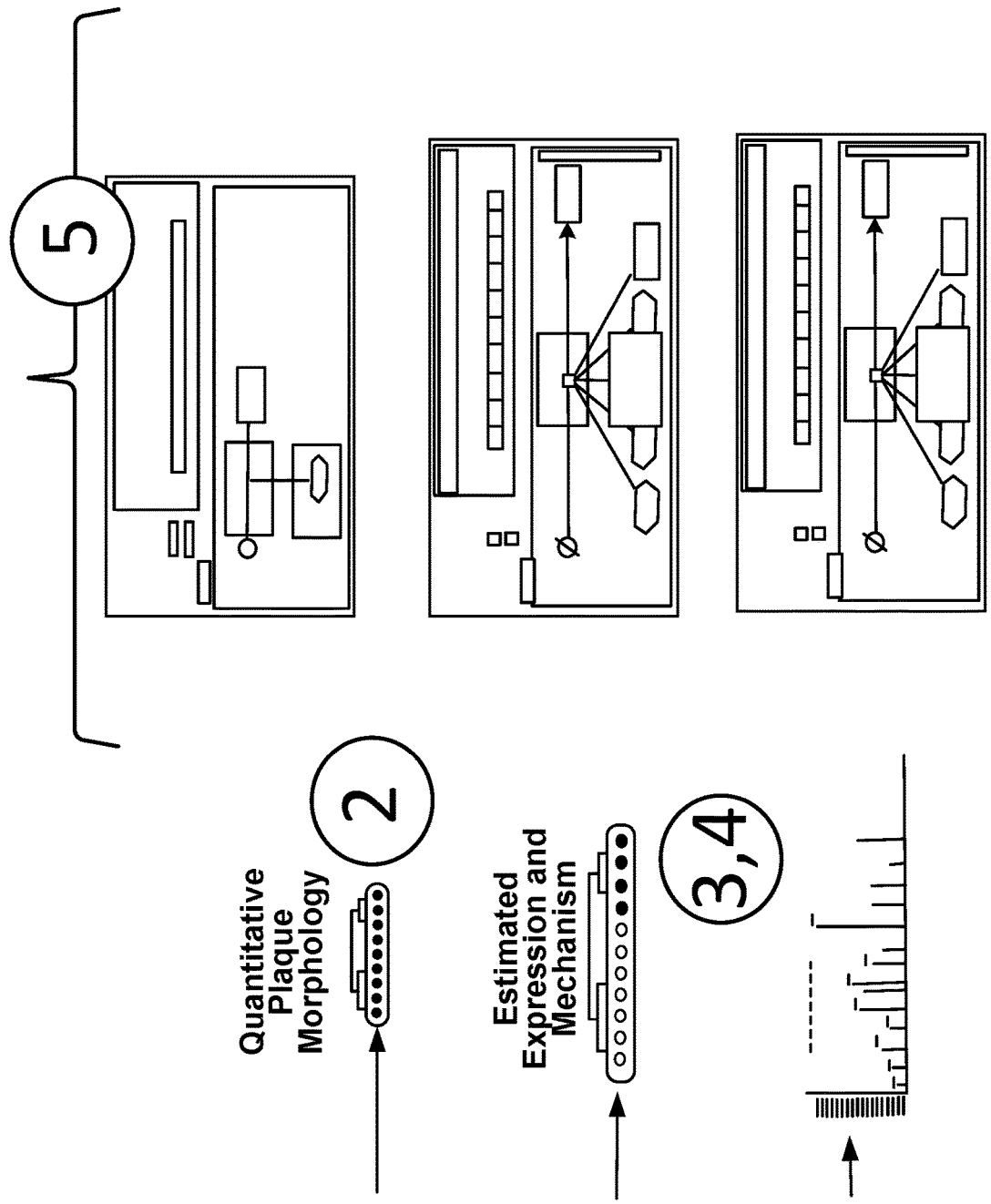

Test data (e.g., from test subjects), are fed forward to obtain information about the plaque morphology as well as to obtain estimated gene and/or protein measurements (see right side of FIG. 6A). This information is then fed into an in silico model, as described below, and the in silico model is calibrated based on the information obtained in FIG. 6B. Specifically, as shown in FIG. 6C, the information about the plaque morphology as well the estimated gene and/or protein measurements obtained in FIG. 6B are fed into the in silico model. Parton et al., New models of atherosclerosis and multi-drug therapeutic interventions. *Bioinformatics* 35, 2449-2457, doi:10.1093/bioinformatics/bty980 (2018)). The reactions (the levels of various molecules) contained in the in silico model are then calibrated. Based on the calibration, the modeling permits the building of biological pathways, which can predict the levels of various molecules within the biological pathways.

More particularly, information obtained from CTA imaging is input into an in silico systems biology model, which is a (set of) network(s) characterizing atherosclerotic cardiovascular disease, where the (each) network includes nodes (each node representing a different protein) and edges between a pair of nodes (each edge representing protein-protein interactions in a given cell type, including "self-edges" as means to represent the transcription/translation process). Each node in the network has information representing a protein level, which can be calibrated based on data (e.g., computed tomography angiograph imaging data of a plaque and proteomics data) from multiple test subjects.

Using the Calibrated In Silico Systems Biology Model

Then in operation, the calibrated model is again updated, but now with patient-specific personalized data based on imaging of the patient's plaque without the need to perform an invasive blood test or biopsy. The calibrated model is also updated with the predicted effects of two or more different therapies. The methods and systems described herein use the patient's imaging data to provide a therapy recommendation based upon an automated comparison of the two or more different therapies whose predicted effects are programmed into the model.

For example, once the initial in silico systems biology model has been calibrated, the biological pathways contained in the in silico systems biology model can then be manipulated based on various drug mechanism of actions and the end outcome of treating a patient with a particular drug can be simulated. Ultimately, a patient's likelihood of survival can also be estimated based on the drug simulations and the system automatically provides a therapy recommendation as described in further detail below.

Figure 7A:
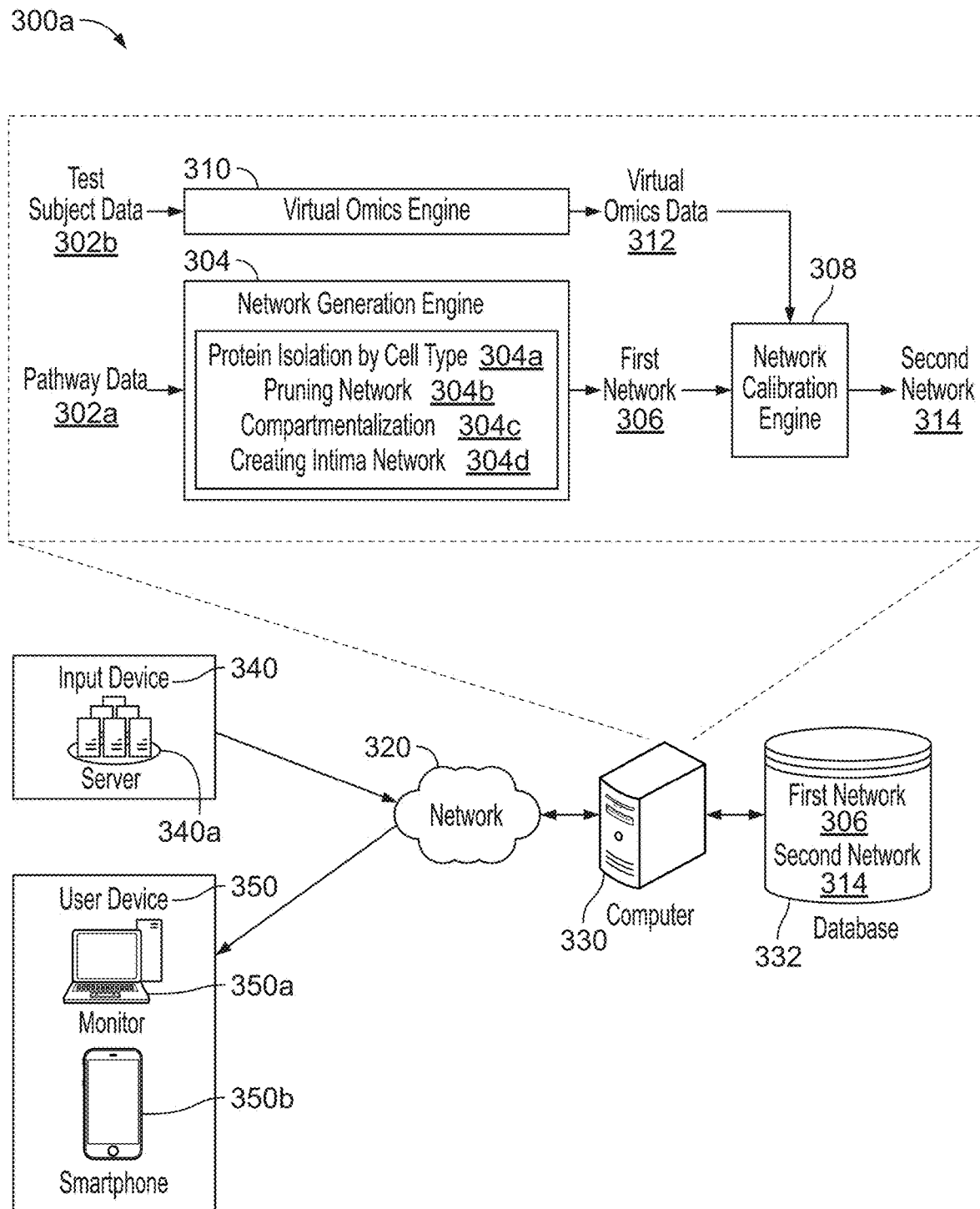
FIG. 7A is a block diagram of an example of a system for generating an in silico systems biology model of atherosclerotic cardiovascular disease.

III. Systems for Generating in Silico Systems Biology Models for Atherosclerosis Given the above, here we disclose one example of a system to generate such a systems biology model. FIG. 7A is a block diagram of an example of a system 300a for generating an in silico systems biology model of atherosclerotic cardiovascular disease. The system 301a includes an input device 340, a network 320, and one or more computers 330 (e.g., one or more local or cloud-based processors). The computer 330 can include a virtual 'omics engine 310, a network generation engine 304, and a network calibration engine 308. In some implementations, the computer 330 is a server. For purposes of the present disclosure, an "engine" can include one or more software modules, one or more hardware modules, or a combination of one or more software modules and one or more hardware modules. In some implementations, one or more computers are dedicated to a particular engine. In some implementations, multiple engines can be installed and running on the same computer or computers.

The input device 340 is configured to obtain pathway data 302a and test subject data 302b and provide the pathway data 302a and the test subject data 302b to another device across a network 320. The pathway data 302a include biological pathways (e.g., pathway names, identifiers) associated with atherosclerotic cardiovascular disease. The test subject data 302b include data (e.g., computed tomography angiograph imaging of a plague, proteomics, transcriptomics) from multiple test subjects who have been diagnosed with atherosclerotic cardiovascular disease. For example, the input device 340 can include a server 340a that is configured to obtain the pathway data 302a from a pathway database. In some implementations, the one or more other input devices can access the test subject data 302b obtained by the server 340a and transmit the obtained test subject data 302b to the computer 330 via the network 320. The network 320 represents a computer network (unlike biological networks such as a first network 306 and a second network 314) and can include one or more of a wired Ethernet network, a wired optical network, a wireless WiFi network, a LAN, a WAN, a Bluetooth network, a cellular network, the Internet, or other suitable network, or any combination thereof.

The computer 330 is configured to obtain the pathway data 302a and the test subject data 302b from the input device 340 and generate an in silico systems biology model of the disease represented by a network. In some implementations, the computer 330 stores the pathway data 302*a* and the test subject data 302*b* in a database 332 and access the database 332 to retrieve desired datasets. The database 332, such as a local database or a cloud-based database, can store the pathway data 302*a*, the test subject data 302*b*, a first network 306, a second network 314, or other suitable data.

In some implementations, the pathway data 302*a* is obtained from differential expression analysis. Each pathway in the pathway data 302*a* includes at least one differentially expressed molecule. For example, the computer 330 obtains first molecular expression data (e.g., gene expression data, protein expression data) of a first set of test subjects who have been diagnosed with the atherosclerotic cardiovascular disease and second molecular expression data of a second set of test subjects who do not have the atherosclerotic cardiovascular disease. Differential expression analysis identifies molecules, e.g., RNA, genes or proteins, that are differentially expressed between these two sets of test subjects. The gene expression data is obtained from microarray, RNA sequencing, single cell RNA sequencing, or reverse transcriptase PCR. Without loss of generality, protein levels can be measured by liquid chromatography mass spectrometry (LC-MS or LS-MS/MS, for example).

The network generation engine 304 is configured to define/train a systems biology model by receiving publicly available and/or experimentally determined data such as pathway data 302*a* and generating a first network 306. The first network 306 (also referred to as an initial or baseline network) characterizes a baseline of the disease, as the network is not yet calibrated using the test subject data 302*b*. In some implementations, the first network 306 is a data structure that represents nodes, edges between nodes, and information (e.g., a protein level) contained in each node. In some implementations, pathway data 302*a* are obtained from findings from scholarly literatures.

Figure 10:
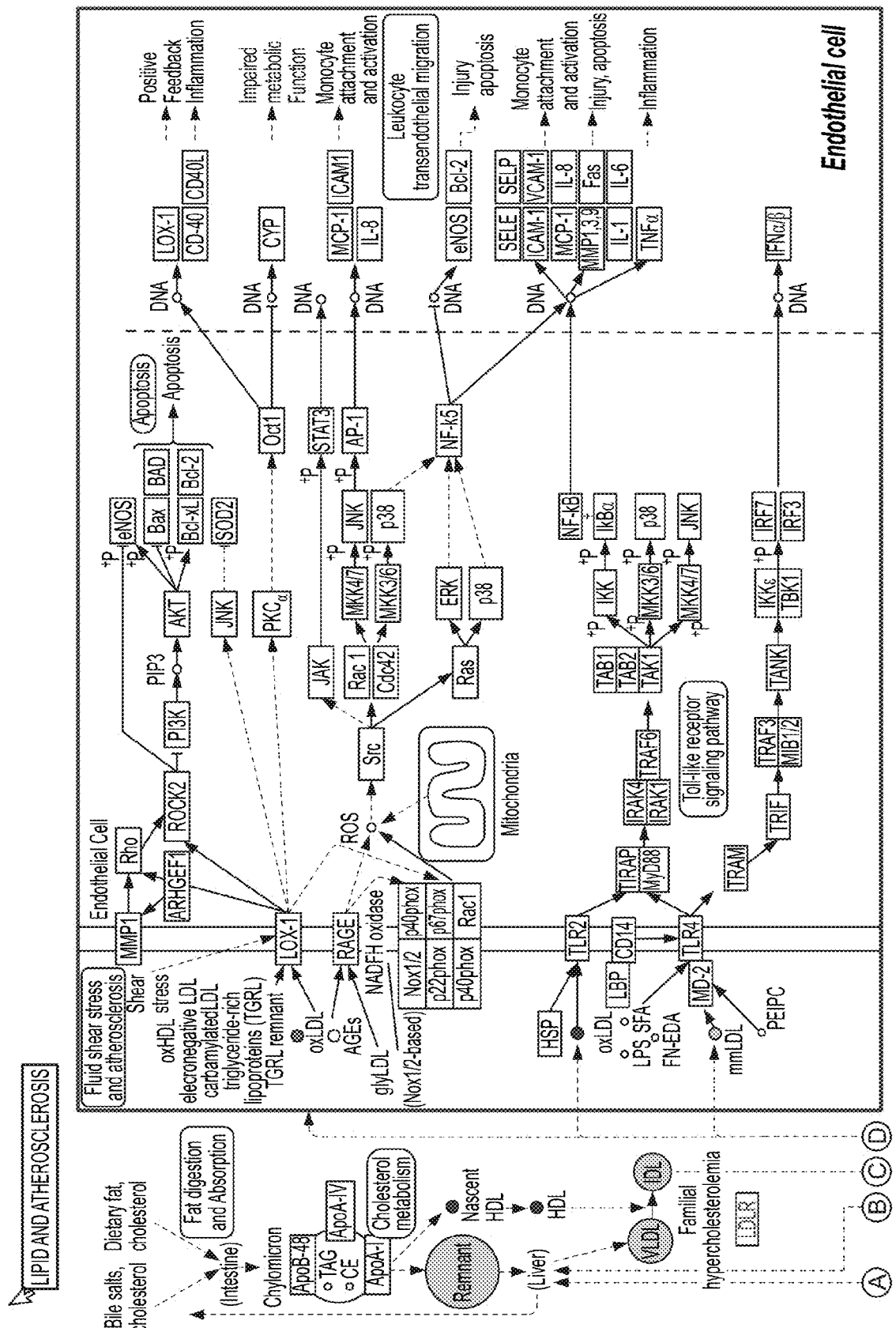
FIG. 10 is a schematic diagram that shows examples of how pathways can be compartmentalized into cell-specific networks, here for an endothelial cell network, a macrophage network, and a vascular smooth muscle cell (VSMC) network. Specific cell types shown are examples, without loss of generality.
Figure 10:
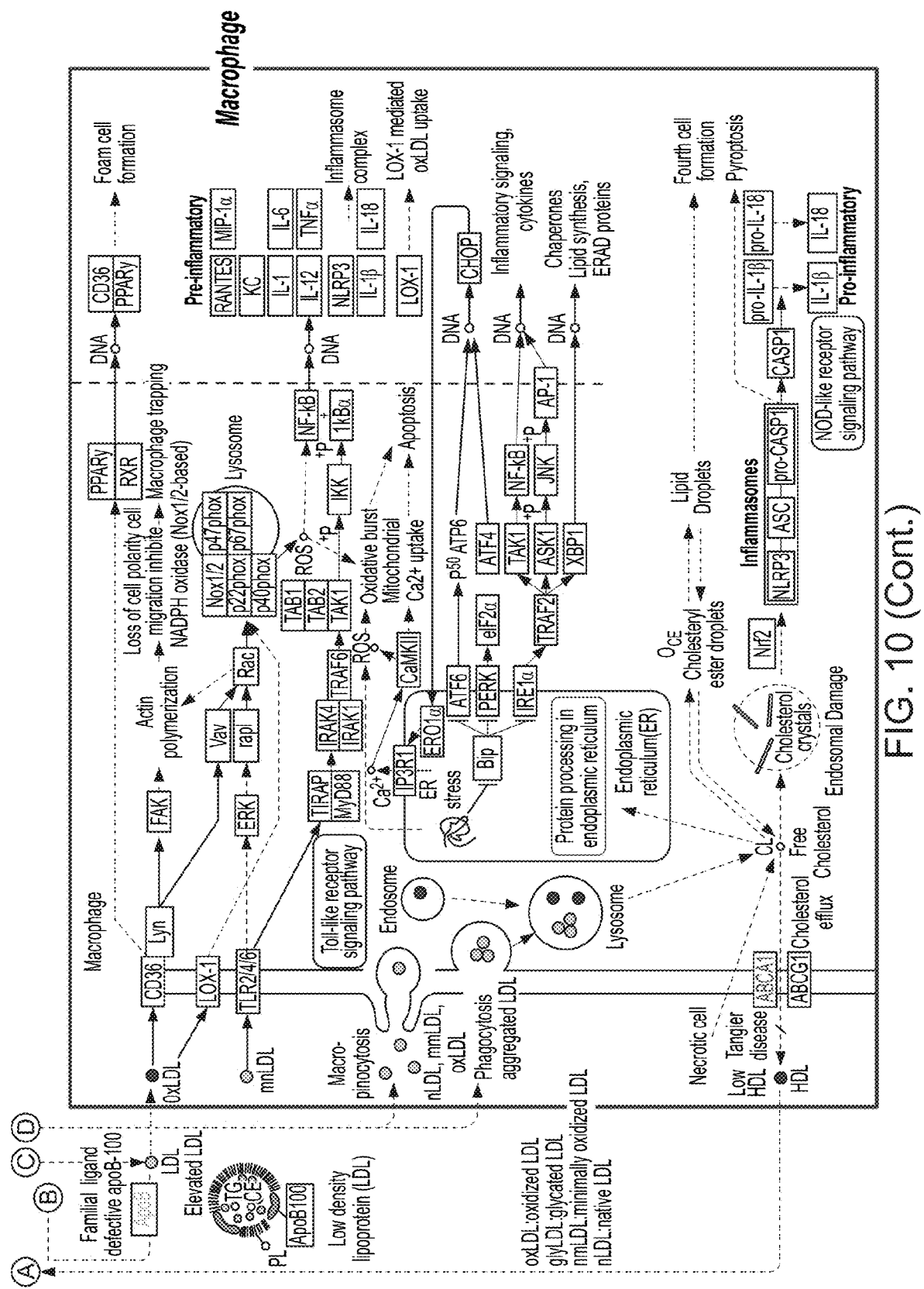
Figure 10:
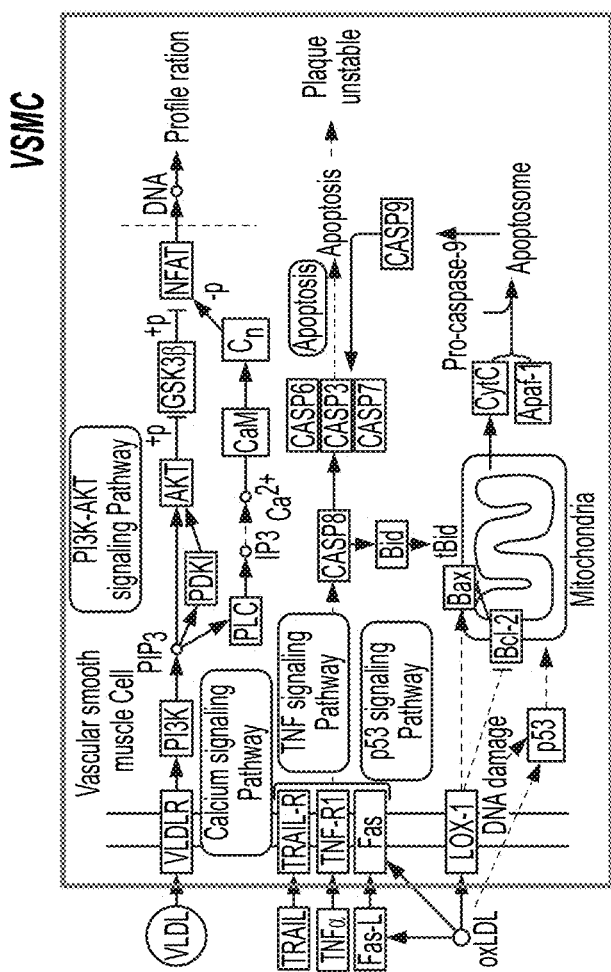

The network generation engine 304 can perform one or more tasks such as protein isolation by cell type 304*a*, pruning network 304*b*, compartmentalization 304*c*, and creating intima network 304*d*. The protein isolation by cell type 304*a* identifies a cell type in which each protein-protein interaction occurs. Referring to FIG. 10, for example, protein-protein interactions in endothelial cells, macrophages, and vascular smooth muscle cells (VSMC) are identified. Pruning network 304*b* removes non-proteins and proteins with missing information.

The compartmentalization 304*c* aims to localize proteins by assigning a compartment to each protein, where the compartment includes an intracellular of each cell type (e.g., intracellular of VSMC), a cell membrane, an extracellular space, and a compartment for blood.

Creating the intima network 304*d* generates an intima network that represents topologically accurate plasma interfaces, as the intima network accounts for topological relationships between compartments. The resulting intima network is referred to as the first network 306. The first network 306 includes baseline levels of proteins. We note that other integrated networks, such as for the adventitia, media, or perivascular space can also be used without loss of generality.

The virtual 'omics engine 310 is configured to receive the test subject data 302*b* and generate virtual 'omics data 312. The test subject data 302*b* include computed tomography angiograph (CTA) imaging data of a plaque from the test subject, plaque morphology data, and proteomics data corresponding to the test subject. As shown in FIG. 6B, molecular measurements such as protein levels (proteomics) and gene expressions (transcriptomics) can be estimated based on a comparison between CTA images used in training the virtual 'omics engine 310 and a patient's CTA image not used in training. The test subject data 302*b* correspond to the data used to train the virtual 'omics engine 310. During training, the virtual 'omics engine 310 identifies features in CTA imaging data (e.g., a particular plaque morphology) that are predictive of the molecular measurements. After training, the virtual 'omics engine 310 is validated, e.g., through a cross-validation scheme or using sequestered test subjects. The virtual 'omics data 312 represent estimated molecular measurements, e.g., transcript or protein levels. When measured molecular measurements are available, the measured protein levels can be used as an input to the network calibration engine 308.

The network calibration engine 308 is configured to receive the first network 306 and the virtual 'omics data 312 and generate a second network 314. The second network 314, updated from the first network 306 using virtual 'omics data 312 derived from the test subject data 302*b*, includes a disease-associated protein level for each protein in the second network. In some implementations, measured 'omics data, in addition to or instead of the virtual 'omics data, are used to update the first network. To update the first network, the network calibration engine 308 first identifies disease-associated protein levels for a set of proteins whose disease-associated protein levels are known from the virtual 'omics data 312. For proteins whose disease-associated protein levels are unknown, the network calibration engine 308 iteratively estimates a disease-associated protein level for a protein based on the protein's adjacent nodes in the first network. After disease-associated protein levels of all proteins in the first network are found (either from the virtual 'omics data 312 or estimation), the network calibration engine 308 outputs the second network 314. The computer 330 can store the second network in the database 332.

The computer 330 can generate rendering data that, when rendered by a device having a display such as a user device 350 (e.g., a computer having a monitor 350*a*, a mobile computing device such as a smart phone 350*b*, or another suitable user device), can cause the device to output data including the first network 306 and the second network 314. Such rendering data can be transmitted by the computer 330 to the user device 350 through the network 320 and processed by the user device 350 or associated processor to generate output data for display on the user device 350. In some implementations, the user device 350 can be coupled to the computer 330. In such instances, the rendered data can be processed by the computer 330 and can cause the computer 330, on a user interface, to output data, e.g., visualizing the second network 314.

Figure 8A:
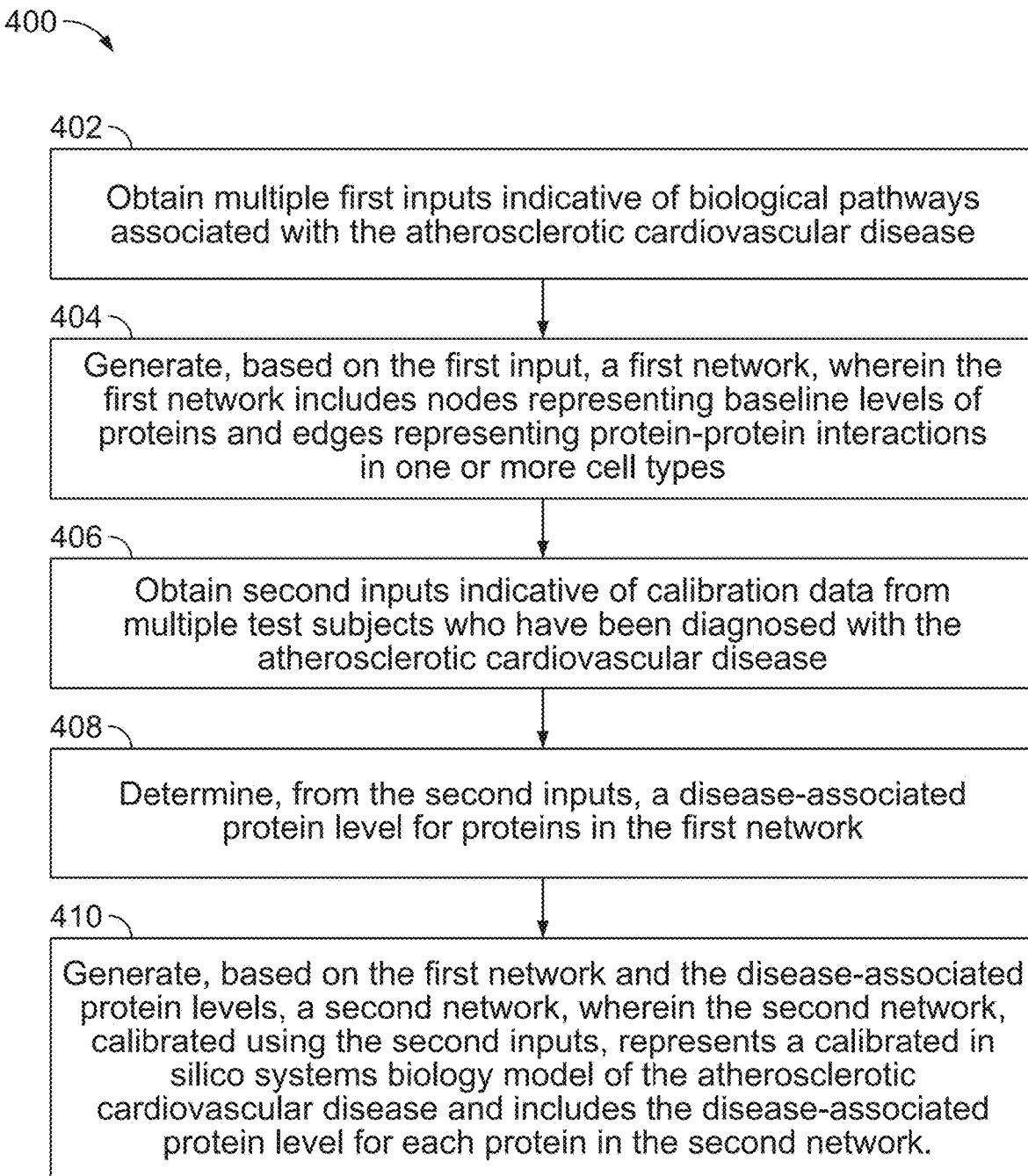
FIG. 8A is a flowchart of an example of a process for generating an in silico systems biology model of atherosclerotic cardiovascular disease.

FIG. 8A is a flowchart of an example of a process 400 for generating a calibrated in silico systems biology model of atherosclerotic cardiovascular disease. The calibrated in silico systems biology model is an updated model from the baseline (initial) model, which is built based on publicly available or otherwise known data such as pathway data, by using 'omics data from test subjects. The process will be described as being performed by a system of one or more computers programmed appropriately in accordance with this specification. For example, the computer 330 of FIG. 3A can perform at least a portion of the example process. In some implementations, various steps of the process 400 can be run in parallel, in combination, in loops, or in any order.

The system obtains multiple first inputs indicative of biological pathways associated with the atherosclerotic cardiovascular disease (402). For example, the system queries a pathway database (e.g., the Kyoto Encyclopedia of Genes and Genomes (KEGG)) to identify biological pathways associated with the atherosclerotic cardiovascular disease. In some implementations, each pathway in the biological pathways includes at least one differentially expressed molecule.

To identify molecules that are differentially expressed, the system obtains first molecular expression data of a first set of test subjects who have been diagnosed with the atherosclerotic cardiovascular disease and second molecular expression data of a second set of test subjects who do not have the atherosclerotic cardiovascular disease. The system performs differential expression analysis on the first and the second molecular expression data and identifies molecules that are differentially expressed. In some implementations, the first and the second molecular expression data are gene expression data. In some implementations, the first and the second molecular expression data are protein expression data.

The system generates, based on the first inputs, a first network (404). The first network includes nodes representing baseline levels of proteins and edges representing protein-protein interactions in one or more cell types. The first network includes proteins, genes, mRNA, nutrients, cellular events, external signals, or combinations thereof found in the biological pathways. The system represents the proteins in the multiple first inputs as the nodes in a graph (also referred to as a state graph), initializes a baseline level for each of the proteins, represents the protein-protein interactions as the edges in the graph, and outputs the graph as the first network. The baseline level indicates a state of the node. The one or more cell types are associated with the atherosclerotic cardiovascular disease. In some implementations, the one or more cell types include cell types that include at least one protein whose level is altered by the atherosclerotic cardiovascular disease. The one or more cell types can include, for example endothelial cells, vascular smooth muscle cells, macrophages, and lymphocytes. Other cell types can be included without loss of generality.

In some implementations, each of the edges in the first network is directed with a weight, where directed edges indicate a direction of the protein-protein interaction, e.g., a molecule A activating a molecule B. The weight can indicate a type of the protein-protein interaction, e.g., activation, inhibition, dissociation, methylation, glycosylation, translation, repression, degradation, etc. The weight is positive for activation and translation. The weight is negative for inhibition, repression, and degradation. The edges in the first network can have information indicative of a dependency condition: a molecule A interacts with a molecule B under a certain condition, e.g., the baseline level of the molecule B meets a threshold. The first network can be displayed in a graphical form on a user interface, e.g., using cytoscape.

The first network includes (i) a "core network" representing protein-protein interactions unique to each respective cell type, (ii) a "mid network" representing protein-protein interactions that occur in multiple cell types, but not all cell types, and (iii) a "full network" representing protein-protein interactions that occur in all cell types. The edges represent protein-protein interactions representing any one of different types of interactions including, for example, activation, inhibition, indirect effect, state change, binding, dissociation, phosphorylation, dephosphorylation, glycosylation, ubiquitination, and/or methylation.

The system can separately calibrate the core network, the mid network, and the full network by using the second inputs to generate a calibrated sub-network. After calibration, the system generates the second network that includes the calibrated sub-networks. In particular, the protein-protein interaction of an $i^{th}$ molecule with a $j^{th}$ molecule is represented as $\Sigma_j w(j, i) * s_j(t-d(j, i))$, wherein $w(j, i)$ is a weight of the edge between the $i^{th}$ molecule and the $j^{th}$ molecule, $s_j$ is a baseline level of the $j^{th}$ molecule, t is a time step, and $d(j, i)$ is a delay of the edge between the $i^{th}$ molecule and the $j^{th}$ molecule. The delay of the edge indicates the time step required for the protein-protein interaction to be effected.

The system obtains second inputs indicative of calibration data from multiple test subjects who have been diagnosed with the atherosclerotic cardiovascular disease (406). The second inputs include non-invasively obtained data, such as imaging data, for each test subject, of a plaque from the test subject, morphology data obtained from the plaque, and proteomics data corresponding to the plaque.

The imaging data can be obtained by computed tomography (CT), dual energy computed tomography (DECT), spectral computed tomography (spectral CT), computed tomography angiography (CTA), cardiac computed tomography angiography (CCTA), magnetic resonance imaging (MM), multi-contrast magnetic resonance imaging (multi-contrast MRI), ultrasound (US), positron emission tomography (PET), intra-vascular ultrasound (IVUS), optical coherence tomography (OCT), near-infrared radiation spectroscopy (NIRS), or single-photon emission tomography (SPECT) diagnostic images or any combination thereof.

In case that the proteomics data are not available, or in addition to the proteomics data, the system can obtain transcriptomics data. In some implementations, the system obtains, for at least some of the test subjects, transcriptomics data. The transcriptomics data is obtained by microarray, RNA sequencing (RNA-seq), single cell RNA sequencing (scRNA-seq), reverse transcriptase PCR (RT-PCR), or any combination thereof. In some implementations, the system obtains, for at least some of the test subjects, proteomics data, e.g., protein levels obtained from protein mass spectrometry. In some implementations, the system obtains, for at least some of the test subjects, liquid chromatography-mass spectrometry data of various molecules.

For the case where 'omics data are obtained, the first network includes nodes representing baseline levels of proteins and genes, and edges representing protein-protein interactions, gene-gene interactions, and protein-gene interactions in the one or more cell types.

The system determines, from the second inputs, a disease-associated protein level for proteins in the first network (408). The disease-associated protein level of a specific protein corresponds to one or more of a measured protein level from tissue samples from the test subjects, an estimated protein level based on one or more virtual 'omics models of the test subjects, or a protein level corresponding to non-invasively obtained imaging data from the test subjects. In different embodiments, the specific proteins can be one or more of lipopolysaccharide-binding protein (LBP), integrin subunit alpha 2b (ITGA2B), toll like receptor 4 (TLR4), lipocalin 2 (LCN2), S100 calcium binding protein A8 (S100A8), S100 calcium binding protein A9 (S100A9), cyclin dependent kinase inhibitor 1A (CDKN1A), matrix metallopeptidase 1 (MMP1), receptor for advanced glycation end products (RAGE), heme oxygenase 1 (HMOX1), SMAD family member 2 (SMAD2), and coagulation factor VIII (F8). Many other molecular species are utilized by the invention, without loss of generality; these are given by way of example rather than being considered definitive or limiting.

The system identifies disease-associated protein levels for a set of proteins from the second inputs, where the disease-associated protein levels of the set of proteins are obtained from the second inputs from the test subjects. The system estimates, for proteins in the first network other than the set of proteins, a disease-associated protein level based on the disease-associated protein levels of a subset of the set of proteins, where the subset of the set of proteins are represented by adjacent nodes in the first network.

The system generates, based on the first network and the disease-associated protein levels, a second network (410). The second network, an updated network from the first network using the second inputs, represents a calibrated in silico systems biology model of the atherosclerotic cardiovascular disease and includes the disease-associated protein level for each protein in the second network. To generate the second network, the system identifies a disease-associated protein level for each node whose disease-associated protein level is obtained from the calibration data from the test subjects; and identifies a disease-associated protein level for each node whose disease-associated protein level is estimated.

IV. Methods and Systems for Predicting Suitable Therapeutic/Treatment Plans for Specific Patients In general, various therapies, e.g., pharmacotherapies and/or procedural interventions, can be used for the treatment of cardiovascular diseases, such as atherosclerosis. The in silico systems biology models described herein can simulate how an actual patient will react to a particular therapy (i.e., will the therapy have a beneficial effect, and if so, to what extent) based on the mechanism of action of that specific pharmacotherapy. Provided below are examples of embodiments of how personalized therapeutic treatment plans can be simulated in the in silico systems biology model described herein by manipulating/physically changing the levels of certain molecules, e.g., RNA, DNA, or all or parts of genes or proteins, in the models based on the mechanism of action of the therapy, e.g., pharmacotherapy. Accordingly, this disclosure provides methods of simulating a therapeutic response in an actual patient by modulating levels of specific gene transcripts and/or protein levels in the in silico systems biology models described herein.

Figure 7B:
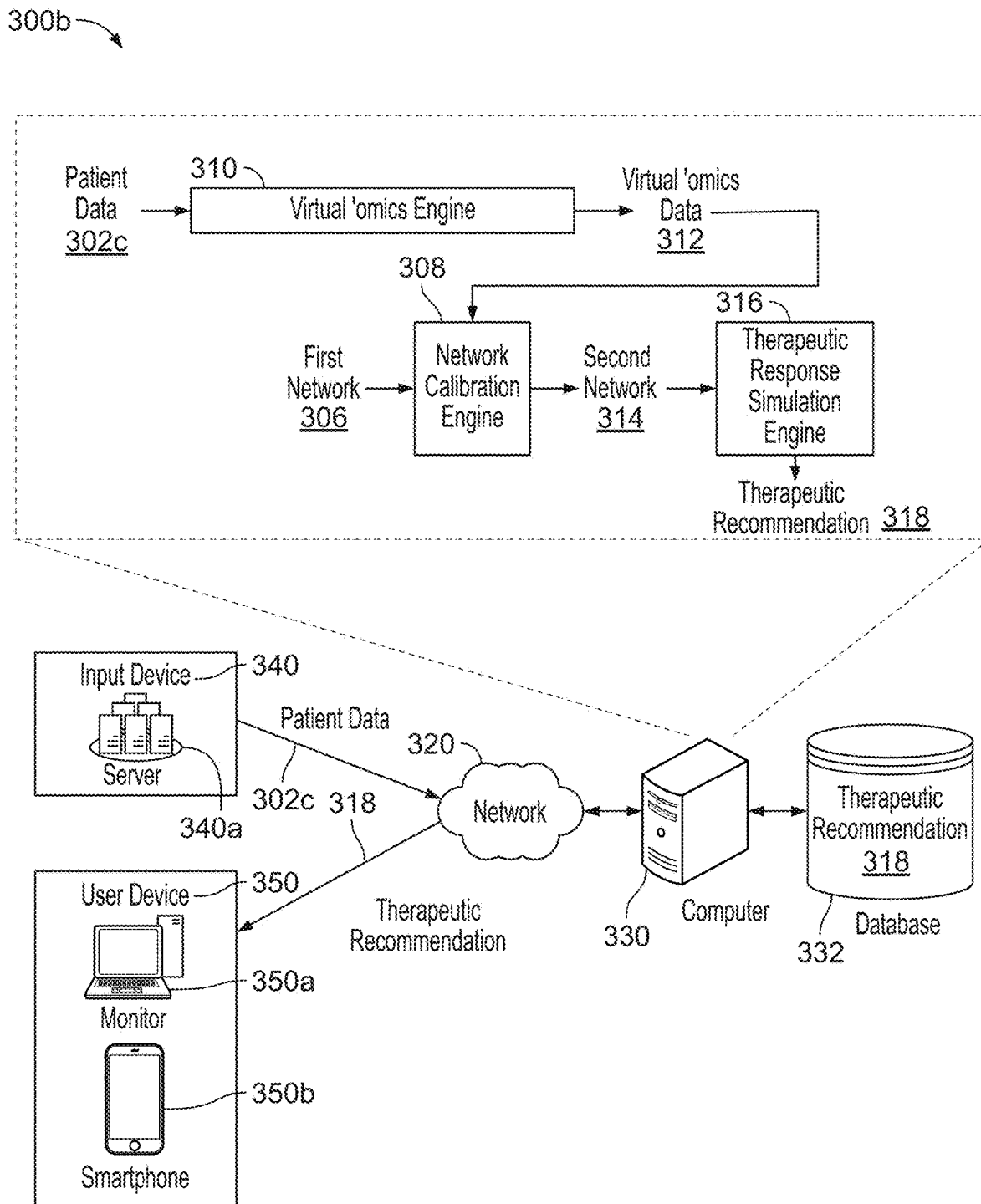
FIG. 7B is a block diagram of an example of a system for providing a therapeutic recommendation based on the in silico systems biology model.

FIG. 7B is a block diagram of an example of a system 300b for providing a therapeutic recommendation for a patient with known or suspected atherosclerotic cardiovascular disease, based on the in silico systems biology model. The system 300b includes an input device 340, a network 320, and one or more computers 330. The computer 330 can include a virtual 'omics engine 310, a network calibration engine 308, and a therapeutic response simulation engine 316. Engines not described referring to FIG. 7A are described here.

The virtual 'omics engine 310 in FIG. 7B that has been trained on the test subject data 302b is configured to receive patient data 302c and generate virtual 'omics data 312. The patient data 302c includes a computed tomography angiograph (CTA) imaging dataset for an atherosclerotic plaque from the patient. Based on comparing the patient data 302c and the test subject data 302b, the virtual 'omics engine 310 predicts the levels of certain molecules (e.g., protein levels).

The network calibration engine is configured to receive the virtual 'omics data 312 (e.g., predicted protein levels of the patient, based on the CTA imaging dataset) and the first network 306 and generate a second network 314. The first network 306 is a trained in silico systems biology model of atherosclerotic cardiovascular disease, as described referring to FIG. 7A. The molecule levels in the first network 306 are updated based on the multiple test subject, but not to a particular patient yet. The network calibration engine 308 aims to update, for a given patient, the first network 306 to generate a patient-specific network, the second network 314. To generate the second network 314, the network calibration engine 308 updates the molecule levels in the first network 306 based on the virtual 'omics data 312; the updated molecule levels are referred to as personalized molecule levels. For molecules with missing virtual 'omics data (that is, molecules whose levels are not predicted by the virtual 'omics engine 310), the network calibration engine 308 estimates a personalized molecule level based on the personalized molecule levels of adjacent nodes in the first network. In some implementations, the network calibration engine 308 removes molecules whose molecule levels cannot be estimated.

The therapeutic response simulation engine 316 simulates a therapeutic response for each potential therapy in the second network, the trained in silico systems biology model calibrated for a given patient. The therapeutic response simulation engine 316 determines a known set of molecules affected by the potential therapy, e.g., based on published scientific discoveries pertaining to mechanism of action and defines one or more therapeutic effect molecule level for each molecule in the known set of molecules (e.g., proteins, genes), e.g., based on known mechanisms of action of the potential therapy. The therapeutic response simulation engine 316 estimates a therapeutic effect molecule level based on a simulated effect of the defined therapeutic effect molecule levels and compares the defined and estimated therapeutic effect molecule levels in the second network, before and after the therapeutic response simulation for each potential therapy. As an output of the therapeutic response simulation engine 316, a therapeutic recommendation 318, a report indicating the preferred therapy for the patient, is generated. The therapeutic recommendation 318 is sent to the user device 350, e.g., the monitor 350a and the smartphone 350b. The therapeutic recommendation 318 can be stored in the database 332, for the computer 330 to access to retrieve.

Figure 8B:
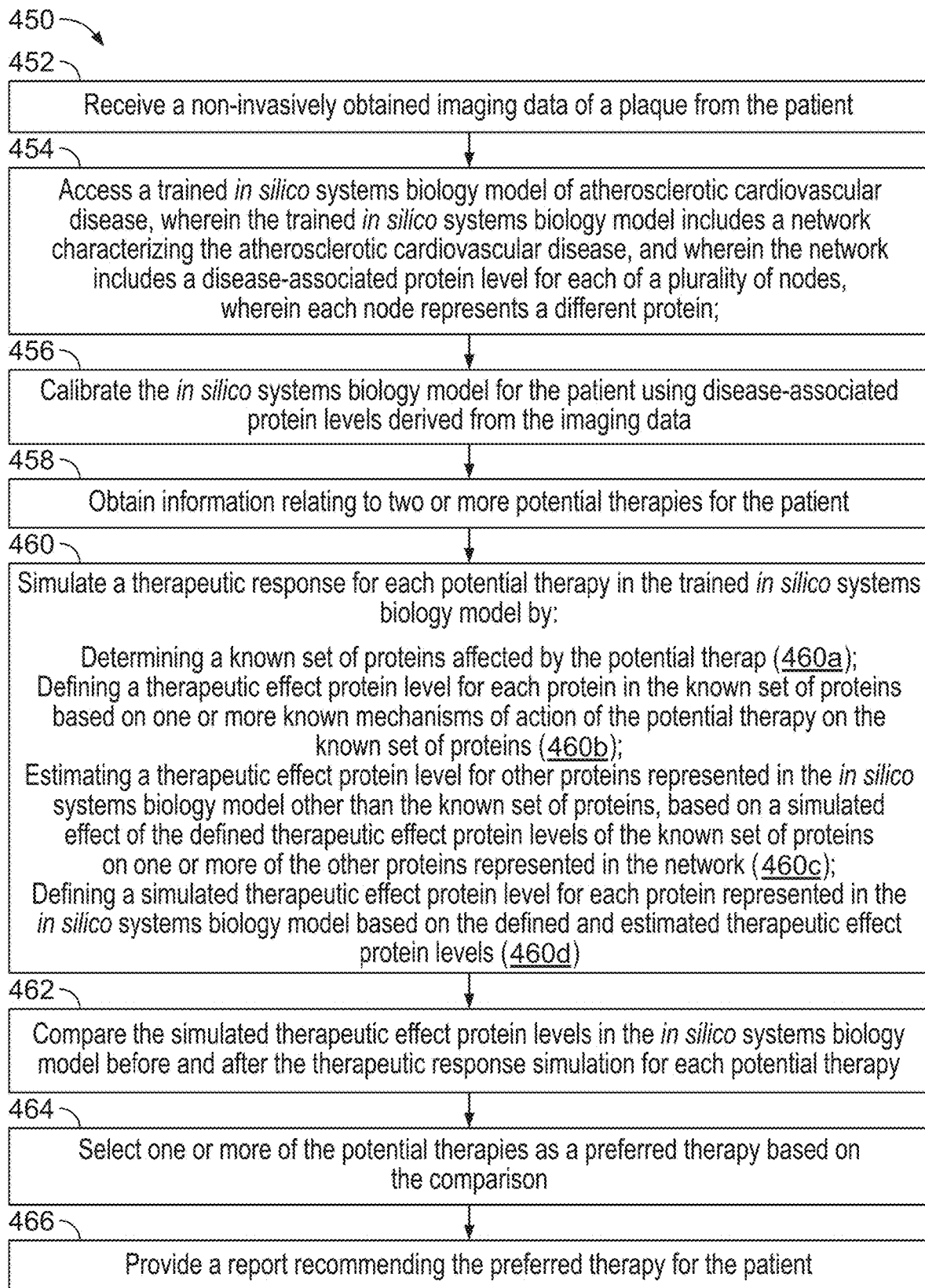
FIG. 8B is a flowchart of an example of a process for providing a therapeutic recommendation based on the in silico systems biology model.

FIG. 8B is a flowchart of example of a process 450 for providing a therapeutic recommendation for a patient with known or suspected atherosclerotic cardiovascular disease. The process will be described as being performed by a system of one or more computers programmed appropriately in accordance with this specification. For example, the computer 330 of FIG. 7B can perform at least a portion of the exemplary process. In some implementations, various steps of the process 450 can be run in parallel, in combination, in loops, or in any order.

The system receives a non-invasively obtained imaging data of a plaque from the patient (452). The non-invasively obtained imaging data is obtained by computed tomography (CT), dual energy computed tomography (DECT), spectral computed tomography (spectral CT), computed tomography angiography (CTA), cardiac computed tomography angiography (CCTA), magnetic resonance imaging (MM), multi-contrast magnetic resonance imaging (multi-contrast MRI), ultrasound (US), positron emission tomography (PET), intra-vascular ultrasound (IVUS), optical coherence tomography (OCT), near-infrared radiation spectroscopy (NIRS), or single-photon emission tomography (SPECT) diagnostic images or any combination thereof.

The system accesses a trained in silico systems biology model of cardiovascular disease (454). The trained in silico systems biology model includes a network characterizing the cardiovascular disease. The network includes a disease-associated molecule level for each of a plurality of nodes, wherein each node represents a different molecule, e.g., protein or gene or nucleic acid. In some implementations, the network includes proteins, and disease molecule levels represent disease-associated protein levels for proteins and disease-associated gene levels for genes. The network includes protein-protein interactions in one or more cell types including endothelial cells, vascular smooth muscle cells, macrophages, and lymphocytes. These cell types, in some implementations, are cell types that include at least one molecule whose level is altered by the cardiovascular disease. In some implementations, the trained in silico systems biology model is a baseline model built using the publicly available or otherwise known data. In some implementations, the trained in silico systems biology model is an updated model, from the baseline model, using calibration data from test subjects, as described herein.

The system updates the in silico systems biology model for the patient using personalized molecule levels derived from the non-invasively obtained data, e.g., imaging data (456). The system compares the imaging data of the patient with imaging data of multiple test subjects, where the imaging data of multiple test subjects were an input to update the in silico systems biology model. Based on the comparison, the system predicts personalized molecule levels for molecules in the network.

The system obtains information relating to two or more potential therapies for the patient, or compares one potential therapy against baseline levels (458). The potential therapies can include, for example, (i) a lipid lowering drug, (ii) an antidiabetic drug, (iii) an anti-inflammatory treatment, and (iv) any combination of (i)-(iii). For example, the system receives an identifier of the potential therapies.

For example, the lipid-lowering drug can be any one or more of a statin, a proprotein convertase subtilisin kexin type 9 (PCSK9) inhibitor, or a cholesteryl ester transfer protein (CETP). The antidiabetic drug can include, for example, metformin. The anti-inflammatory treatment can include, for example, anti-IL1β, anti-TNF, anti-IL 12/23, and anti-IL17 agents. These treatments are provided as examples without loss of generality.

The system simulates a therapeutic response for each potential therapy in the trained in silico systems biology model (460) by following sub processes. The system determines a known set of molecules affected by the potential therapy (460a). The system defines a therapeutic effect molecule level for each molecule in the known set of molecules based on one or more known mechanisms of action of the potential therapy on the known set of molecules (460b). To define the therapeutic effect level, the system sets therapeutic effect molecule levels of the set of proteins to a baseline level. The baseline level, in some implementations, is determined based on observed level of molecules from subjects or patients without disease, or a baseline can be developed for subjects or patients already on some form of pharmacotherapy where the simulation would be considered additive to that baseline therapy.

The system estimates a therapeutic effect level for other molecules represented in the in silico systems biology model other than the set of known molecules, based on a simulated effect of the defined therapeutic effect levels of the set of known molecules, e.g., proteins, on one or more of the other molecules represented in the network (460c). The system defines a simulated therapeutic effect level for each molecule represented in the in silico systems biology model based on the defined and estimated therapeutic effect levels (460d). In the cases where the molecule is a protein, a therapeutic effect level is a therapeutic effect protein level. When the molecule is a gene, a therapeutic effect molecule level is a therapeutic effect gene level.

The system compares the simulated therapeutic effect levels in the in silico systems biology model before and after the therapeutic response simulation for each potential therapy (462).

The system selects one or more of the potential therapies as a preferred therapy based on the comparison (464).

Figure 25A:
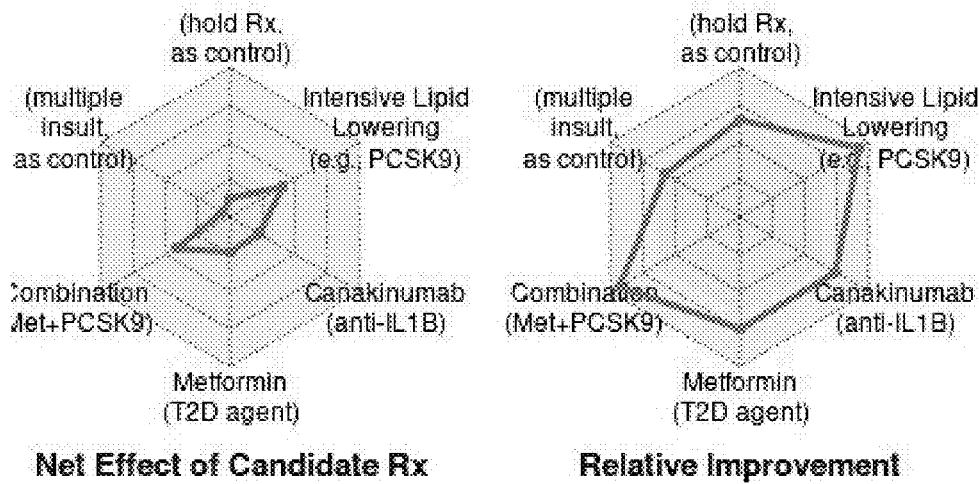
FIGS. 25A-25C are personalized subject treatment recommendations for three patients based on actual data.
Figure 25A:
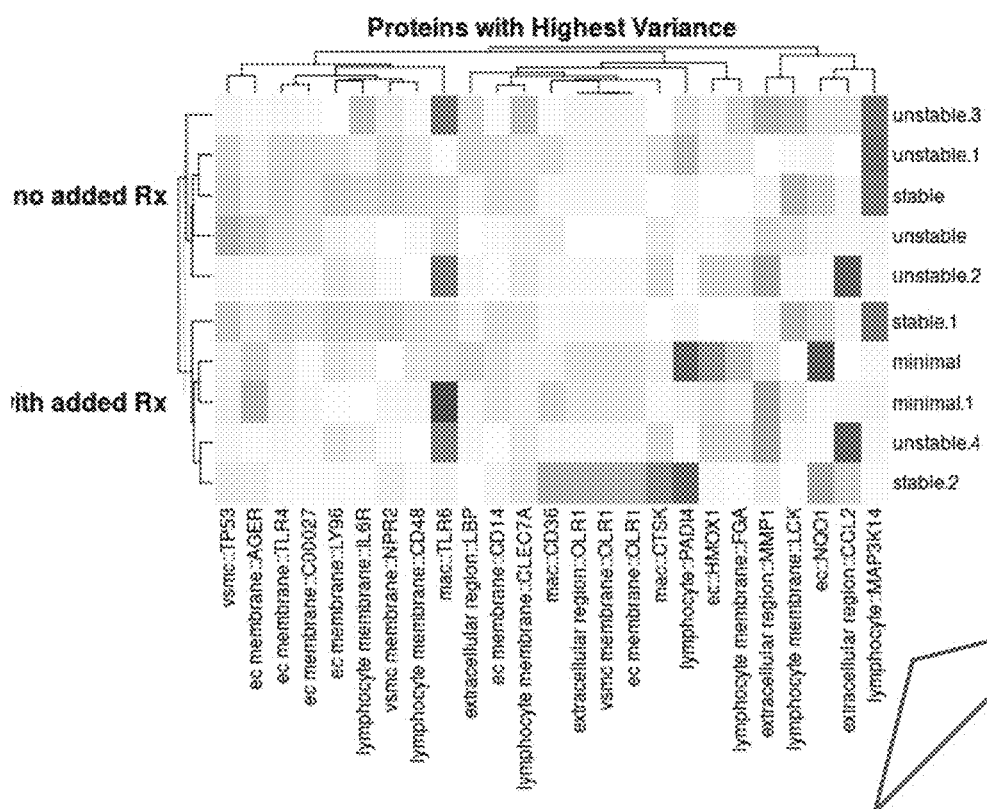
Figure 25B:
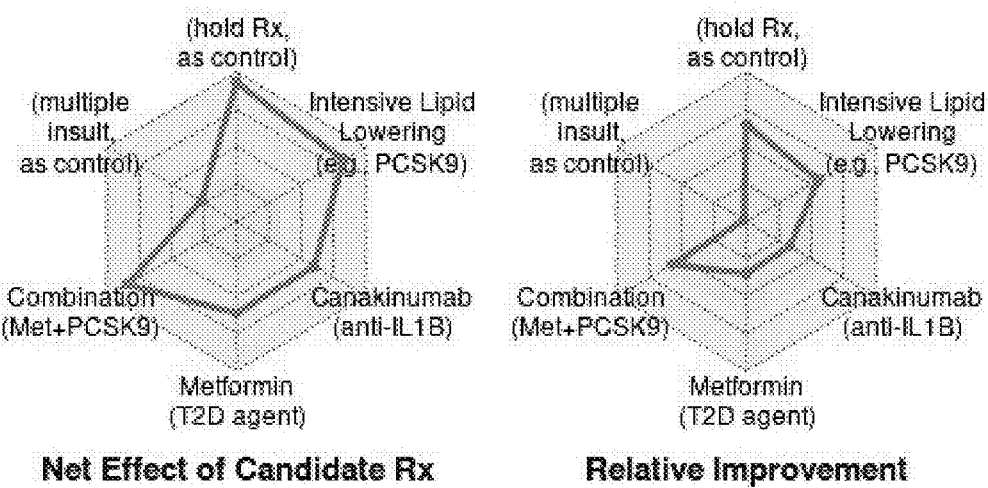
Figure 25B:
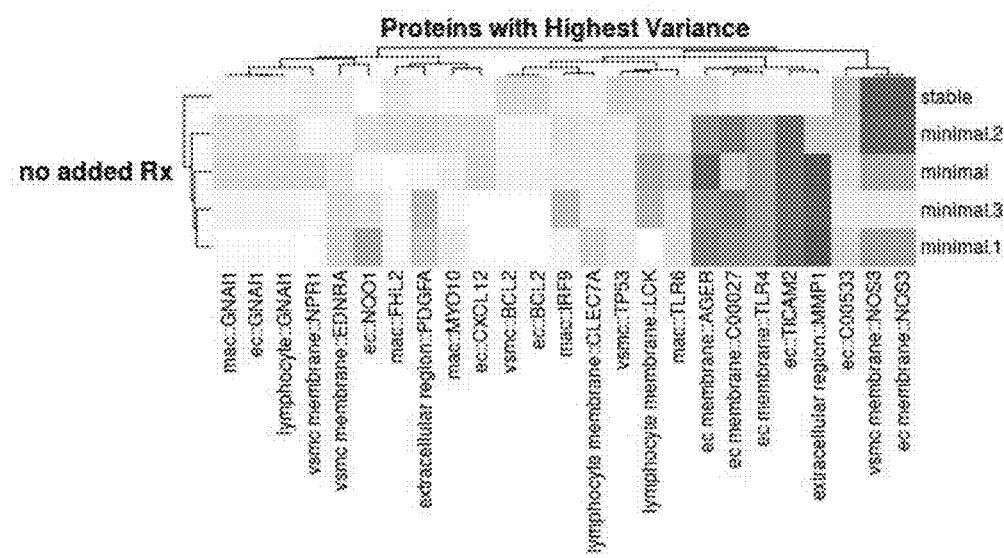
Figure 25C:
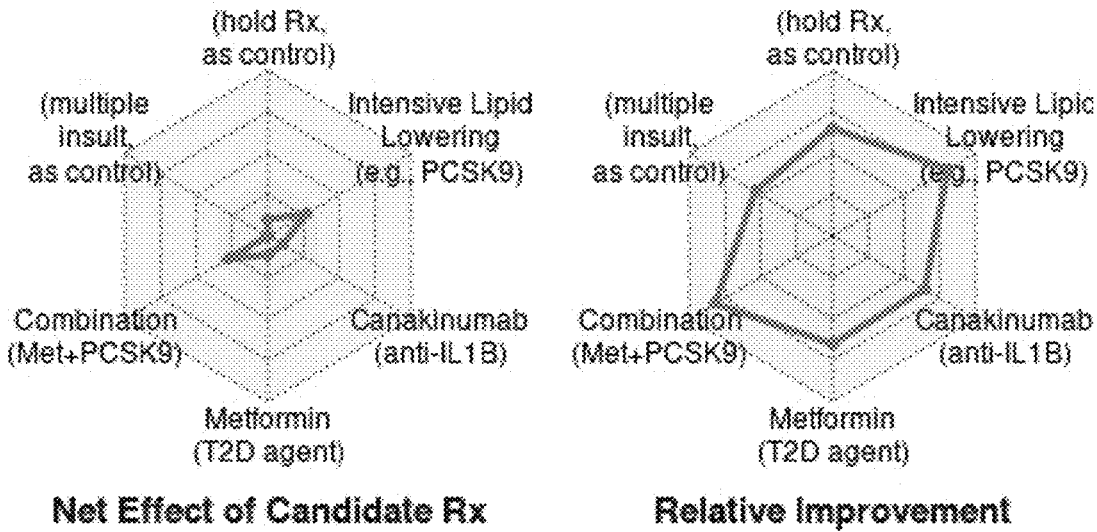
Figure 25C:
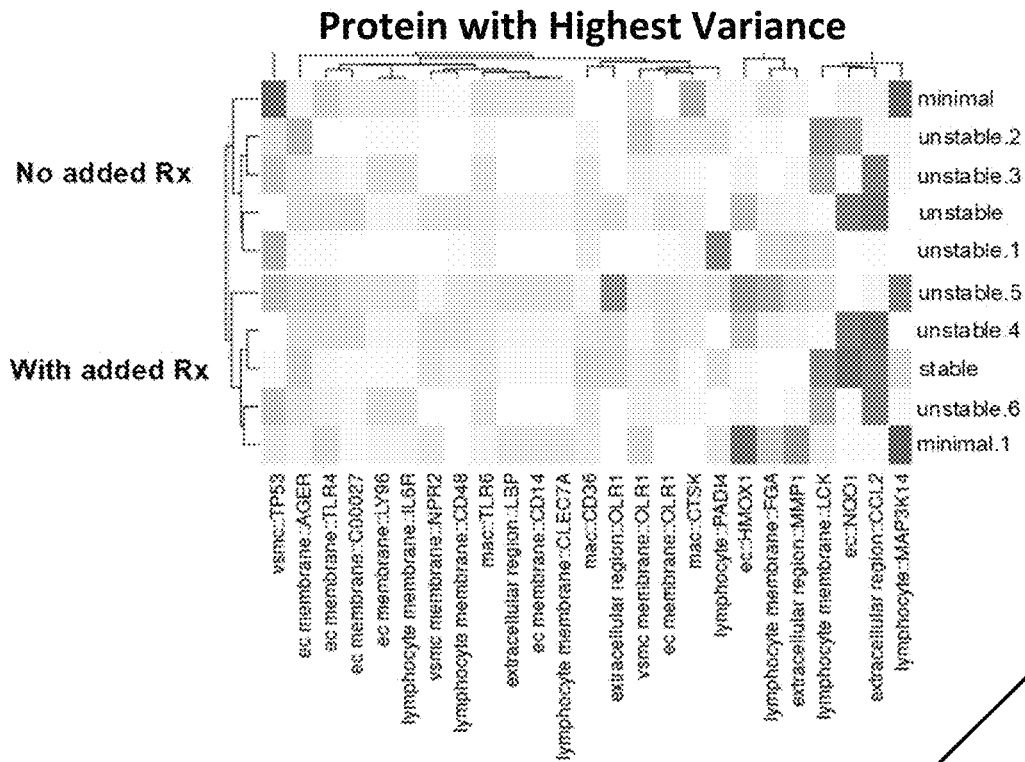

The system provides a report recommending the preferred therapy for the patient (466). The report includes predicted effectiveness of potential therapies and change in therapeutic effect molecule levels before and after the therapeutic response simulation for the preferred therapy. The report, as shown in FIGS. 25A-25C, can be visualized on a user interface. In some embodiments, the system compares a therapeutic effect level before and after the therapeutic response simulation for only one specific therapy, to determine whether that therapy has a beneficial effect for a specific patient, and if so, to what extent. This process is completed for each of the potential therapies, and then the extent of their respective beneficial effects, if any, are compared to select the best therapy for the specific patient.

Figure 8C:
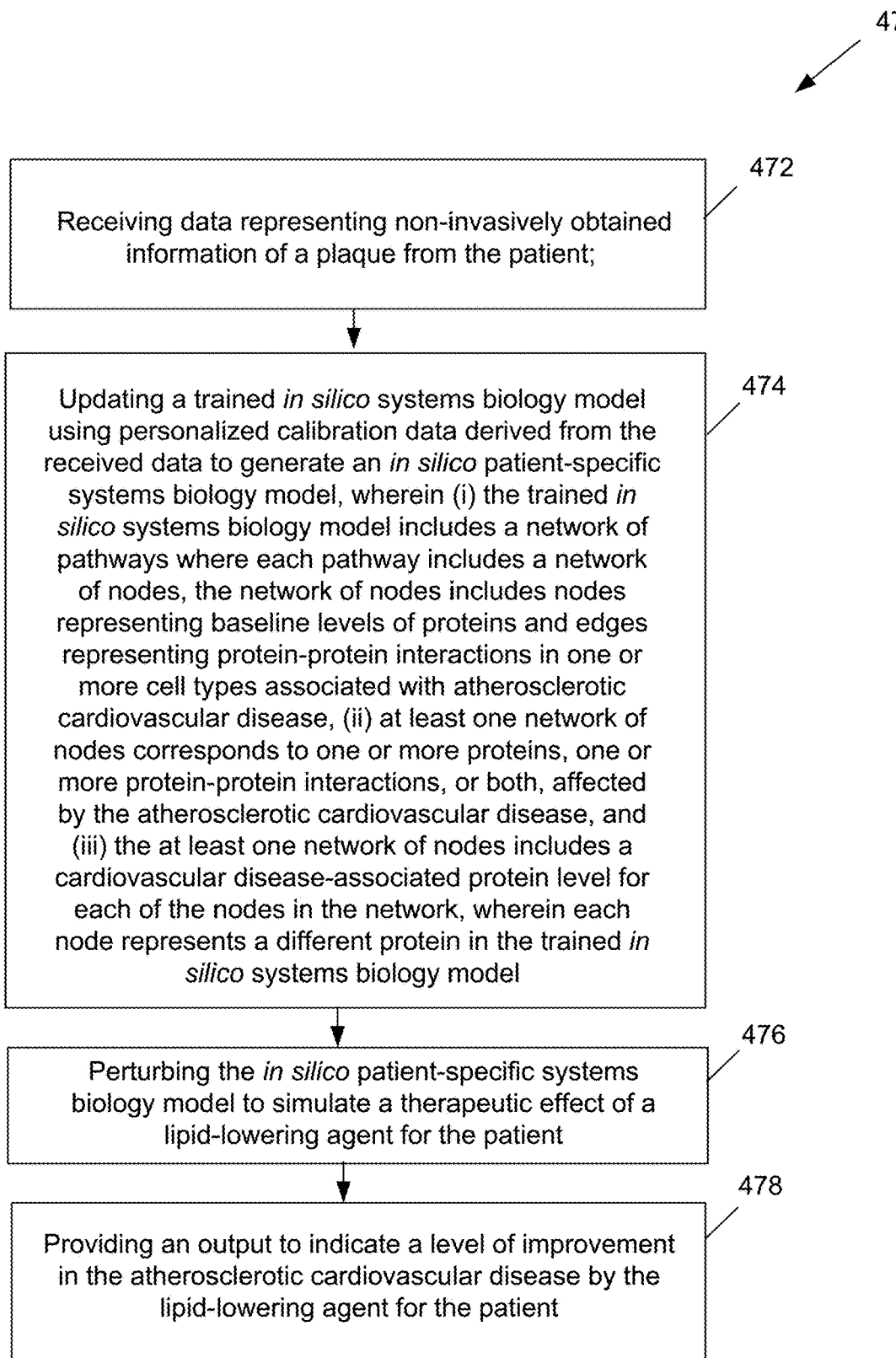
FIG. 8C is a flowchart of an example of a process for providing a therapeutic recommendation based on the in silico systems biology model.

FIG. 8C presents another implementation for providing a therapy recommendation. In particular, a flowchart of an example of a process 470 for clinical decision support is presented. The process is described as being performed by a system of one or more computing devices programmed appropriately in accordance with this disclosure. For example, the computer 330 of FIG. 7B can perform at least a portion of the process. In some implementations, various steps of the process 470 can be run in parallel, in combination, in loops, or in any order.

Operations of the system includes receiving non-invasively obtained data related to a plaque from a patient (472). For example, imaging data can be received by the system. Operations also include updating a trained in silico systems biology model using personalized calibration data derived from the received data to generate an in silico patient-specific systems biology model (474). The trained in silico systems biology model comprises a set of networks, wherein each network comprises a plurality of nodes, each node representing a baseline level of a molecule, and a plurality of edges between pairs of nodes, each edge representing a molecule-molecule interaction. At least two of the nodes represent molecules whose levels are affected by the atherosclerotic cardiovascular disease. At least one of the set of networks includes a disease-associated molecule level for each of the nodes in the network. In one implementation, the at least set of networks includes of nodes corresponding, respectively, to one or more of, for example, a glycosylated low-density lipoprotein (glyLDL), an oxidized LDL (oxLDL), a minimally-modified LDL (mmLDL), or a very-low-density lipoprotein (VLDL). Operations of the system with such nodes also include perturbing the in silico patient-specific systems biology model to simulate a therapeutic effect of, for example, a lipid-lowering agent for the patient (476). Operations of the system that has such a perturbation also include providing an output indicating a level of improvement in the atherosclerotic cardiovascular disease by the exemplary lipid-lowering agent for the patient and a recommendation supporting a clinical decision as to whether the exemplary lipid-lowering agent would benefit the patient (478).

Figure 9:
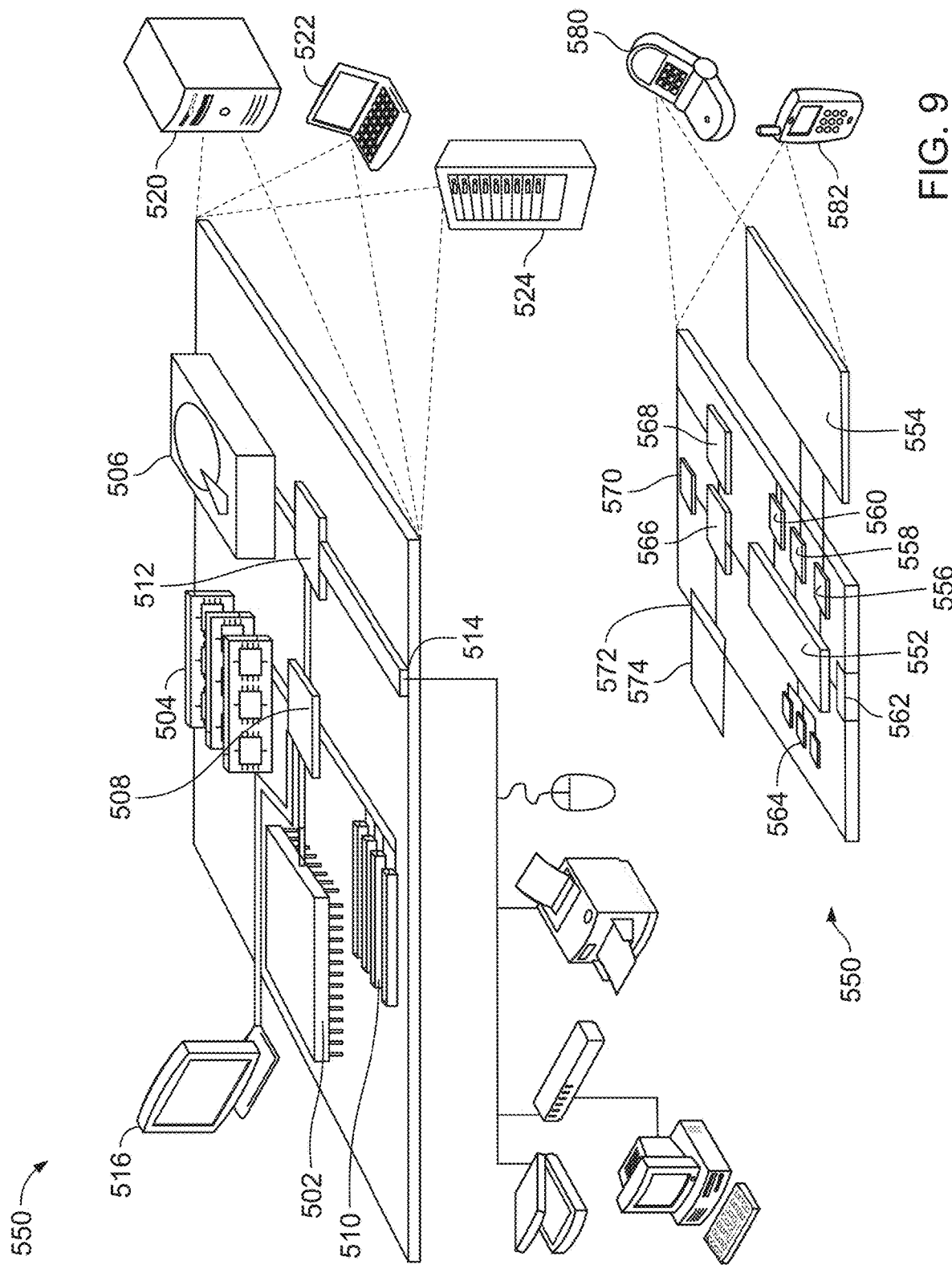
FIG. 9 is a schematic diagram of an example of system components that can be used to implement systems and methods.

FIG. 9 illustrates an example of a block diagram of system components that can be used to implement systems and methods described herein. FIG. 9 shows a computing device 500 that represents any one or more of various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smartphones, and other similar computing devices. Additionally, computing device 500 or 550 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be exemplary only, and are not meant to limit implementations of the inventions described and/or claimed in this document.

Computing device 500 includes a processor 502, memory 504, a storage device 506, a high-speed controller 508 connecting to memory 504 and high-speed expansion ports 510, and a low speed controller 512 connecting to low speed bus 514 and storage device 506. Each of the components 502, 504, 508, 508, 510, and 512, are interconnected using various busses, and can be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed controller 508. In other implementations, multiple processors and/or multiple buses can be used, as appropriate, along with multiple memories and types of memory. Also, multiple computing devices 500 can be connected, with each device providing portions of the necessary operations, e.g., as a server bank, a group of blade servers, or a multi-processor system.

The memory 504 stores information within the computing device 500. In one implementation, the memory 504 is a volatile memory unit or units. In another implementation, the memory 504 is a non-volatile memory unit or units. The memory 504 can also be another form of computer-readable medium, such as a magnetic or optical disk.

The storage device 506 is capable of providing mass storage for the computing device 500. In one implementation, the storage device 506 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The information carrier is a computer-or machine-readable medium, such as the memory 504, the storage device 506, or memory on processor 502.

The high-speed controller 508 manages bandwidth-intensive operations for the computing device 500, while the low speed controller 512 manages lower bandwidth intensive operations. Such allocation of functions is exemplary only. In one implementation, the high-speed controller 508 is coupled to memory 504, display 516, e.g., through a graphics processor or accelerator, and to high-speed expansion ports 510, which can accept various expansion cards (not shown). In the implementation, low speed controller 512 is coupled to storage device 506 and low speed bus 514. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter.

The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

Computing device 550 includes a processor 552, memory 564, and an input/output device such as a display 554, a communication interface 566, and a transceiver 568, among other components. The device 550 can also be provided with a storage device, such as a micro-drive or other device, to provide additional storage. Each of the components 550, 552, 564, 554, 566, and 568, are interconnected using various buses, and several of the components can be mounted on a common motherboard or in other manners as appropriate.

The processor 552 can execute instructions within the computing device 550, including instructions stored in the memory 564. The processor can be implemented as a chipset of chips that include separate and multiple analog and digital processors. Additionally, the processor can be implemented using any of a number of architectures. For example, the processor can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 550, such as control of user interfaces, applications run by device 550, and wireless communication by device 550.

Processor 552 can communicate with a user through control interface 558 and display interface 556 coupled to a display 554. The display 554 can be, for example, a TFT (Thin-Film-Transistor Liquid Crystal Display) display or an OLED (Organic Light Emitting Diode) display, or other appropriate display technology. The display interface 556 can comprise appropriate circuitry for driving the display 554 to present graphical and other information to a user. The control interface 558 can receive commands from a user and convert them for submission to the processor 552. In addition, an external interface 562 can be provide in communication with processor 552, so as to enable near area communication of device 550 with other devices. External interface 562 can provide, for example, for wired communication in some implementations, or for wireless communication in other implementations, and multiple interfaces can also be used.

The memory 564 stores information within the computing device 550. The memory 564 can be implemented as one or more of a computer-readable medium or media, a volatile memory unit or units, or a non-volatile memory unit or units. Expansion memory 574 can also be provided and connected to device 550 through expansion interface 572, which can include, for example, a SIMM (Single In Line Memory Module) card interface. The expansion memory 574 can provide extra storage space for device 550, or can also store applications or other information for device 550. Specifically, expansion memory 574 can include instructions to carry out or supplement the processes described above, and can include secure information also. Thus, for example, expansion memory 574 can be provide as a security module for device 550, and can be programmed with instructions that permit secure use of device 550. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552 that can be received, for example, over transceiver 568 or external interface 562.

Device 550 can communicate wirelessly through communication interface 566, which can include digital signal processing circuitry where necessary. Communication interface 566 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through (radio-frequency) transceiver 568. In addition, short-range communication can occur, such as using a Bluetooth, Wi-Fi, or other such transceiver (not shown). In addition, GPS (Global Positioning System) receiver module 570 can provide additional navigation- and location-related wireless data to device 550, which can be used as appropriate by applications running on device 550.

Device 550 can also communicate audibly using audio codec 560, which can receive spoken information from a user and convert it to usable digital information. Audio codec 560 can likewise generate audible sound for a user, such as through a speaker, e.g., in a handset of device 550. Such sound can include sound from voice telephone calls, can include recorded sound, e.g., voice messages, music files, etc. and can also include sound generated by applications operating on device 550.

The computing device 550 can be implemented in a number of different forms, as shown in the figure. For example, it can be implemented as a cellular telephone 780. It can also be implemented as part of a smartphone 782, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

V. Types of Therapies

The in silico systems biology models described herein can be used to model the effects of any therapies, e.g., medical or procedural therapies, for which a mechanism of action is known or discovered, e.g., for which a mechanism of action is described in the public record or otherwise known, and is converted into data that can be used to update the calibrated model. Then, the systems biology model can be updated with data representing a specific patient's plaque characteristics, and then specific models of potential therapies can be added to the systems biology model updated with the specific patient's information. The results of applying the drug to the patient-specific systems biology model can be compared, and the best performing therapy, or no therapy, can be recommended to the patient.

At the outset, it is important to note that the drug therapies/procedural interventions listed below are merely examples. One skilled in the art, prior to performing the methods described herein would do a review of the literature for drug and/or procedural intervention therapies and would determine the necessary parameters to model the effectiveness of that specific drug and/or procedural intervention therapy. For example, one of skill in the art would determine which molecules represented in the trained in silico systems biology model to manipulate and by how much to alter their levels based on the literature search.

A current search of the literature would show that atherosclerosis has many different endotypes. For example, an endotype of increased LDL is associated with the following genetic factors: LDLR, PCSK9, APOE, APOB-100, SORT1, ANGPTL3, CELSR2, PSRC1, HMGCR; and the following biomarkers: Total cholesterol, LDL-C, ApoB, ApoB-100, ox-LDLs, modified LDL, sdLDL, and PCSK9. An endotype characterized by an increase in Lp(a) is mainly genetically determined by the LPA gene locus and is not significantly influenced by other genetic, dietary, or environmental factors.

Biomarkers associated with an increase in Lp(a) include the following: Lp(a), apolipoprotein isoform (a), and antibodies to Lp(a). An endotype associated with arterial injury (arterial hypertension) is associated with the following genetic factors: ADAMTS7, THBS2, CFDP1, NOX4, EDNRA, PHACTR1, GUCY1A3, CNNM2, CYP17A1; and the following biomarkers: endothelin, angiotensin, adrenomedul-lin, natriuretic peptides, von Willebrand factor, cell adhesion molecules, endothelial progenitor cells, endothelial micro-particles, nitric oxide, and asymmetric dimethylarginine.

An endotype characterized by inflammation is associated with the following genetics: CXCL12, MCP-1, TLRs, SH2B3, HLA, IL-6R, IL-5, PECAM1; and the following biomarkers: TNF, IL-1b, IL-6, IL-12, IL-18, IL-23, IFN-g, IL-17, IL-22, TH17 cells, hsCRP, pentraxin-3, sCD40L, VCAM, and ICAM.

Finally, the endotype characterized by metabolic risk factors is associated with the following genetics: TCF7L2, HNF1A, CTRB1/2, MRAS, ZC3HC1, MIR17HG, and CCDC92; and the following biomarkers: blood glucose, blood insulin, C-peptide, glycated hemoglobin, glycated albumin, sRAGE, fructosamine (Vadim V. Genkel, Igor I. Shaposhnik, "Conceptualization of Heterogeneity of Chronic Diseases and Atherosclerosis as a Pathway to Precision Medicine: Endophenotype, Endotype, and Residual Cardiovascular Risk", *International Journal of Chronic Diseases*, vol. 2020, Article ID 5950813, 9 pages, 2020).

Examples of Drug Therapies

In general, any suitable drug therapy is contemplated by the present application. For instance, any compound that targets (e.g., inhibits) a specific gene, protein, or metabolite. "Inhibits" refers to the compound's ability to control, prevent, restrain, arrest, regulate a molecule's function. Exemplary compounds include, small molecules, inucleic acids (e.g, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs); messenger RNA (mRNA), inhibitory antibodies.

Hyperlipidemia Control Medications

High levels of low-density lipoprotein cholesterol (LDL) is a characteristic feature of cardiovascular diseases, such as atherosclerosis. As such, these diseases can be treated with hyperlipidemia control medications (e.g., intensive lipid lowering therapies, fibrates, niacin, fish oil, statins (like, atorvastatin), ezetimibe, bile acid sequestrants, a proprotein convertase subtilisin kexin type 9 (PCSK9) inhibitor, a cholesteryl ester transfer protein (CETP), adenosine triphosphate-citrate lyase (ACL) inhibitors, omega-3 fatty acid ethyl esters, and marine-derived omega-3 polyunsaturated fatty acids (PUFA).

For example, the effect that an intensive lipid lowering drug would have on a subject can be represented in the in silico systems biology model, thereby allowing a clinician to predict whether an intensive lipid lowering drug would be beneficial to the patient. For instance, in some embodiments the levels, e.g., of the gene level, protein level, or both levels, of LDL are physically lowered in the in silico systems biology model by 75%, 50%, 40%, 30%, 25%, 20%, 10%, or 5%, depending on what is known about how the drug affects the LDL levels. For example, if a specific drug is considered in the literature to be effective in certain patients when the LDL level in the patient has been reduced by 25%, then the model is updated to show an effective reduction of 25%. In some embodiments, the gene level, protein level, or both, of LDL products, such as, glycosylated (glyLDL), oxidized (oxLDL), and minimally-modified (mmLDL), and VLDL are also manipulated (i.e., lowered) in the in silico systems biology model by, for example, 75%, 50%, 40%, 30%, 25%, 20%, 10%, or 5%.

Lowering the levels of these molecules in the in silico systems biology model shows the changes in the levels of one or more genes, proteins, or both, as well as of other molecules that are both directly and indirectly connected to the LDL mechanistic pathway. If the in silico systems biology model shows a reduced possibility of a stroke or myocardial infarction, then an intensive lipid lowering drug would be deemed as beneficial to a patient. If the in silico systems biology model shows no change, or a worsening of one of more conditions of the patient over time, then the intensive lipid lowering drug would not be deemed as beneficial to the patient and would not be recommended.

Anti-Inflammatory Drugs

Inflammation is highly associated with atherosclerosis. As such, therapies that inhibit IL-1, IL1β, TNF, IL12/23, IL17, or other agents that affect an inflammatory cascade can be beneficial in treating subjects with atherosclerosis. Examples of therapies include colchicine, canakinumab, an inhibitor of a pro-inflammatory cytokine induced on danger signaling, a pro-resolvin (e.g., omega-3 fatty acids, like, eicosapentaenoic acid (EPA), docosahexaenoic acid (DHA), or docosapentaenoic acid (DPA)). To date, however, it has been hard to identify which patients would benefit vs. which would not, the latter suffering potentially dangerous side effects until or unless likely response can be established. As a result these drugs are not yet widely used, despite their apparent promise.

Accordingly, the present disclosure provides, in some embodiments, methods for simulating the effect that an anti-inflammatory drug would have on a subject or patient. For example, in some embodiments, the gene level, protein level, or both, of inflammatory molecules (such as, but not limited to, IL-1, IL1β, TNF, IL12/23, or IL17) are also physically manipulated (i.e., lowered) in the in silico systems biology model by, for example, 75%, 50%, 40%, 30%, 25%, 20%, 10%, or 5%, depending on what is known in the literature about how a specific drug affects inflammation. For example, if a specific drug is considered in the literature to be effective in certain patients when the IL-1, IL1β, TNF, IL12/23, or IL17 level in the patient has been reduced by 25%, then the model is updated to show an effective reduction of 25%. Lowering the levels of these molecules in the in silico systems biology model simulates the changes in gene, protein, or both, of other molecules that are both directly and indirectly connected in the inflammatory molecule pathway. In some cases, molecular levels can be raised, for example in pro-resolvin therapies or therapies which raise HDL by way of example, without loss of generality.

Lower plaque instability is a desirable treatment outcome. That is, if the in silico systems biology model after an anti-inflammatory drug effect simulation shows improvement in stability, then an anti-inflammatory drug would be deemed as beneficial to a subject. Plaque stability is quantified based on molecule levels; if the molecule levels of a subject are similar to those from test subjects with stable atherosclerosis, the patient will likely have a relatively higher plaque stability. The relative change in plaque stability of the subject before and after the anti-inflammatory drug is quantified by change in molecule levels in the in silico systems biology model.

Anti-Diabetic Drugs

Metabolic diseases and diabetes are associated with a strongly elevated risk of developing cardiovascular diseases, such as, atherosclerosis. In some subjects, a critical aspect for the development and progression of cardiovascular disease is the impaired lowering of blood glucose levels. Accordingly, in some instances, treatment with an anti-diabetic drug would be beneficial to a subject or patient suffering from a cardiovascular disease.

Accordingly, the present disclosure provide, in some embodiments, methods for simulating the effect that an anti-diabetic drug would have on a subject. For example, in some embodiments, the gene level, protein level, or both, of glucose/metabolic-related molecules (such as, but not limited to, MTOR, NFκβ1, ICAM1, or VCAM1) are also physically manipulated (i.e., lowered) in the in silico systems biology model by, for example, 75%, 50%, 40%, 30%, 25%, 20%, 10%, or 5%, depending on what is known in the literature about how a specific drug affects glucose levels and/or metabolism. For example, if a specific drug is considered in the literature to be effective in certain patients when the MTOR, NFκβ1, ICAM1, or VCAM1 level in the patient has been reduced by 25%, then the model is updated to show an effective reduction of 25%. Lowering the levels of these molecules in the in silico systems biology model shows the changes in gene, protein, or both, of other molecules that are both directly and indirectly connected to the glucose/metabolic-related molecule. If the in silico systems biology model shows that the patient would have a reduced level of diabetes, then an anti-diabetic drug would be deemed as beneficial to a subject. If the in silico systems biology model shows no change or worsening in diabetes symptoms, then an anti-diabetic drug would not be deemed as beneficial to the patient and would not be recommended.

Other Drug Classes

Other drug classes are also contemplated. For example immunomodulating agents, such as those that trigger innate immunity, that are immune tolerance stimulating agents, or that increase Treg activity.

Hypertensive agent (such as, ACE inhibitors) and anti-coagulating agent (agents that reduce thrombin production and/or limits the activity of thrombin) are also envisioned.

Triggers of innate immunity and regulation of intracellular signal transduction suggests novel targets for therapeutic treatment, including the inhibition of the pro-inflammatory cytokines induced on danger signaling. As an example, stimulating immune tolerance with increased Treg activity is being explored. As another example, clearing chylomicron remnants (large triglyceride-rich lipoproteins) is atheroprotective since chylomicron particles and the triglyceride-rich particles are directly and indirectly implicated in plaque development.

Combination Therapies

In some instances, a subject can benefit from the combination of one or more of the above-referenced therapies. Accordingly, in some embodiments, provided are methods for simulating the effect that an intensive lipid lowering and an anti-inflammatory drug would have on a subject; intensive lipid lowering and an anti-diabetic drug would have on a subject; an anti-inflammatory drug and an anti-diabetic drug would have on a subject; or an intensive lipid lowering, an anti-inflammatory drug, and an anti-diabetic drug would have on a subject.

For combination therapies, in determining a known set of molecules affected, the therapeutic response simulation engine 316 considers a first set of molecules affected by a first therapy, a second set of molecules affected by a second therapy, and a third set of molecules affected by an interaction between the first therapy and the second therapy. After defining the known set of molecules, the therapeutic response simulation engine 316 defines a therapeutic effect molecule level for each molecule in the known set of molecules, based on known mechanisms of action of a given combination therapy. Additional steps after defining the therapeutic effect molecule level are described above, referring to FIG. 8B.

Procedural Interventions

In some embodiments, a pharmacotherapy is not the suitable treatment plan for a given patient and a procedural intervention is the only choice. If the simulations in the in silico systems biology model for the various possible drug candidates for a given patient do not show any predicted benefit for the patient, then a procedural intervention should be considered. In general, procedural interventions can make larger-scale changes than pharmacotherapy, for example, outright tissue removal represented by a broad decrease in protein levels, or structural anatomic changes such as the inclusion of a stent, which can block or interfere with connections in the systems biology model. In either case, there can also be localized drug addition, such as drug-eluting stents (DES), which may not address a current condition, but a known consequent action by the biology, in reaction to the procedural intervention, which can be compensatory, but have its own undesired side effects. Perturbations or changes can be made in the trained systems biology model to represent various aspects of such procedural interventions.

Procedural interventions, include, but are not limited to surgery, DES, atherectomy devices, intravascular lithotripsy (IVL), drug coated balloons, variable temperature balloons, and/or prosthetic heart valves.

Drug-Eluting Stents

Stents can be developed for specific patient groups depending on atherosclerosis characteristics and patient co-morbidities. Diabetic patients may respond better to different drugs. In addition, determining the potential rejection or allergic reaction to a specific drug, polymer, or metal can be determined in advance if vessel wall biology and patient response is understood in advance of the intervention. DES are generally made up three components: metallic stent, polymer and drug. Any one of these variables can affect the long-term patency.

For patients with stent thrombosis elevation MI, perhaps DESs with BP are preferable. This has been further supported by the recently reported BIOSTEMI trial showing superiority of ultra-thin BP sirolimus-eluting stent ORSIRO® over DP everolimus-eluting stent XIENCE® with respect to TLF at 1 year. For patients with high bleeding risk, BioFreedom™ or Resolute Onyx™ with 1-month dual antiplatelet therapy (DAPT) have the most supportive data (Comparison of Contemporary Drug-eluting Coronary Stents—Is Any Stent Better than the Others? Available at www.touchcardio.com/interventional-cardiology/journal-articles/comparison-of-contemporary-drug-eluting-coronary-stents-is-any-stent-better-than-the-others, Accessed May 7, 2021).

Patients with diabetes represent a challenging cohort. Most comparative trials of different DESs have shown no difference in effect of stent type between those with and without diabetes. In PLATINUM PLUS, there was no difference the in risk of the primary endpoint between those stented with PROMUS™ versus XIENCE™ (3.5% versus 3.5%, RR 1.00, 95% CI 0.62-1.60). However, in the subgroup with diabetes, XIENCE was favored (7.8% versus 3.0%, RR 2.50, 95% CI 1.16-5.38, interaction p=0.05). This relationship, however, was not seen in the 5-year follow-up data of the preceding PLATINUM trial with a similar design. The comparison of BP DESs versus PP DESs in patients with diabetes was recently examined by Bavishi et al., who included 5,190 patients from 11 RCTs in a meta-analysis, focusing on current-generation stents. After a mean follow-up of 2.7 years, there were no differences in a range of outcomes, including target lesion revascularization (RR 1.02, 95% CI 0.85-1.24, p=0.80) and stent thrombosis (1.66% versus 1.83%, RR 0.84, 95% CI 0.54-1.31, p=0.45) between the two stent types. There was no difference in this relationship between those patients with diabetes treated with and without insulin ((Comparison of Contemporary Drug-eluting Coronary Stents— Is Any Stent Better than the Others? Available at www.touchcardio.com/interventional-cardiology/journal-articles/comparison-of-contemporary-drug-eluting-coronary-stents-is-any-stent-better-than-the-others, Accessed May 7, 2021)).

Atherectomy Devices

Four different methods of atherectomy have been utilized for treatment of femoropopliteal or small vessel infrapopliteal disease: plaque excision (directional) atherectomy, rotational atherectomy/aspiration, laser atheroablation, and orbital atherectomy.

Atherosclerotic plaque molecular signature, morphology proportions & volume can determine the ability of stents to fully expand and stay patent within the focal area which can affect long- and short-term outcomes.

Understanding the lipid volume, matrix proportion, calcium extent, arc, thickness, volume, area and their impact on long term outcomes can help determine if a patient will respond better acutely and if long term outcomes/patency are improved when selecting different atherectomy devices for lesion preparation.

Intravascular Lithotripsy (IVL)

Atherosclerotic plaque molecular signature, morphology proportions & volume can determine the effectiveness of IVL within the focal lesion area which can affect long- and short-term outcomes. The power and pulse of the lithotripsy can potentially be determined by the plaque morphology.

Drug Coated Balloons

Target lesion revascularization rates in coronary and peripheral arterial disease can be affected by plaque morphology and/or atherosclerotic molecular signature. Different drug coated balloons can be developed for specific patient groups depending on atherosclerosis characteristics and patient co-morbidities. Patients with diabetes combined with different proportions of biological substances of the plaque can determine which drug balloon/excipient combo would be best suited for a particular patient. The type of drug (currently either paclitaxel or sirolimus), the excipient and the timing of release (dosing) can be tailored depending on plaque morphology to extend target lesion patency. Highly lipidic lesions like in-stent restenosis can affect long term patency and warrant a patient specific drug. Highly calcified lesions can require a different kind of drug coated balloon. A combination of atherectomy, plus a specific drug coated balloon can be selected based on molecular signature of the plaque.

Variable Temperature Balloons

The atherosclerotic lesion molecular signature can help determine if a patient is not a good candidate (would not respond well) for drug coated balloon or drug eluting stent and requires an alternative interventional therapy. The patient may have co-morbidities or allergies to certain drugs requiring a different therapeutic approach. This can avoid catastrophic acute reactions and long-term implications of sometimes permanent implants. The use of a "hot balloon" or a "cold balloon" may be warranted for certain lesion morphology characteristics.

Cryoplasty combines the dilatation force of angioplasty with the simultaneous delivery of cold thermal energy to the arterial wall. Both mechanisms are achieved simultaneously by filling the angioplasty catheter with nitrous oxide instead of the usual contrast saline/solution mixture. Cryotherapy has been proven to biologically alter the behavior of arterial cellular components in a benign healing process (The Next-Generation PolarCath™ System Available at evtoday.com/articles/2018-jan-supplement/the-next-generation-polar-cath-system, Accessed May 10, 2021).

Several scientific studies have demonstrated that this cooling process within the vessel results in: weakening of the plaque, promoting uniform dilation and reducing vessel trauma; alteration of elastin fibers to reduce vessel wall recoil, while collagen fibers remain undisturbed and capable of maintaining architectural integrity; induction of smooth muscle apoptosis, which is associated with reduced neointimal formation and, subsequently, less restenosis ((The Next-Generation PolarCath System Available at evtoday.com/articles/2018-jan-supplement/the-next-generation-polarcath-system, Accessed May 10, 2021)).

So called Hot Balloons are currently in development and may alter the morphology and fibrous cap thickness while reducing neointimal hyperplasia seen with standard angioplasty balloons.

Prosthetic Heart Valves

Understanding the molecular signature of heart valve disease phenotypes can help determine which drugs can arrest the disease and potentially reverse it before progressing to an irreparable state. In addition, the pathology of patient specific valve disease can determine the long-term efficacy and patient response to a particular prosthetic heart valve (TAVR: self-expanding, balloon expandable or different surgically implanted valves.)

Heart valves are complex tri-layered structures that ensure the unidirectional flow of blood. Scientists are actively investigating how characteristics of the two major cell types, valvular endothelial cells (VECs) and valvular interstitial cells (VICs), and their mechanical relationships with the valvular extracellular matrix promote structural integrity and age-related remodeling. Abnormal changes in VECs, VICs, and the extracellular matrix at the molecular level lead to gross tissue malformations and dysfunction. Improving our understanding of heart valve biology, the impact of cardiovascular drugs, and remodeling changes will be critical to the development of novel therapies for heart valve diseases (Xu, S. and K. J. Grande-Allen (2010). "The role of cell biology and leaflet remodeling in the progression of heart valve disease." Methodist Debakey Cardiovasc J 6(1): 2-7).

The clinical and pathological features of the most frequent intrinsic structural diseases that affect the heart valves are well established, but heart valve disease mechanisms are poorly understood, and effective treatment options are evolving. Major advances in the understanding of the structure, function and biology of native valves and the pathobiology, biomaterials and biomedical engineering, and the clinical management of valvular heart disease have occurred over the past several decades (Schoen, F. J. (2018). "Morphology, Clinicopathologic Correlations, and Mechanisms in Heart Valve Health and Disease." Cardiovasc Eng Technol 9(2): 126-140).

Procedural interventions in CAD include coronary artery bypass grafts (CABG), percutaneous coronary intervention (PCI, e.g., balloon angioplasty with or without stent placement). Also of relevance are procedures for valve replacement or repair including transcatheter aortic valve replacement (TAVR), due to the need for coronary artery assessment in the pre-procedure work-up.

Optimal Medical Therapy (OMT)

Most subjects on statins are prescribed a relatively low dose, but as there are indications of plaque requiring more intensity, various approaches exist. One approach is to increase the dose, for example, high-dose atorvastatin is often prescribed for subjects with hypercholesterolemia. There is a growing consensus that hypertriglyceridemia vs. hypercholesterolemia differs (Le, N. A. and M. F. Walter, *The role of hypertriglyceridemia in atherosclerosis*. Curr Atheroscler Rep, 2007. 9(2): p. 110-5), with at least one recent drug (Vascepa®) capturing current attention. For subjects with hypertriglyceridemia, improved outcomes have been reported in trials such as the Reduction of Cardiovascular Events with EPA—Intervention Trial (REDUCE-IT) trial (Bhatt et al., *REDUCE-IT USA: Results From the* 3146 *Patients Randomized in the United States*. Circulation, 2020. 141(5): p. 367-375; Bhatt et al., *Cardiovascular Risk Reduction with kosapent Ethyl for Hypertriglyceridemia*. N Engl J Med, 2019. 380(1): p. 11-22; Bhatt et al., *Reduction in First and Total Ischemic Events With kosapent Ethyl Across Baseline Triglyceride Tertiles*. J Am Coll Cardiol, 2019. 74(8): p. 1159-1161; Bhatt, D. L., *Reduce-It*. Eur Heart J, 2019. 40(15): p. 1174-1175; Bhatt et al., *Effects of kosapent Ethyl on Total Ischemic Events: From REDUCE-IT*. J Am Coll Cardiol, 2019. 73(22): p. 2791-2802; Boden et al., *Profound reductions in first and total cardiovascular events with icosapent ethyl in the REDUCE-IT trial: why these results usher in a new era in dyslipidaemia therapeutics*. Eur Heart J, 2019). Detailed quantitative studies have yet to be done to determine how IPE affects tissues in the vessel wall because it has not been previously possible to quantitatively assess changes in plaque morphology non-invasively.

Other Emerging Drug Classes

Triggers of innate immunity and regulation of intracellular signal transduction suggests novel targets for therapeutic treatment, including the inhibition of the pro-inflammatory cytokines induced on danger signaling (Zimmer et al., *Danger signaling in atherosclerosis*. Circ Res, 2015. 116(2): p. 323-40). As an example, stimulating immune tolerance with increased Treg activity is being explored (Herbin et al., *Regulatory T-cell response to apolipoprotein B100-derived peptides reduces the development and progression of atherosclerosis in mice*. Arterioscler Thromb Vasc Biol, 2012. 32(3): p. 605-12). As another example, clearing chylomicron remnants (large triglyceride-rich lipoproteins) (Rahmany, S. and I. halal, *Biochemistry, Chylomicron, in StatPearls*. 2020: Treasure Island (FL)) is atheroprotective since chylomicron particles and the triglyceride-rich particles are directly and indirectly implicated in plaque development (Tomkin, G. H. and D. Owens, *The chylomicron: relationship to atherosclerosis*. Int J Vasc Med, 2012. 2012: p. 784536).

Drug candidates in other therapeutic areas, such as immuno-modulators in cancer can have side effects where atherosclerosis is aggravated, due to activation of T-cells in the plaques that can result in plaque rupture, but there are no accurate methods to track these effects. There is a widely recognized need for effective markers during drug development for atherosclerosis and even unrelated diseases as well as companion diagnostics post-marketing.

VI. Examples of Applications

Clinical Decision Support Systems

The present disclosure can be used as a clinical decision support system. The invention supports clinical decision making by informing the clinician on what the likely effect would be for different possible therapies, and also provides tools to help discuss these options with the patient. The disclosure provides a recommendation based on the statistical significance of the likely improvement, and can compare across potential recommendations to identify the one that has been considered which exceeds others in the degree of improvement provided. This recommendation can be understood as determining a clinical action, or informing a decision that leads to a clinical action.

Such recommendations and actions that proceed from use of the presently disclosed methods and systems allow therapy to be tailored to the individual rather than be based only on population statistics. Presently, clinical guidelines have not been able to use such diagnostic specificity because there have been no means to do so. Individuals have different genetic pre-disposition, environmental exposures, and differing lifestyle habits. Both modifiable and non-modifiable risk factors influence what is best for that patient. The in silico systems biology models described herein provide a description of the disease, and a way to process and calibrate it for individual patients. This then enables the actual expected effect of therapies to be evaluated more specifically than previously possible. The benefit is that rather than referring to the population as a whole or at best sub-populations, that actual molecular level effects may be considered.

This has been widely understood in cancer treatment and is increasingly the norm. However, whereas cancer is generally informed by molecular diagnostics run on biopsied tumor tissue, it is not possible to biopsy atherosclerotic plaque tissues because it can cause a disruption, which is not desired. As a result, the computer-based systems described herein, which utilize advanced techniques, including forms of artificial intelligence, can extend what the clinicians would otherwise be able to do by themselves. The features of the tissues are generally of too complex a nature as to be easily interested by a human observer but the present invention analyses data at a far more granular level. To make such a decision support system practical is a mix of mathematical formulations, knowledge representation, and architecture in terms of user interfaces, reporting systems, and backbone of computation, all as described herein.

The utility of any diagnostic system must address what can be done with the information. Presently numerous powerful therapies exist, both procedural, pharmaceutical, or combinations such as drug eluting stents. By evaluating the individualized response to these therapies, the current systems and methods make diagnostics actionable by identifying the degree of improvement and annotates that improvement level with the statistical significance of its computation. These recommendations can be presented, for example, on screen-based user interfaces or in printable PDF forms that may be used in communicating among groups of clinicians or with patients.

Identification of Likely Responses at an Individual Patient Level

Provided herein are methods and systems for identifying a likely response, at an individual patient level, for a potential therapeutic agent. More specifically, an in silico systems biology model is generated, trained, and updated to create a calibrated model, as described herein. Then the calibrated model is updated with patient-specific information (e.g., virtual 'omics or from histological analysis obtained from actual tissue and/or blood specimens), to create the baseline condition. The in silico systems biology model representing the baseline condition is then further updated to simulate one or more potential therapies based on the mechanism of action for each therapy to arrive at various in silico systems biology model representations of various simulated conditions for each potential therapy. Based on the results, the patient is provided with a recommendation, e.g., in the form of a report, of a suitable therapy or treatment regimen. The resulting absolute pathology as well as the relative improvement in the pathology can be quantified and expressed as a likely response for each simulated therapy.

Quantification of Actual Responses at an Individual Patient Level

Also provided herein are methods and systems for quantifying an actual response, at an individual patient level, for a potential therapeutic agent. More specifically, an in silico systems biology model is generated, trained, and updated to create the calibrated model, as described herein. Then the calibrated model is updated with patient-specific information (e.g., virtual 'omics or from histological analysis obtained from actual tissue and/or blood specimens), to create the baseline condition. The in silico systems biology model representing the baseline condition is then further updated to simulate each potential therapy based on the mechanism of action for each therapy to arrive at various in silico systems biology model representations of various simulated conditions for each potential therapy. Based on the results, the patient is provided with a recommendation of a suitable therapy or treatment regimen.

After the patient has been on the recommended treatment regimen for a time sufficient to elicit a therapeutic response, the in silico systems biology model (i.e., a calibrated model that has not been updated with new patient-specific information) is updated with new patient-specific information (e.g., new virtual 'omics data), to create a model that represents a simulation of the effect of the recommend therapy (after-treatment simulation).

The baseline condition is compared to the after-treatment simulation. If there has been an actual improvement in the pathology, that result provides an indication that the patient improved under the treatment, even if the specific changes to the protein levels were not exactly as originally simulated. Further, if the specific changes to the protein levels were approximately as simulated, then one can further determine that the treatment caused the improvement and the method can be considered a surrogate end-point for treatment effect. In other words, in some embodiments, the simulations need to be only approximately correct to provide the intended utility in clinical practice.

Quantification of Actual Responses at a Cohort Level

Also provided herein are methods and systems of determining the actual responses to a specific treatment at a cohort level of patients or test subjects.

For example, an in silico systems model can be built. More specifically, an in silico systems biology model can be generated, trained, and updated to create the calibrated system, as described here. Then, for each patient or test subject in a cohort, information from each patient (e.g., virtual 'omics or from histological analysis obtained from actual tissue and/or blood specimens) is used to update the model for each patient/test subject to form the baseline condition. For each patient/test subject in the cohort and for each therapy to be simulated, the calibrated model is perturbed based on the mechanism of action for the therapy to arrive at a simulated condition.

After an interval where each patient/test subject in the cohort has received the (adjusted) recommended treatment, e.g., after a time sufficient to elicit a therapeutic response, the in silico systems biology model, i.e., a calibrated model that has not been updated with new patient-specific information, is updated with new patient-specific information (e.g., new virtual 'omics or new histological analysis obtained from actual tissue and/or blood specimens), to create a model that represents an after-treatment simulation. If there has been an actual improvement in the pathology across the cohort of patients, one can conclude that the patients improved under the treatment, even if the specific changes to the protein levels were not exactly as simulated. Further, if the specific changes to the protein levels were approximately as simulated, then it can further be said that the treatment caused the improvement and the method may be considered to be a surrogate end point for treatment effect. This can be performed in the context of an observational study, a randomized clinical trial, or other study designs.

Detecting Contraindications at an Individual Patient Level

Also provided herein are methods and systems wherein after the simulated conditions are generated for each potential therapy, contra-indications at the individual patient level are detected.

For example, provided herein are methods for identifying a likely response, at an individual patient level, for a potential therapeutic agent. More specifically, an in silico systems biology model is generated, trained, and updated to create the calibrated system, as described above. Then the calibrated model is updated with patient-specific information (e.g., virtual 'omics or from histological analysis obtained from actual tissue and/or blood specimens), to create the baseline condition. The in silico systems biology model representing the baseline condition, also as described above, is then further updated to simulate each potential therapy based on the mechanism of action for each treatment to arrive at various in silico systems biology model representing various simulated condition for each potential treatment. Deleterious side effects in the simulated condition are determined by looking at how molecules are perturbed in the model. That is, even if there is an apparent improvement in the condition with respect to the pathology, there may be inadvertent other effects that are worse for the patient than the intended improvement.

Once determined, those other effects can also be provided to the patient, e.g., in a report.

Identification of Likely Adverse Reactions, Current Actual Toxicity, or Likely Future Negative Reactions, at an Individual Patient Level Also provided herein are methods and systems, wherein after the simulated conditions are generated for each potential treatment, likely adverse reactions, current actual toxicity, or likely future negative reactions, at an individual patient level are identified.

For example, provided herein are methods and systems for identifying a likely response, at an individual patient level, for a potential therapeutic agent. More specifically, an in silico systems biology model is generated, trained, and updated to create the calibrated model, as described herein. Then the calibrated model is updated with patient-specific information (e.g., virtual 'omics or from histological analysis obtained from actual tissue and/or blood specimens), to create the baseline condition. The in silico systems biology model representing the baseline condition, also as described herein, is then further updated to simulate each potential therapy based on the mechanism of action for each therapy to arrive at various in silico systems biology model representations of various simulated conditions for each potential therapy.

Deleterious side effects are determined (adverse reaction) in the simulated condition, that is, even if there is an apparent improvement in the condition with respect to the pathology, there may be inadvertent other effects that are worse for the patient than the intended improvement. One can use this information to modify the therapy recommendations, that is, for example, one may downgrade a recommendation for treatments that improve the pathology, but also have one or more adverse reactions.

After an interval where the patient(s) has received the (adjusted) recommended treatment, e.g., after a time sufficient to elicit a therapeutic response, the in silico systems biology model (i.e., one that has not been updated with new patient-specific information) is updated with new patient-specific information, e.g., information either obtained through collection of tissue and/or blood specimens from the patient using transcriptomics and/or proteomics and/or metabolomics, or from non-invasive prediction (virtual 'omics)), to create a model that represents an after-treatment simulation.

If there has been an actual improvement in the pathology, one can conclude that the patient or patients improved under the therapy, even if the specific changes to the protein levels were not exactly as simulated. Further, if the specific changes to the protein levels were approximately as simulated, then one can further determine that the therapy caused the improvement and the method can be considered to be a surrogate end point for a treatment effect.

If there has been an adverse effect, one can determine that the patient failed to improve under the treatment, even if the specific changes to the protein levels were not exactly as simulated.

In some instances, the in silico model can be rebuilt (i.e., step one) with additional information regarding adverse events. All subsequent steps can then be repeated to determine additional improvement, adverse effects, or both for modifying treatments or for conducting dynamic, combination, multi-stage, or adaptive clinical trial designs or individual patient management.

Screening Tools for Clinical Trial Enrichment to "Select In" Cases that Increase the Statistical Power of a Clinical Trial Also provided herein are methods and systems for creating and using screening tools for clinical trials to determine "select in" cases. More specifically, an in silico systems biology model is generated, trained, and updated to create the calibrated system, as described herein. Then the calibrated model is updated with patient-specific information (e.g., virtual 'omics or from histological analysis obtained from actual tissue and/or blood specimens), to create the baseline condition. The in silico systems biology model representing the baseline condition, also as described herein, is then further updated to simulate each potential treatment based on the mechanism of action for each treatment to arrive at various in silico systems biology model representing various simulated condition for each potential treatment. The resulting pathology as well as the relative improvement in the pathology is quantified and expressed as a likely response for each simulated treatment.

If the likely improvement of the patient is above an inclusion criteria threshold, one would select the patient for the clinical trial. Otherwise, one would not select the patient for the clinical trial, if there are no other exclusion or inclusion criteria issues.

Screening Tools for Clinical Trial Enrichment to "Select Out" Cases that Decrease the Statistical Power of a Clinical Trial Also provided herein are methods and systems for creating and using screening tools for clinical trials to determine "select out" cases. More specifically, an in silico systems biology model is generated, trained, and calibrated to create the calibrated system, as described above. Then the calibrated model is updated with patient-specific information (e.g., virtual 'omics or from histological analysis obtained from actual tissue and/or blood specimens), to create the baseline condition. The in silico systems biology model representing the baseline condition, also as described herein, is then further updated to simulate each potential treatment based on the mechanism of action for each treatment to arrive at various in silico systems biology model representing various simulated condition for each potential treatment. Any deleterious side effects (adverse reaction) in the simulated condition are flagged, that is, even if there is an apparent improvement in the condition with respect to the pathology, there may be an inadvertent other effect that is worse for the patient than the intended improvement.

If the adverse reaction of the patient is above an exclusion criteria threshold, then one would not select the patient for the clinical trial. Otherwise, one would select the patient for the clinical trial, if there are no other exclusion or inclusion criteria issues.

EXAMPLES

The invention is further described in the following examples, which do not limit the scope of the invention described in the claims.

Example 1: Creation of an in Silico Systems Biology Model

Methods
Cohort Assembly and Proteomic Processing

A total of 22 male patients on statin therapy undergoing stroke-preventive carotid endarterectomy (CEA) for high-grade (>50% NASCET (Golriz Khatami, S. et al. Using predictive machine learning models for drug response simulation by calibrating patient-specific pathway signatures. *npj Systems Biology and Applications* 7, 1-9 (2021))) stenosis were prospectively enrolled to represent the differences in protein levels between unstable and stable atherosclerosis, yielding 18 patients with data from CTA, histology, and plaque proteomics for complete characterization (comprising three spatial scales) (see FIGS. 3A-3F).

Study Cohort Demographics are Summarized in

Table 3, below. Briefly, CEAs were collected at surgery and retained within a biobank, with details of sample collection and processing previously described.[11,12] All samples were collected with informed consent from patients and the study was approved by the Ethical Review Board. Continuous variables are presented as medians (inter-quartile range). No variable was found to be significantly different between stable and unstable phenotypes.

Demographic variables were summarized to characterize the cohort and identify significantly different values across plaque subgroups. Categoric variables with less than 25% missing data were tabulated with fractions and significance analysed with Fisher Exact test. Continuous variables were tabulated as medians with inter-quartile range and significance analysed by Wilcoxon non-parametric test (using a confidence level of p=0.05).

(Barrett, T. J. Macrophages in Atherosclerosis Regression. *Arteriosclerosis, thrombosis, and vascular biology* 40, 20-33, doi:10.1161/ATVBAHA.119.312802 (2020)) categorizing symptomatic and asymptomatic patients based on plaque stability (minimal, stable, or unstable) and resulting in 18 patients appropriately matched with respect to symptomatology and plaque morphology features. We further characterized the patients utilizing analyses from CTA by ElucidVivo (Boston, Mass. USA) for plaque morphology comprising structural anatomy and tissue characteristics as well as non-invasive plaque stability classification (see, e.g., FIGS. 3A-3F). These methods can elucidate prevalent biological processes relevant for plaque instability as previously described (Kalluri. & Weinberg, The basics of epithelial-mesenchymal transition. *J Clin Invest* 119, 1420-1428, doi:10.1172/JCI39104 (2009); Kovacic et al., Epithelial-to-mesenchymal and endothelial-to-mesenchymal transition: from cardiovascular development to disease. *Circulation* 125, 1795-1808, doi:10.1161/CIRCULATIONAHA.111.040352 (2012)).

TABLE 3

Study Cohort Demographics

| Categoric | Stable | Unstable | p | Continuous | Stable | Unstable | p |
|---|---|---|---|---|---|---|---|
| Male | 100% (8/8) | 100% (10/10) | 1.00 | Age | 66.97 (7.76) | 72.63 (11.52) | 0.32 |
| Previous MI | 50% (4/8) | 20% (2/10) | 0.32 | High-sensitivity CRP (mg/l) | 1.00 (1.19) | 2.70 (2.50) | 0.10 |
| Angina Pectoris | 12% (1/8) | 10% (1/10) | 1.00 | S-Cholesterol (mmol/l) | 3.40 (0.70) | 4.00 (0.80) | 0.15 |
| Hypertension | 88% (7/8) | 80% (8/10) | 1.00 | Triglycerides (mmol/l) | 1.00 (0.31) | 1.50 (1.10) | 0.17 |
| PVD | 12% (1/8) | 10% (1/10) | 1.00 | Hemoglobin (g/dl) | 151.00 (14.50) | 141.00 (12.00) | 0.23 |
| Smoker | 12% (1/8) | 22% (2/9) | 1.00 | Diastolic BP | 62.50 (2.50) | 76.00 (11.00) | 0.34 |
| | | | | % Stenosis by U/S | 89.50 (9.50) | 75.00 (25.00) | 0.55 |
| | | | | Hemoglobin A1C (mmol/mol) | 3.90 (0.50) | 4.40 (1.30) | 0.55 |
| | | | | LPK | 7.80 (1.35) | 6.70 (1.40) | 0.63 |
| | | | | EVF | 41.50 (41.79) | 41.00 (4.00) | 0.66 |
| | | | | Fibrinogen | 3.90 (0.90) | 3.60 (0.47) | 0.66 |
| | | | | LDL (mmol/) | 1.60 (0.65) | 1.95 (0.80) | 0.72 |
| | | | | S-Creatinine (mg/dl) | 81.50 (32.75) | 85.00 (21.00) | 0.77 |
| | | | | BMI | 25.40 (3.11) | 25.72 (3.89) | 0.83 |
| | | | | HDL (mmol/l) | 1.20 (0.25) | 1.20 (0.40) | 0.91 |
| | | | | Erythrocyte count | 4.90 (0.45) | 4.65 (0.80) | 0.94 |
| | | | | eGFR | 72.00 (18.50) | 65.00 (23.00) | 0.96 |
| | | | | Systolic BP | 130.00 (5.00) | 132.50 (13.75) | 1.00 |

Excised plaques were divided transversally at the most stenotic part; the proximal half used for protein analysis and the distal half fixed in 4% formaldehyde and prepared for histology. Histological analysis was performed on Masson-Tri-Chrome stained sections to assess presence of instability features such as lipid-rich necrotic core (LRNC), intra-plaque haemorrhage (IPH), fibrous cap thickness and integrity, and other factors according to the Virmani classification LC-MS/MS Analysis and Protein Identification Using methods previously described (Evrard, S. M. et al. Corrigendum: Endothelial to mesenchymal transition is common in atherosclerotic lesions and is associated with plaque instability. *Nat Commun* 8, 14710, doi:10.1038/ncomms14710 (2017)) plaques from selected patients were processed for proteomic analysis. Briefly, 4 mm thick sections were retrieved from the proximal half of the lesion, one from the peripheral end and one from the central core.

Proteomic processing was performed using high-resolution isoelectric focusing (HiRIEF (Newby, A. C. et al. Vulnerable atherosclerotic plaque metalloproteinases and foam cell phenotypes. *Thrombosis and haemostasis* 101, 1006-1011 (2009))) with median normalization of ratios on the peptide spectrum match (PSM) level. FTMS master scans were followed by data-dependent MS/MS. Spectra were searched using MSGF+ (v10072) (Bittner et al., P6164 High level of EPA is associated with lower perivascular coronary attenuation as measured by coronary CTA. *European heart journal* 40, ehz746. 0770 (2019)) and Percolator (v2.08) (Antonopoulos, A. S. et al. Detecting human coronary inflammation by imaging perivascular fat. *Science translational medicine* 9, doi:10.1126/scitranslmed.aa12658 (2017)), where search results were grouped for Percolator target/decoy analysis. PSMs found at 1% PSM- and peptide-level FDR (false discovery rate) were used to infer gene identities, and median normalization of ratios on the PSM level was performed. Protein level FDRs were calculated using the picked-FDR method (Raj sheker, S. et al. Crosstalk between perivascular adipose tissue and blood vessels. *Curr Opin Pharmacol* 10, 191-196, doi:10.1016/j.coph.2009.11.005 (2010)).

Cell Network Pathway Selection

A systems biology model was created from a combination of proteomic pathways based on the differences in plaque stability, which represented late-stage disease, augmented with literature-based and data base retrieval, e.g., from the Kyoto Encyclopedia of Genes and Genomes (KEGG) database, to ensure coverage of earlier stages of atherogenesis. Keywords were used to search the KEGG database (see, e.g., Table 4 below).

KEGG is a database resource for understanding high-level functions and utilities of the biological system, such as the cell, the organism, and the ecosystem, from genomic and molecular-level information. It is a computer representation of the biological system, consisting of molecular building blocks of genes and proteins (genomic information) and chemical substances (chemical information) that are integrated with the knowledge on molecular wiring diagrams of interaction, reaction, and relation networks (systems information). It also contains disease and drug information (health information) as perturbations to the biological system. In KEGG, reference pathway maps of molecular interaction/reaction network diagrams are represented in terms of the KEGG Orthology (KO) groups, so that experimental evidence in specific organisms can be generalized to other organisms through genomic information. In other words, maps (such as the ones referred to in Tables 5 and 6 below) are reference maps and are noted with a "mapxxxxx" identification number. These maps can then be generalized to *Homo sapiens* (i.e., humans) and are noted with a "hsaxxxxx" identification number. For example, map05417 refers to the reference pathway for Lipid and Atherosclerosis, and HSA05417 refers to the Lipid and Atherosclerosis pathway in *Homo sapiens*.

TABLE 4

KEGG Pathway Database Search Terms Used for Identification of Pathways Drawn from Literature Reviews

| | | | |
|---|---|---|---|
| aaa | efferocytosis | jak2 | proteoglycan |
| abca1 | egfr | klf2 | psoriasis |
| adaptive | endoplasmic | ldl | resolvin |
| adipose | endothelial | ldlr | sirolimus |
| adventitia | endothelin | leukin | smc |
| ampk | enos | leukocyte | statin |
| angiogenesis | epithelial | lipidemia | stretch |
| apob | e-selectin | lipoprotein | subtilisin %2Fkexin |
| apoc | Everolimus | Long-term | tcell |
| apoe | Extracellular + matrix | lymphocyte | Terpenoid + backbone + biosynthesis |
| asxl1 | Fat + digestion + and + absorption | macrophage | TET2 |
| athero | fatty + acid | mast | TGF |
| atheroma | fibroblast | MCP1 | tgfa |
| atherosclerosis | fibronectin | metalloproteinase | TGFB |
| blvrb | flk1 | metformin | thrombin |
| Calcification | foam | MMP | thrombus |
| Canakinumab | glycocalyx | MMP2 | tie2 |
| | Glycolysis + %2F + Gluconeogenesis | monocyte | timp2 |
| catecholamines | hdl | mrna | tp53 |
| cd4 | hematopoietic | necrosis | treg |
| cell + cycle | hscrp | neutrophil | triglyceride |
| Cellular + senescence | hypertension | nfkb | triglyceridemia |
| cetp | icam1 | N-Glycan + biosynthesis | u937 |
| cholesterolemia | Icosapent | nicotine | vasa + vasorum |
| chylomicron | ifn | nitric + oxide | vasodilation |
| cigarette | il17 | oxidative + stress | vcam1 |
| colchicine | il1b | pad | vegf |
| collagen | il6 | pcsk | vldl |
| coronary | il8 | peripheral | vsmc %2C + athero |
| C-reactive + protein | immune | Phosphatidylinositol | |
| CRP | immunology | Primary + bile + acid + biosynthesis | |

TABLE 4-continued

KEGG Pathway Database Search Terms Used for Identification
of Pathways Drawn from Literature Reviews

| | | |
|---|---|---|
| cytokine | inflammation | progenitor |
| dnmt | innate | proprotein + convertase |
| dnmt3a | insulin | proresolving |
| ecm | intima | prostacyclin |

Selected pathways were assigned according to their applicability to four primary cell types: endothelial cells (ECs), vascular smooth muscle cells (VSMCs), macrophages, and lymphocytes (Table 5). In Table 5, a "1" is placed to signify that the pathway has a more than trivial participation in the given cell type. In general, pathways were deemed either fully included or fully excluded relative to a cell type (Table 6). In Table 6, the table comprises pathways which are generally common to mammalian cells of many types, including those identified. Some pathways contained cell-type specific portions. In such cases, pathways were split prior to inclusion.

TABLE 5

Relevance of Selected Proteomic Pathways to Four Cell Types

| ec relevance | vsmc relevance | mac relevance | lymphocyte relevance | Entry | Name |
|---|---|---|---|---|---|
| | 1 | | | map04270 | Vascular smooth muscle contraction |
| 1 | | | | map04370 | VEGF signaling pathway |
| | | 1 | | map04380 | Osteoclast differentiation |
| | | | 1 | map04613 | Neutrophil extracellular trap formation |
| | | | 1 | map04650 | Natural killer cell mediated cytotoxicity |
| | | | 1 | map04658 | Th1 and Th2 cell differentiation |
| | | | 1 | map04659 | Th17 cell differentiation |
| | | | 1 | map04660 | T cell receptor signaling pathway |
| | | | 1 | map04662 | B cell receptor signaling pathway |
| | | 1 | | map04664 | Fc epsilon RI signaling pathway |
| | | 1 | | map04666 | Fc gamma R-mediated phagocytosis |
| 1 | | | | map04915 | Estrogen signaling pathway |
| | 1 | | | map04931 | Insulin resistance |
| | | | 1 | map04940 | Type I diabetes mellitus |
| 1 | | | | map05418 | Fluid shear stress and atherosclerosis |
| | | 1 | 1 | map00510 | N-Glycan biosynthesis |
| | | 1 | 1 | map01523 | Antifolate resistance |
| | 1 | 1 | | map03320 | PPAR signaling pathway |
| | | 1 | 1 | map04062 | Chemokine signaling pathway |
| 1 | 1 | | | map04510 | Focal adhesion |
| 1 | 1 | | | map04520 | Adherens junction |
| 1 | 1 | | | map04530 | Tight junction |
| 1 | 1 | | | map04540 | Gap junction |
| 1 | 1 | | | map04610 | Complement and coagulation cascades |
| 1 | 1 | | | map04611 | Platelet activation |
| 1 | | | 1 | map04612 | Antigen processing and presentation |
| | | 1 | 1 | map04622 | RIG-I-like receptor signaling pathway |
| | | 1 | 1 | map04623 | Cytosolic DNA-sensing pathway |
| 1 | | | 1 | map04625 | C-type lectin receptor signaling pathway |
| | | 1 | 1 | map04630 | JAK-STAT signaling pathway |
| | | 1 | 1 | map04640 | Hematopoietic cell lineage |
| | | 1 | 1 | map04657 | IL-17 signaling pathway |
| | | 1 | 1 | map04750 | Inflammatory mediator regulation of TRP channels |
| 1 | 1 | | | map04810 | Regulation of actin cytoskeleton |
| | | 1 | 1 | map04920 | Adipocytokine signaling pathway |

TABLE 5-continued

Relevance of Selected Proteomic Pathways to Four Cell Types

| ec relevance | vsmc relevance | mac relevance | lymphocyte relevance | Entry | Name |
|---|---|---|---|---|---|
| | | 1 | 1 | map04923 | Regulation of lipolysis in adipocytes |
| | 1 | 1 | | map04979 | Cholesterol metabolism |
| 1 | 1 | 1 | | map00531 | Glycosaminoglycan degradation |
| 1 | 1 | 1 | | map01040 | Biosynthesis of unsaturated fatty acids |
| | 1 | 1 | 1 | map04014 | Ras signaling pathway |
| 1 | 1 | 1 | | map04371 | Apelin signaling pathway |
| 1 | | 1 | 1 | map04514 | Cell adhesion molecules |
| | 1 | 1 | 1 | map04621 | NOD-like receptor signaling pathway |
| 1 | | 1 | 1 | map04670 | Leukocyte transendothelial migration |
| 1 | 1 | 1 | | map04911 | Insulin secretion |
| 1 | 1 | | 1 | map04922 | Glucagon signaling pathway |
| 1 | 1 | 1 | | map04933 | AGE-RAGE signaling pathway in diabetic complications |
| | 1 | 1 | 1 | map04935 | Growth hormone synthesis, secretion and action |

TABLE 6

Selected Proteomic Pathways Included in all Four Cell Types

| ec relevance | vsmc relevance | mac relevance | lymphocyte relevance | Entry | Name |
|---|---|---|---|---|---|
| 1 | 1 | 1 | 1 | ap07042 | Antineoplastics - agents from natural products |
| 1 | 1 | 1 | 1 | map00010 | Glycolysis/Gluconeogenesis |
| 1 | 1 | 1 | 1 | map00020 | Citrate cycle (TCA cycle) |
| 1 | 1 | 1 | 1 | map00030 | Pentose phosphate pathway |
| 1 | 1 | 1 | 1 | map00520 | Amino sugar and nucleotide sugar metabolism |
| 1 | 1 | 1 | 1 | map00532 | Glycosaminoglycan biosynthesis - chondroitin sulfate/dermatan sulfate |
| 1 | 1 | 1 | 1 | map00534 | Glycosaminoglycan biosynthesis - heparan sulfate/heparin |
| 1 | 1 | 1 | 1 | map00562 | Inositol phosphate metabolism |
| 1 | 1 | 1 | 1 | map00590 | Arachidonic acid metabolism |
| 1 | 1 | 1 | 1 | map00630 | Glyoxylate and dicarboxylate metabolism |
| 1 | 1 | 1 | 1 | map00910 | Nitrogen metabolism |
| 1 | 1 | 1 | 1 | map00920 | Sulfur metabolism |
| 1 | 1 | 1 | 1 | map01100 | Metabolic pathways |
| 1 | 1 | 1 | 1 | map01200 | Carbon metabolism |
| 1 | 1 | 1 | 1 | map01212 | Fatty acid metabolism |
| 1 | 1 | 1 | 1 | map01240 | Biosynthesis of cofactors |
| 1 | 1 | 1 | 1 | map02010 | ABC transporters |
| 1 | 1 | 1 | 1 | map04010 | MAPK signaling pathway |
| 1 | 1 | 1 | 1 | map04012 | ErbB signaling pathway |
| 1 | 1 | 1 | 1 | map04015 | Rap1 signaling pathway |
| 1 | 1 | 1 | 1 | map04020 | Calcium signaling pathway |
| 1 | 1 | 1 | 1 | map04022 | cGMP-PKG signaling pathway |
| 1 | 1 | 1 | 1 | map04024 | cAMP signaling pathway |
| 1 | 1 | 1 | 1 | map04060 | Cytokine-cytokine receptor interaction |
| 1 | 1 | 1 | 1 | map04064 | NF-kappa B signaling pathway |
| 1 | 1 | 1 | 1 | map04066 | HIF-1 signaling pathway |
| 1 | 1 | 1 | 1 | map04068 | FoxO signaling pathway |
| 1 | 1 | 1 | 1 | map04070 | Phosphatidylinositol signaling system |

TABLE 6-continued

Selected Proteomic Pathways Included in all Four Cell Types

| ec relevance | vsmc relevance | mac relevance | lymphocyte relevance | Entry | Name |
|---|---|---|---|---|---|
| 1 | 1 | 1 | 1 | map04071 | Sphingolipid signaling pathway |
| 1 | 1 | 1 | 1 | map04072 | Phospholipase D signaling pathway |
| 1 | 1 | 1 | 1 | map04080 | Neuroactive ligand-receptor interaction |
| 1 | 1 | 1 | 1 | map04110 | Cell cycle |
| 1 | 1 | 1 | 1 | map04115 | p53 signaling pathway |
| 1 | 1 | 1 | 1 | map04120 | Ubiquitin mediated proteolysis |
| 1 | 1 | 1 | 1 | map04137 | Mitophagy - animal |
| 1 | 1 | 1 | 1 | map04141 | Protein processing in endoplasmic reticulum |
| 1 | 1 | 1 | 1 | map04142 | Lysosome |
| 1 | 1 | 1 | 1 | map04144 | Endocytosis |
| 1 | 1 | 1 | 1 | map04145 | Phagosome |
| 1 | 1 | 1 | 1 | map04150 | mTOR signaling pathway |
| 1 | 1 | 1 | 1 | map04151 | PI3K-Akt signaling pathway |
| 1 | 1 | 1 | 1 | map04152 | AMPK signaling pathway |
| 1 | 1 | 1 | 1 | map04210 | Apoptosis |
| 1 | 1 | 1 | 1 | map04211 | Longevity regulating pathway |
| 1 | 1 | 1 | 1 | map04216 | Ferroptosis |
| 1 | 1 | 1 | 1 | map04217 | Necroptosis |
| 1 | 1 | 1 | 1 | map04218 | Cellular senescence |
| 1 | 1 | 1 | 1 | map04310 | Wnt signaling pathway |
| 1 | 1 | 1 | 1 | map04330 | Notch signaling pathway |
| 1 | 1 | 1 | 1 | map04350 | TGF-beta signaling pathway |
| 1 | 1 | 1 | 1 | map04390 | Hippo signaling pathway |
| 1 | 1 | 1 | 1 | map04512 | ECM-receptor interaction |
| 1 | 1 | 1 | 1 | map04550 | Signaling pathways regulating pluripotency of stem cells |
| 1 | 1 | 1 | 1 | map04614 | Renin-angiotensin system |
| 1 | 1 | 1 | 1 | map04620 | Toll-like receptor signaling pathway |
| 1 | 1 | 1 | 1 | map04668 | TNF signaling pathway |
| 1 | 1 | 1 | 1 | map04710 | Circadian rhythm |
| 1 | 1 | 1 | 1 | map04722 | Neurotrophin signaling pathway |
| 1 | 1 | 1 | 1 | map04910 | Insulin signaling pathway |
| 1 | 1 | 1 | 1 | map04912 | GnRH signaling pathway |
| 1 | 1 | 1 | 1 | map04919 | Thyroid hormone signaling pathway |
| 1 | 1 | 1 | 1 | map04924 | Renin secretion |
| 1 | 1 | 1 | 1 | map07046 | Immunosuppressive agents |
| 1 | 1 | 1 | 1 | map07051 | Antidiabetics |

Table 7 below lists pathways important for lipid lowering. A high number listed in the "lipid significance" column means that the pathway is highly significant, a low number means low significance.

TABLE 7

Top Lipid-related Pathways

| Lipid Significance | KEGG Map Entry No. | Pathway Name |
|---|---|---|
| 120 | map05417 | Lipid and atherosclerosis |
| 64 | map04979 | Cholesterol metabolism |
| 64 | map04923 | Regulation of lipolysis in adipocytes |
| 48 | map04060 | Cytokine-cytokine receptor interaction |
| 48 | map04064 | NF-kappa B signaling pathway |
| 48 | map04668 | TNF signaling pathway |
| 48 | map04910 | Insulin signaling pathway |
| 38 | map05418 | Fluid shear stress and atherosclerosis |
| 36 | map04670 | Leukocyte transendothelial migration |
| 36 | map04911 | Insulin secretion |
| 36 | map04933 | AGE-RAGE signaling pathway in diabetic complications |
| 32 | map04010 | MAPK signaling pathway |
| 32 | map04145 | Phagosome |
| 32 | map04614 | Renin-angiotensin system |
| 32 | map07046 | Immunosuppressive agents |
| 24 | map04657 | IL-17 signaling pathway |
| 20 | map04750 | Inflammatory mediator regulation of TRP channels |
| 16 | map00010 | Glycolysis/Gluconeogenesis |

TABLE 7-continued

Top Lipid-related Pathways

| Lipid Significance | KEGG Map Entry No. | Pathway Name |
|---|---|---|
| 16 | map04141 | Protein processing in endoplasmic reticulum |
| 16 | map04150 | mTOR signaling pathway |
| 16 | map04152 | AMPK signaling pathway |
| 16 | map04211 | Longevity regulating pathway |
| 16 | map07051 | Antidiabetics |
| 12 | map04062 | Chemokine signaling pathway |
| 12 | map04920 | Adipocytokine signaling pathway |
| 12 | map04371 | Apelin signaling pathway |
| 10 | map04931 | Insulin resistance |

Table 8 below lists pathways important for anti-inflammation. A high number listed in the "inflammation significance" column means that the pathway is highly significant, a low number means low significance.

TABLE 8

Top Inflammation-related Pathways

| Inflammation Significance | KEGG Map Entry No. | Pathway Name |
|---|---|---|
| 96 | map04060 | Cytokine-cytokine receptor interaction |
| 96 | map04064 | NF-kappa B signaling pathway |
| 96 | map04668 | TNF signaling pathway |
| 80 | map04910 | Insulin signaling pathway |
| 72 | map05417 | Lipid and atherosclerosis |
| 72 | map04670 | Leukocyte transendothelial migration |
| 64 | map04010 | MAPK signaling pathway |
| 64 | map04145 | Phagosome |
| 64 | map04614 | Renin-angiotensin system |
| 64 | map07046 | Immunosuppressive agents |
| 60 | map04911 | Insulin secretion |
| 60 | map04933 | AGE-RAGE signaling pathway in diabetic complications |
| 48 | map04657 | IL-17 signaling pathway |
| 40 | map04750 | Inflammatory mediator regulation of TRP channels |
| 24 | map04062 | Chemokine signaling pathway |
| 24 | map04920 | Adipocytokine signaling pathway |
| 20 | map05418 | Fluid shear stress and atherosclerosis |
| 16 | map00010 | Glycolysis/Gluconeogenesis |
| 16 | map04141 | Protein processing in endoplasmic reticulum |
| 16 | map04150 | mTOR signaling pathway |
| 16 | map04152 | AMPK signaling pathway |
| 16 | map04211 | Longevity regulating pathway |
| 16 | map07051 | Antidiabetics |
| 16 | map04931 | Insulin resistance |
| 16 | map04979 | Cholesterol metabolism |
| 16 | map04923 | Regulation of lipolysis in adipocytes |
| 16 | map04660 | T cell receptor signaling pathway |
| 12 | map04371 | Apelin signaling pathway |
| 12 | map04658 | Th1 and Th2 cell differentiation |
| 12 | map04659 | Th17 cell differentiation |
| 12 | map04662 | B cell receptor signaling pathway |

Table 9 below lists pathways important for anti-diabetes. A high number listed in the "diabetes significance" column means that the pathway is highly significant, a low number means low significance.

TABLE 9

Top Diabetes-related Pathways

| Diabetes Significance | KEGG Map Entry No. | Pathway Name |
|---|---|---|
| 80 | map04910 | Insulin signaling pathway |
| 64 | map00010 | Glycolysis/Gluconeogenesis |
| 64 | map04141 | Protein processing in endoplasmic reticulum |
| 64 | map04150 | mTOR signaling pathway |
| 64 | map04152 | AMPK signaling pathway |
| 64 | map04211 | Longevity regulating pathway |
| 64 | map07051 | Antidiabetics |
| 60 | map04911 | Insulin secretion |
| 60 | map04933 | AGE-RAGE signaling pathway in diabetic complications |
| 48 | map04371 | Apelin signaling pathway |
| 36 | map05417 | Lipid and atherosclerosis |
| 24 | map04060 | Cytokine-cytokine receptor interaction |
| 24 | map04064 | NF-kappa B signaling pathway |
| 24 | map04668 | TNF signaling pathway |
| 19 | map04931 | Insulin resistance |
| 18 | map04670 | Leukocyte transendothelial migration |
| 16 | map04010 | MAPK signaling pathway |
| 16 | map04145 | Phagosome |
| 16 | map04614 | Renin-angiotensin system |
| 16 | map07046 | Immunosuppressive agents |
| 16 | map04979 | Cholesterol metabolism |
| 16 | map04923 | Regulation of lipolysis in adipocytes |
| 16 | map04940 | Type I diabetes mellitus |
| 12 | map04657 | IL-17 signaling pathway |
| 11 | map05418 | Fluid shear stress and atherosclerosis |
| 10 | map04750 | Inflammatory mediator regulation of TRP channels |

To exemplify, the KEGG pathway HSA05417 contains unique pathways for three of the cell types modelled in this work (ECs, VSMCs, and macrophages), plus the plasma compartment. In other words, pathway HSA5417 is one of the ones that is broken into cell-type specific pieces. In particular, the relations summarizing the products from low-density lipoprotein (LDL) into oxidized LDL (oxLDL), glycated LDL (glyLDL), and minimally modified LDL (mmLDL) were identified in terms of relations with proteins in the tissue (see, Kanehisa, M.; "Post-genome Informatics", Oxford University Press (2000); Otsuka et al., Pathology of coronary atherosclerosis and thrombosis. *Cardiovasc Diagn Ther* 6, 396-408, doi:10.21037/cdt.2016.06.01 (2016)).

HSA04514 ("Cell Adhesion Molecules") similarly contains pathway information for three modelled cell types (ECs, lymphocytes, and macrophages) with content split accordingly. HSA04514 is another pathway that is broken into cell-type specific pieces.

HSA04640, "Hematopoietic Cell Lineage" was split to remove content irrelevant for the cell types modelled in our work.

HSA04670, "Leukocyte Transendothelial Migration" splits the EC portion from the leukocyte portion, where two of the cell types modelled in this study were leukocytes (macrophages and lymphocytes).

HSA04931, "Insulin Resistance," is included both in VSMCs, needed for our study, and also in liver, not used in our study.

Likewise, some pathways included content relating to the plasma-tissue boundary as noted.

The resulting set of pathways was integrated into cell networks at three scopes: "core," "mid," "full," utilizing a program to split .kgml files by cell type. "Core" networks included pathways unique to each respective cell type. "Mid" included pathways shared by one other cell type. "Full" included pathways shared by these and other human cell types, being in general associated with mammalian cell function. The selected pathways at each scope for each cell type were merged into a cytoscape representation using BioNSi (Biological Network Simulator)(Shalhoub, J. et al. Systems biology of human atherosclerosis. *Vascular and endovascular surgery* 48, 5-17 (2014); Fava, C. & Montagnana, M., Atherosclerosis is an inflammatory disease, which lacks a common anti-inflammatory therapy: how human genetics can help to this issue. A narrative review. *Frontiers in pharmacology* 9, 55 (2018)), however, overriding the edge weights to allowed a richer set of relations than otherwise supported by BioNSi. The generated node lists were then compared against available plaque protein measurements from our cohort. Proteins where no direct experimental measurement was available and having no incoming edges were pruned.

BioNSi is a tool for modeling biological networks and simulating their discrete-time dynamics, implemented as a Cytoscape app. BioNSi includes a visual representation of the network that enables researchers to construct, set the parameters, and observe network behavior under various conditions. In particular, specifics on the use of BioNSi names to signify LDL products in the methods described herein include (this is not the way BioNSi is normally intended, but is used here as a means to represent a more granular biochemistry as needed to support the simulations described herein):

1. glyLDL is reflected as glycosylation of LDL, as a correct representation
2. oxLDL is reflected as binding/association, not because it is the correct name, but rather that the weight is 1, indicating that a fraction gets converted, and that oxLDL is the smallest fraction
3. mmLDL is reflected as state change, not because it is the correct name, but rather that the weight is 3, justified as Levitan 2010 indicating that a fraction gets converted, and that mmLDL is a higher fraction than ox
4. VLDL is reflected as indirect effect, not because it is the correct name, but rather that the weight is 2, justified as VLDL being estimated as TG/5, with 93 patients having both TG and LDL, had an average level of 15% of LDL (as a best-effort approximation).

FIG. 10 shows HSA05417, "Lipid and Atherosclerosis," which contains unique pathways for three of the cell types modeled in this work (EC, VSMC, and macrophages), plus good detail in the plasma compartment. In particular, the relations summarizing the products from LDL into oxidized LDL (oxLDL), glycated LDL (glyLDL), and minimally are identified in terms of relations with proteins in the tissue. Adapted from the KEGG database for pathway HSA05417 (Kanehisa, M. and Goto, S.; KEGG: Kyoto Encyclopedia of Genes and Genomes. Nucleic Acids Res. 28, 27-30 (2000); Kanehisa, M; Toward understanding the origin and evolution of cellular organisms. Protein Sci. 28, 1947-1951 (2019); Kanehisa, M., Furumichi, M., Sato, Y., Ishiguro-Watanabe, M., and Tanabe, M.; KEGG: integrating viruses and cellular organisms. Nucleic Acids Res. 49, D545-D551 (2021)).

Table 10, below shows detailed BioNSi edge mappings on import.

TABLE 10

Specific Mappings used to Achieve Result

| Name | Weight | Visual appearance |
| --- | --- | --- |
| Activation | 10 | --> (solid, arrow) |
| inhibition | -10 | --| (solid, T) |
| indirect effect | 2 | ..> (dash, arrow) |
| state change | 3 | ... (sinewave) |
| binding/association | 1 | --- (parallel lines) |
| dissociation | -1 | -+- (zigzag) |
| missing interaction | 0 | -/- (dots) |
| phosphorylation | 4 | +p (forward slash) |
| dephosphorylation | -4 | -p (backward slash) |
| glycosylation | 5 | +g (contiguous arrow) |
| ubiquitination | -7 | +u (solid, cross delta) |
| methylation | 6 | +m (separate arrow) |

BioNSi import also adds self-inhibition loops (-9) but they can be deleted when used without transcriptomic data, or can represent the transcription/translation process when both proteomics and transcriptomics data are used.

Figure 11:
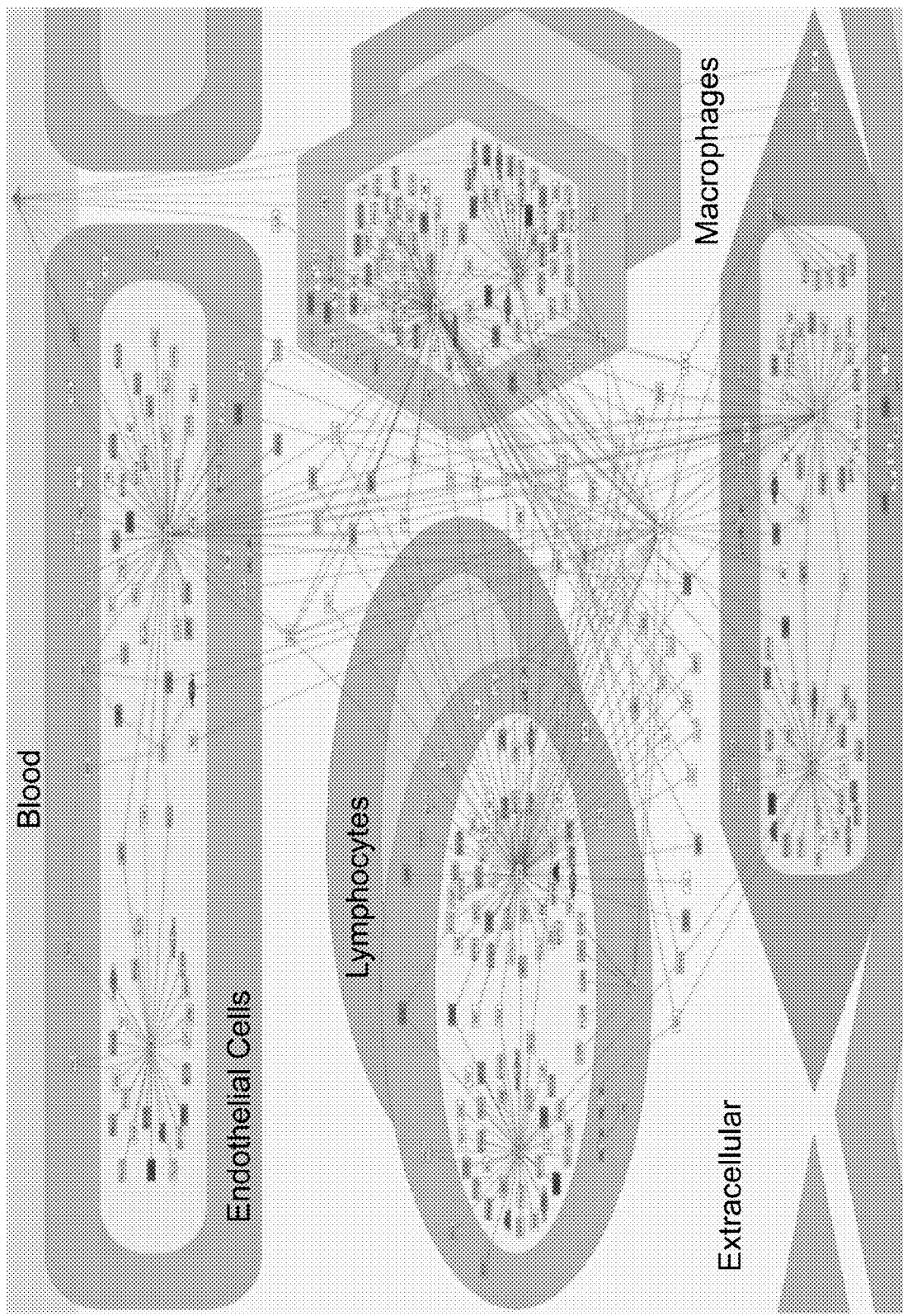
FIG. 11 is a schematic diagram that shows first level targets of an unstable subject at baseline (subject P491), represented in a layout that highlights compartmentalization with plasma (pink hue) with serum LDL indicated to reflect relations with proteins in the plasma membranes of Endothelial Cells (green), macrophages (orange), VSMCs (aquamarine), lymphocytes (blue) and in the extracellular region. Specific compartments and cell types shown are examples, without loss of generality.

In addition, networks for the integrated intima were created by compartmentalizing proteins into the intracellular of each cell type, the cell membranes, the extracellular space, with a separate compartment for the blood (See, FIG. 11). Specifically, in FIG. 11, first level targets of an unstable patient at baseline (patient P491), is represented in a layout that highlights compartmentalization with plasma (pink hue) with serum LDL indicated to reflect relations with proteins in the plasma membranes of ECs (green), macrophages (orange), VSMCs, (aquamarine), and in the extracellular region. A large majority of proteins were well compartmentalized with approximately 15% localized to the extracellular region. The intima network included 4411 proteins, after compartmentalization it was observed that as many as 1446 were localized to multiple cell compartments (FIGS. 11 and 12).

Figure 12:
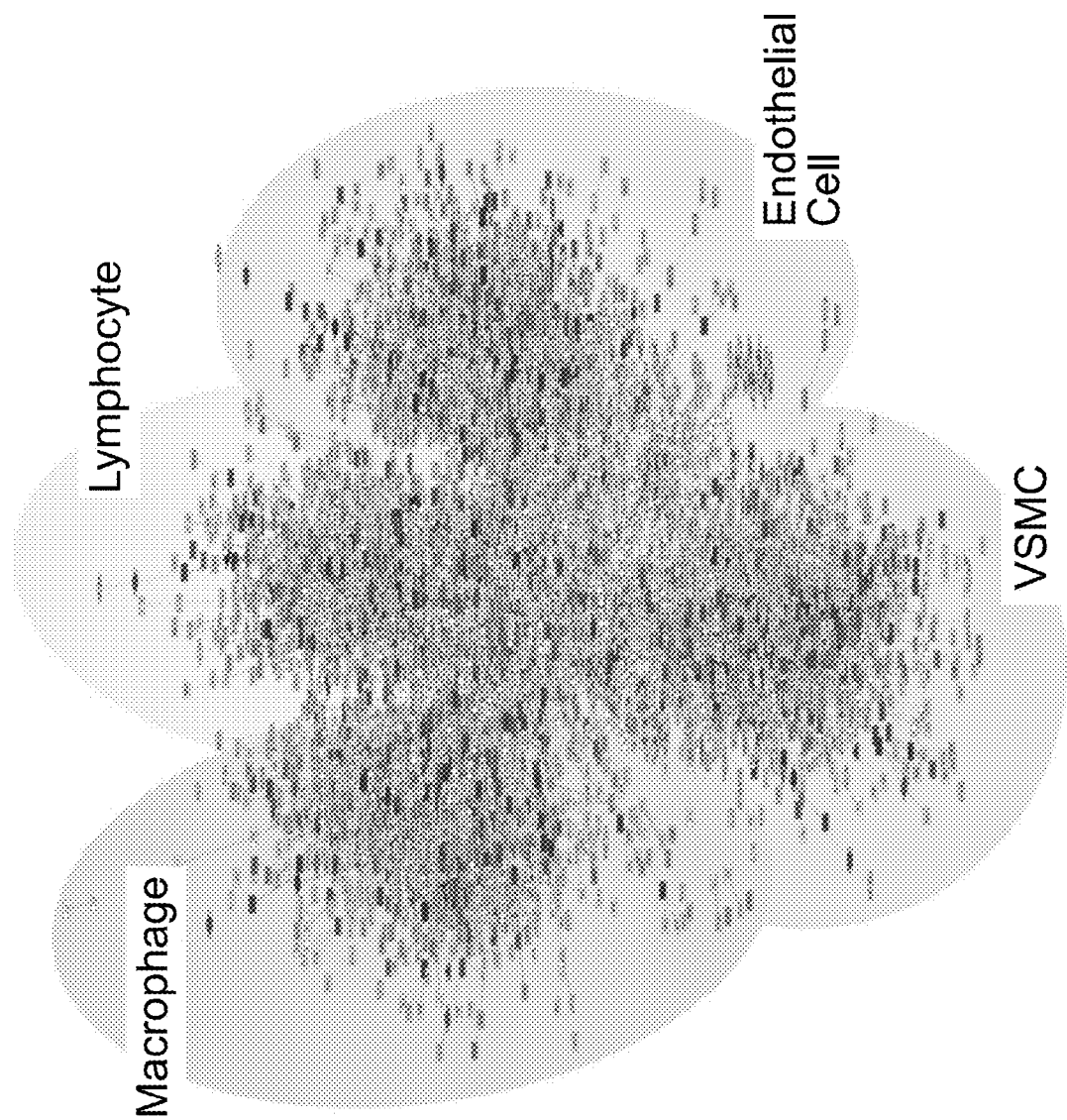
FIG. 12 is an image showing the integrated intima network at "full" scope for an unstable subject (subject P491) in an untreated or baseline condition. We note that other integrated networks, such as for the adventitia, media, or perivascular space can also be used without loss of generality.

Specifically, FIG. 12 shows the integrated intima network at "full" scope for an unstable patient (patient P491) in an untreated or baseline condition.

Example 2: Per-Patient Calibrated Networks

Given the network definitions thus created, the proteomic data was used to update networks using calibration data from each patient. Approximately 50% of the proteins in the networks were actually measured within the proteomic dataset. Since the pathways cover all selected protein-protein interactions in the pathway, estimation of protein levels for those lacking measurement in the dataset required interpolation. A total of 540 personalized networks were calibrated: 2 for each of the 18 patients at each cell type, integrated intima, and at each of the three scopes, respectively, comprising the entire database of protein level vectors referred to as "exemplars." The database of exemplars demonstrated large variation in proteomic signatures after individual test patient calibration, corresponding to an estimated range of 39-96% plaque instability in the baseline condition.

Pseudo-code for the algorithm is outlined as follows:
Set true plaque phenotype from histology (minimal, stable, unstable)

Figure 13A:
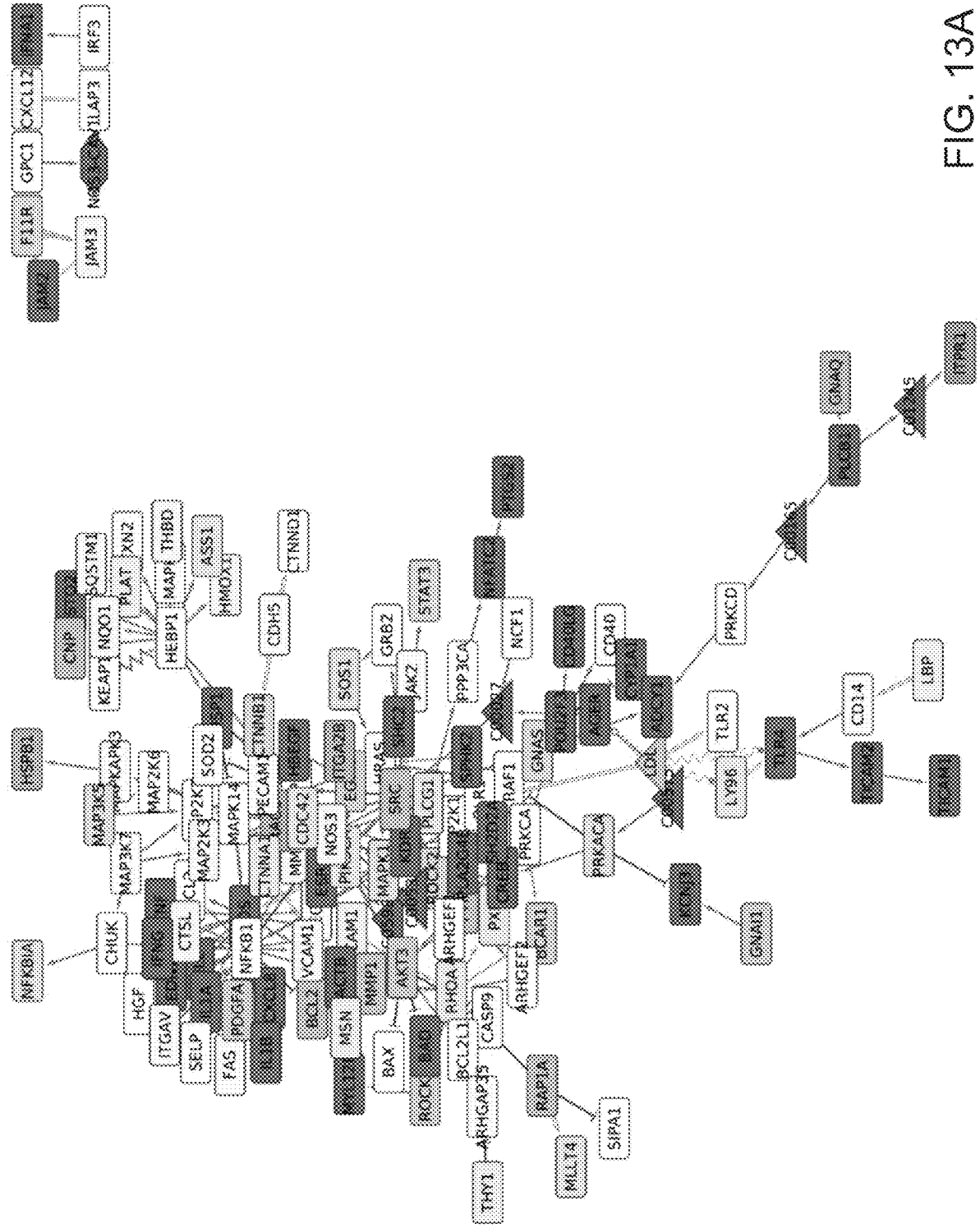
FIGS. 13A and 13B are images showing individual subject calibration.
Figure 13B:
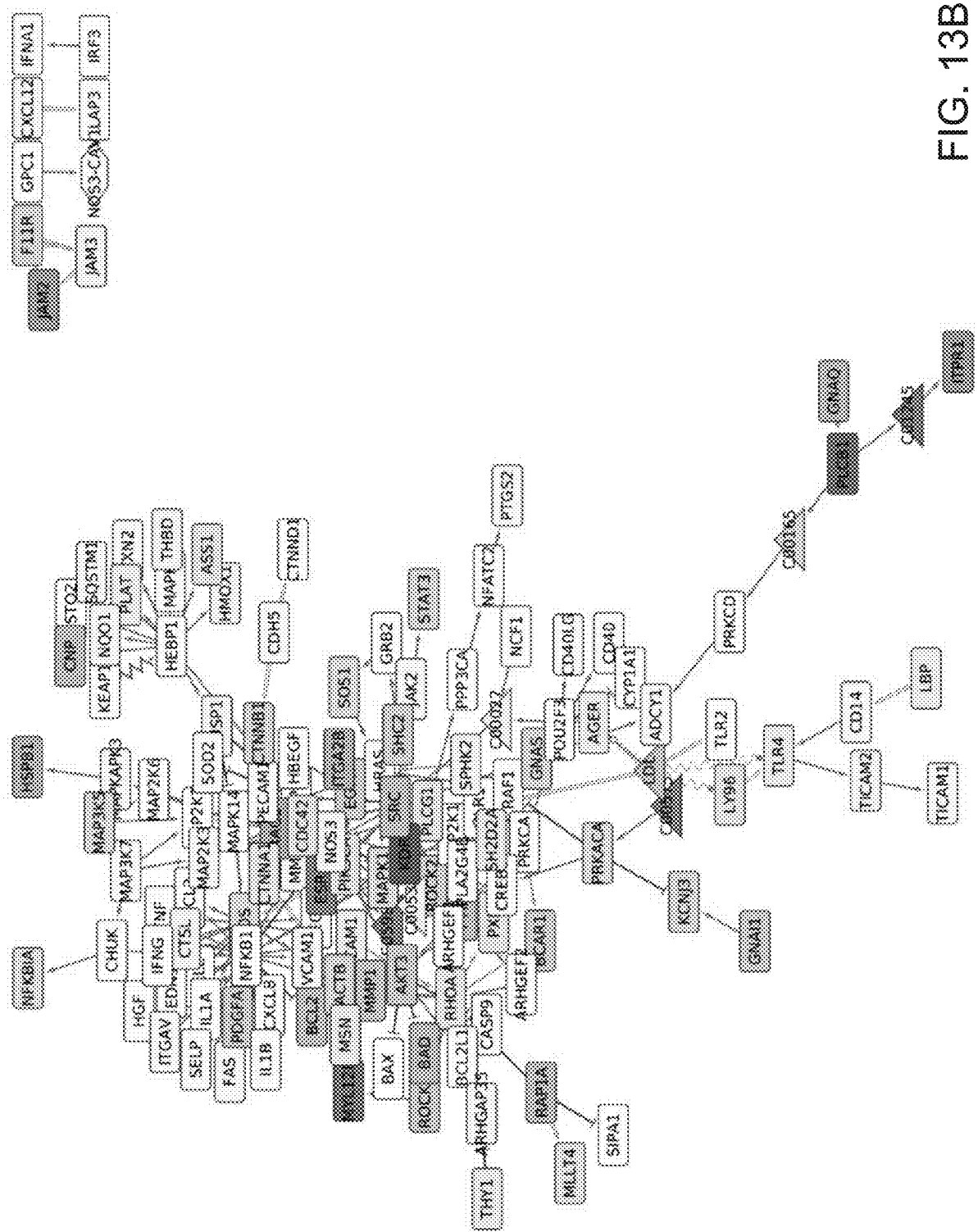

Load protein levels
Interpolate missing protein levels by iterating until achieving a high similarity (cosine similarity metric as a measure of convergence):
 For each node that is not fixed:
  For each edge, record suggestion (negating weights from outgoing edges):
   If the weight is negative (e.g., inhibition) if the source is less than the mean, unweighted suggestion is formed to pull down the target by a modest amount, or if the source is above the mean, to pull the target correspondingly down
   Else (e.g., activation), if the source is less than the mean, unweighted suggestion is formed to raise the target modestly, or if greater than the mean, to raise it correspondingly more
  Create a weighted mean (handling missing values)
  Record the result and iterate for overall convergence (handling lack of convergence)
Save protein levels An example of a visualization of individual patient calibration molecules is shown in FIGS. 13A and 13B. FIG. 13A is a map (originally in color) that represents those molecules that had direct measurements for the EC core network. Specifically, some molecules show high expression (or red), some show low expression (or blue), and for some molecules direct measurements were not available (green). FIG. 13B represents interpolated values that demonstrate propagation of levels from non-interpolated proteins according to type and weight of relation drawn from the pathway specification.

Clustering analysis performed on the calibrated networks identified proteins with high variance for each cell type and scope. By way of example, the proteins with the highest variance between unstable plaque, stable plaque, and minimal disease at the core scope for ECs were interstitial collagenase (MMP1), lipopolysaccharide-binding protein (LBP), advanced glycosylation end product-specific receptor (RAGE), and integrin alpha-IIb (ITGA2B). At the mid scope, proteins such as TLR4 and HMOX1 also demonstrated large differences. For the mid scope networks, VSMCs showed strong separation in proteins such as tumour protein (p53), mothers against decapentaplegic homolog 2 (SMAD2), and coagulation factor VIII (F8), macrophages in proteins such as lipocalin 2 (LCN2), S100 calcium binding protein (S100A8/9), and cyclin dependent kinase inhibitor 1A (CDKN1A). In lymphocytes, matrix metalloproteinases (MMP1/9), insulin like growth factor binding protein acid labile subunit (IGFALS), and solute carrier family 2 (SLC2A1) were separated, whereas the integrated intima showed strong separation in proteins such as SMAD2 and S100A9 across cell types and interleukin 23 Receptor (IL23R) in lymphocytes.

Specifically, FIGS. 14-18 are heatmaps identifying the top 25 proteins in terms of variance among the signatures in the experimental cohort for various cells. In each of the heat maps, expression levels of various proteins are shown (red for high expression; blue for low expression).

Figure 14:
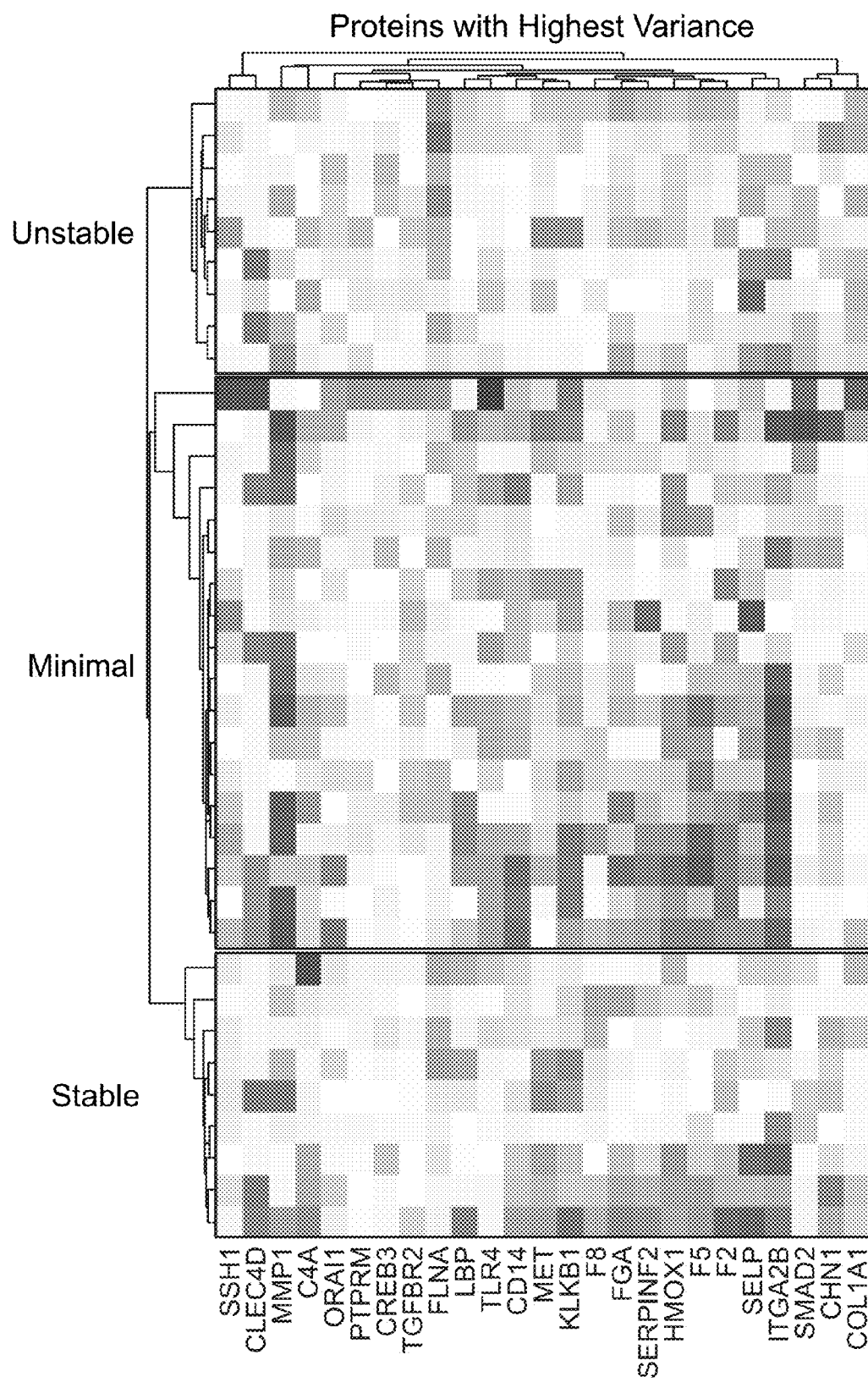
FIG. 14 is a heatmap identifying the top 25 proteins in terms of variance among the signatures in an experimental cohort as described herein, in this case for the endothelial cell, mid scope network. This heatmap is shown as an example, other cell types, network scopes, or protein levels are to be understood without loss of generality.

FIG. 14 is a heatmap identifying the top 25 proteins in terms of variance among the signatures in our experimental cohort, in this case for the endothelial cell, mid scope network. Strong separation in proteins such as MMP1, TLR4, HMOX1, and others is evident.

Figure 15:
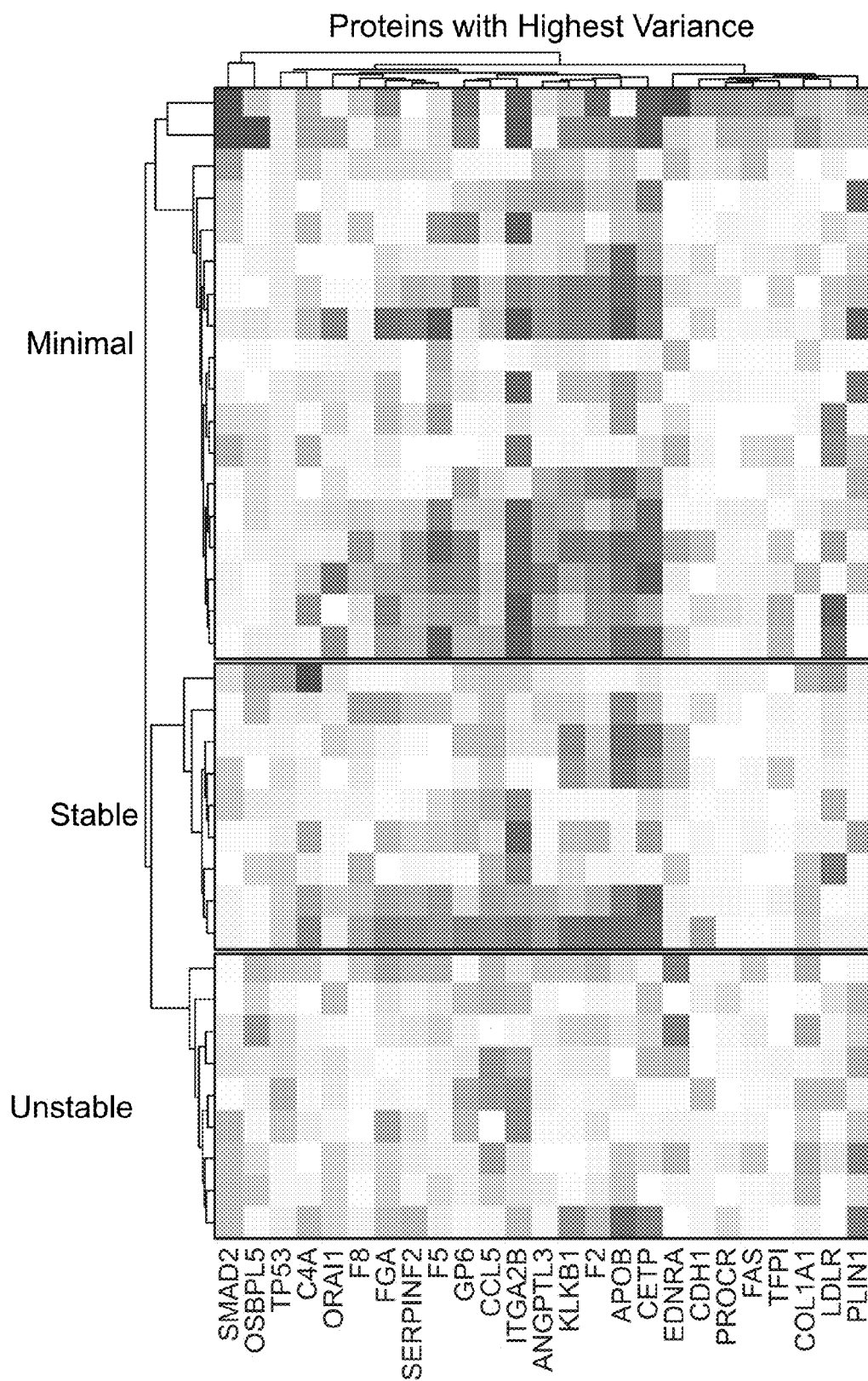
FIG. 15 is a heatmap identifying the top 25 proteins in terms of variance among the signatures in our experimental cohort, in this case for the VSMC, mid scope network. This heatmap is shown as an example, other cell types, network scopes, or protein levels are to be understood without loss of generality.

FIG. 15 is a heatmap identifying the top 25 proteins in terms of variance among the signatures in our experimental cohort, in this case for the VSMC, mid scope network. Strong separation in proteins such asTP53, SMAD2, F8, and others is evident. Note, classical markers for the cell types are not the focus, rather, those proteins with large variation in levels across the levels of instability.

Figure 16:
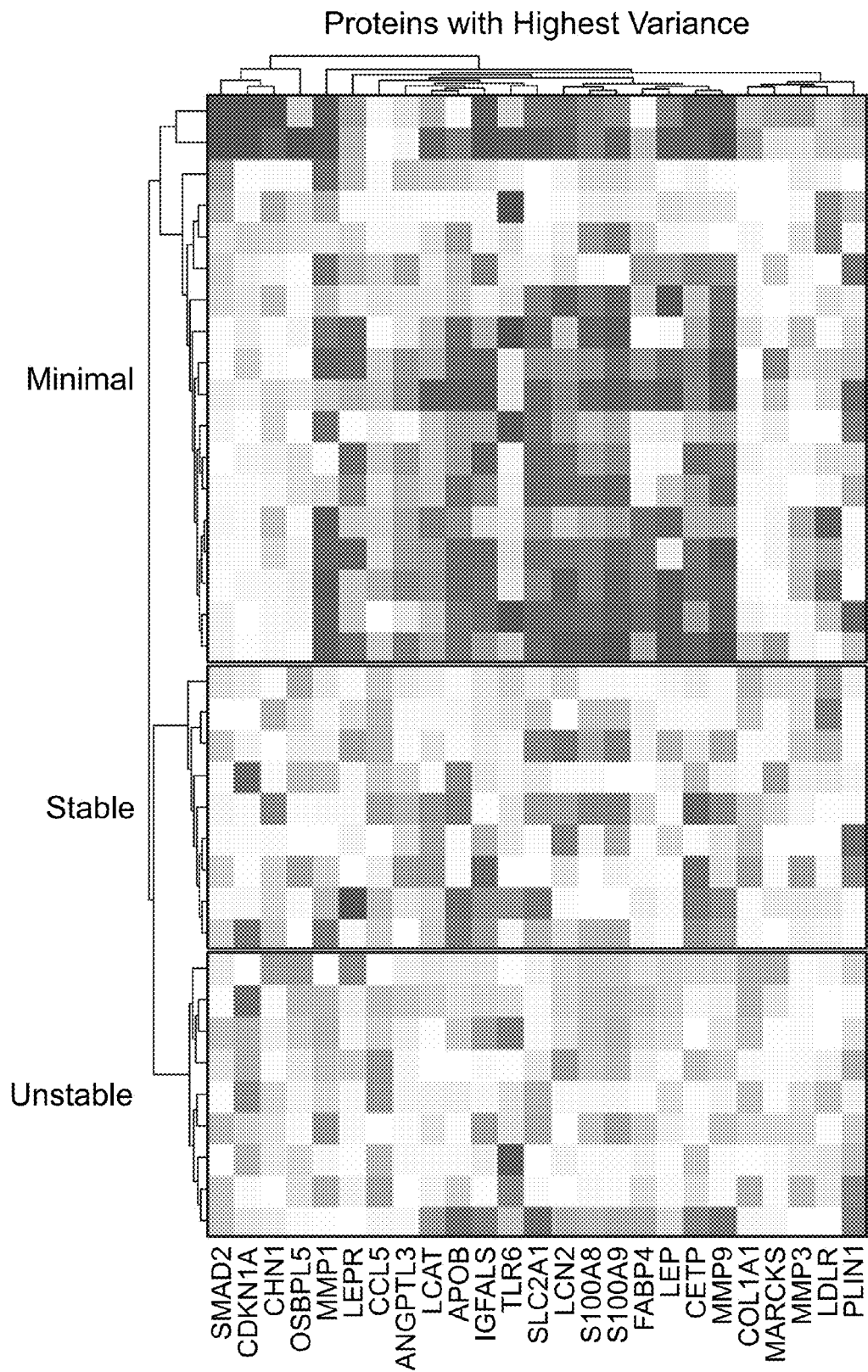
FIG. 16 is a heatmap identifying the top 25 proteins in terms of variance among the signatures in our experimental cohort, in this case for the macrophage, mid scope network. This heatmap is shown as an example, other cell types, network scopes, or protein levels are to be understood without loss of generality.

FIG. 16 is a heatmap identifying the top 25 proteins in terms of variance among the signatures in our experimental cohort, in this case for the macrophage, mid scope network. Strong separation in proteins such asLCN2, S100A8/9, CDKN1A, and others is evident. Note, classical markers for the cell types are not the focus, rather, those proteins with large variation in levels across the levels of instability.

Figure 17:
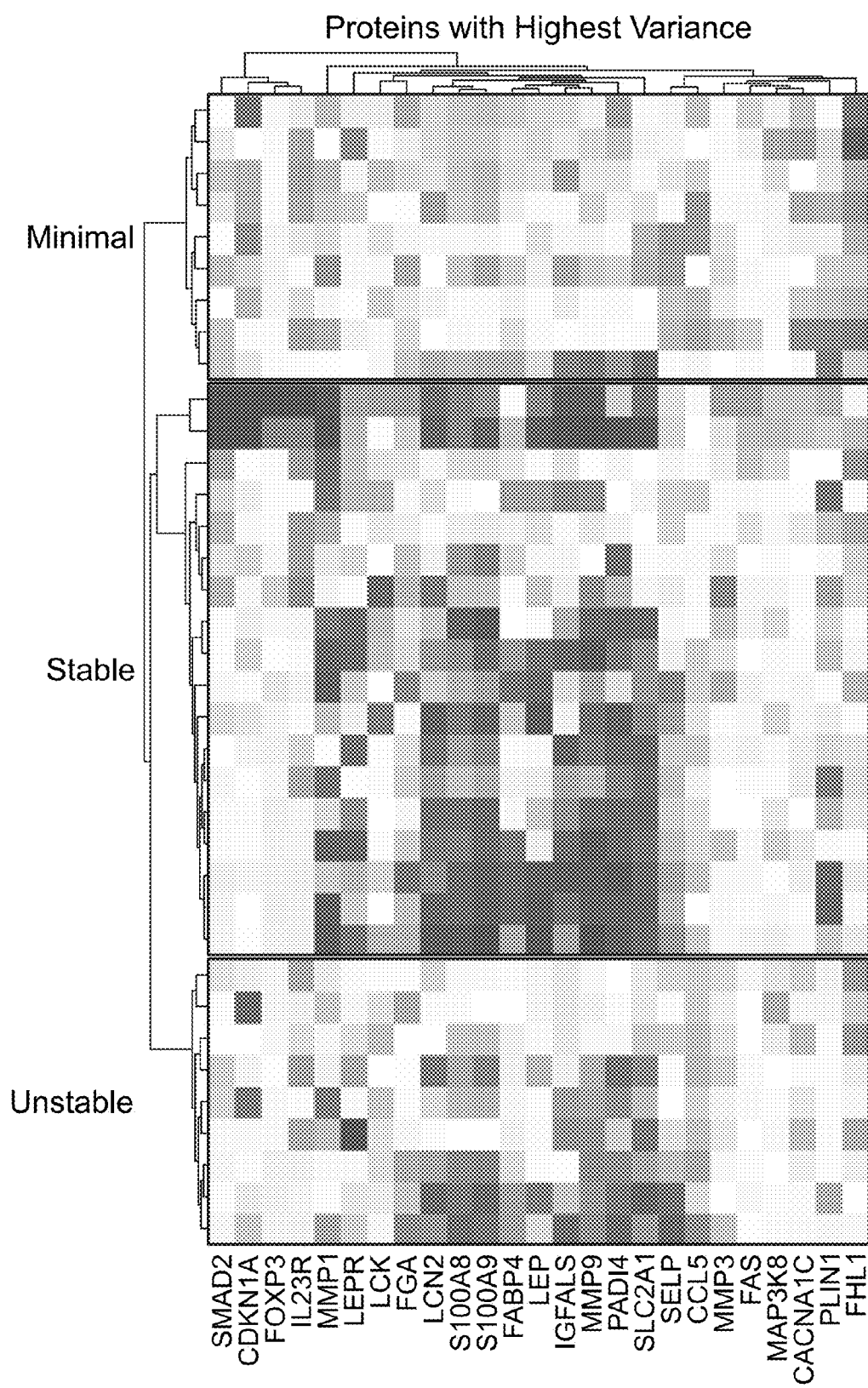
FIG. 17 is a heatmap identifying the top 25 proteins in terms of variance among the signatures in our experimental cohort, in this case for the lymphocyte, mid scope network. This heatmap is shown as an example, other cell types, network scopes, or protein levels are to be understood without loss of generality.

FIG. 17 is a heatmap identifying the top 25 proteins in terms of variance among the signatures in our experimental cohort, in this case for the lymphocyte, mid scope network. Strong separation in proteins such asMMP1/9, IGFALS, SLC2A1, and others is evident. Note, classical markers for the cell types are not the focus, rather, those proteins with large variation in levels across the levels of instability.

Figure 18:
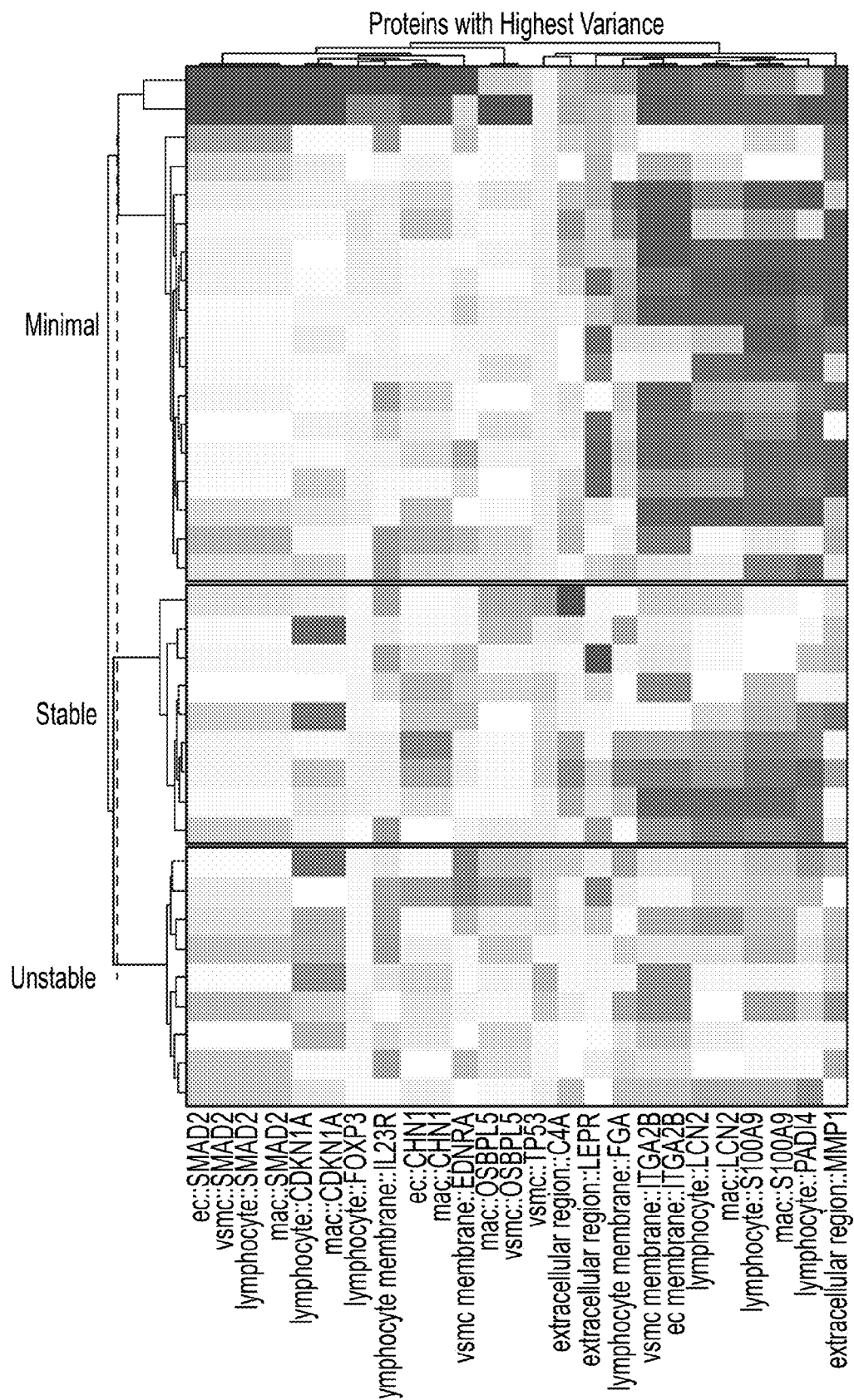
FIG. 18 is a heatmap identifying the top 25 proteins in terms of variance among the signatures in our experimental cohort, in this case for the intima, mid-scope network. This heatmap is shown as an example, other cell types, network scopes, or protein levels are to be understood without loss of generality.

FIG. 18 is a heatmap identifying the top 25 proteins in terms of variance among the signatures in our experimental cohort, in this case for the intima, mid-scope network. Strong separation in proteins such asSMAD2 and S100A9 (across cell types), IL23R (in the lymphocytes), and several in the extracellular region is evident. Stable clusters between unstable and minimal. Note, classical markers for the cell types are not the focus, rather, the focus is on those proteins with large variation in levels across the levels of instability.

Example 3: Treatment Dependent Network Perturbations

Based on the identified proteins from the clustering results, plaque instability in this cohort was found to be mainly driven by networks coupled to endothelial dysfunction, modulated immune system responses, and inflammation at a range of degrees. Consequently, we simulated treatments with intensive lipid lowering (Sawada et al., From unbiased transcriptomics to understanding the molecular basis of atherosclerosis. *Current Opinion in Lipidology* 32, 328-329, doi:10.1097/mo1.0000000000000773 (2021)) an IL 1β antagonist as an example anti-inflammatory drugs (Alimohammadi et al., Development of a Patient-Specific Multi-Scale Model to Understand Atherosclerosis and Calcification Locations: Comparison with In vivo Data in an Aortic Dissection. *Front Physiol* 7, 238, doi:10.3389/fphys.2016.00238 (2016)), and an anti-diabetic agent, with hypothesized effects in treatment of atherosclerosis (Corti, A. et al. Multiscale Computational Modeling of Vascular Adaptation: A Systems Biology Approach Using Agent-Based Models. *Front Bioeng Biotechnol* 9, 744560, doi: 10.3389/fbioe.2021.744560 (2021); Casarin et al., A Computational Model-Based Framework to Plan Clinical Experiments—an Application to Vascular Adaptation Biology. *Comput Sci ICCS* 10860, 352-362, doi:10.1007/978-3-319-93698-7_27 (2018)).

The intensive lipid lowering treatment was modelled by decreasing the patient's LDL level by 25% constrained by a minimal value to represent clinically reported effects of such therapies (Morgan et al., Mathematically modelling the dynamics of cholesterol metabolism and ageing. *Biosystems* 145, 19-32, doi:10.1016/j.biosystems. 2016.05.001 (2016)). For plasma lipids, we modelled LDL products (Otsuka et al., Pathology of coronary atherosclerosis and thrombosis. *Cardiovasc Diagn Ther* 6, 396-408, doi:10.21037/cdt.2016.06.01 (2016)) including glycosylated (glyLDL), oxidised (oxLDL), and minimally-modified (mmLDL), and VLDL. Specifics on LDL products are outlined above.

Figure 19A:
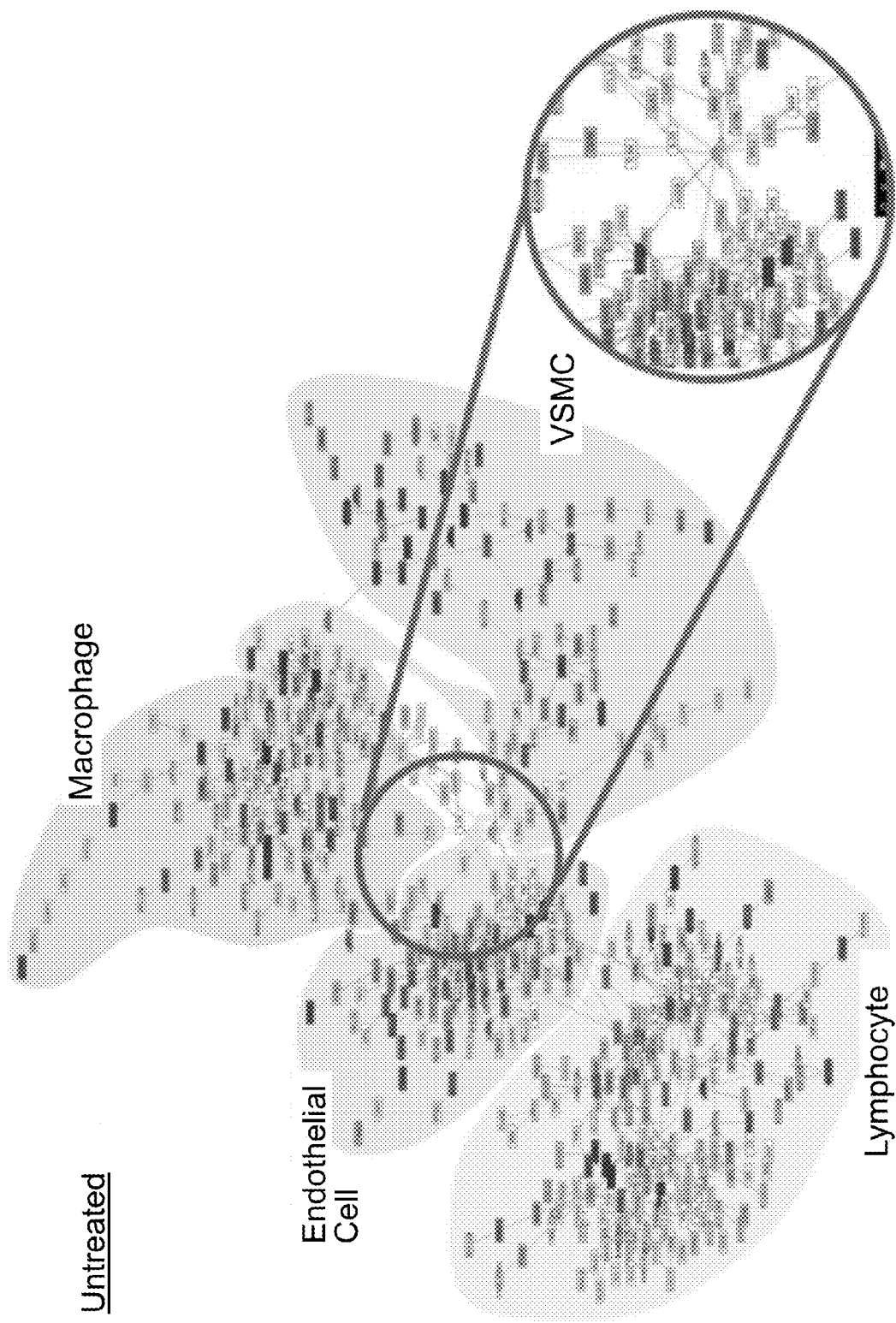
FIGS. 19A and 19B are illustrations of an intima model at the "core" scope before and after simulation of treatment with intensive lipid lowering. This heatmap is shown as an example, other cell types, network scopes, or candidate treatments are to be understood without loss of generality.
Figure 19B:
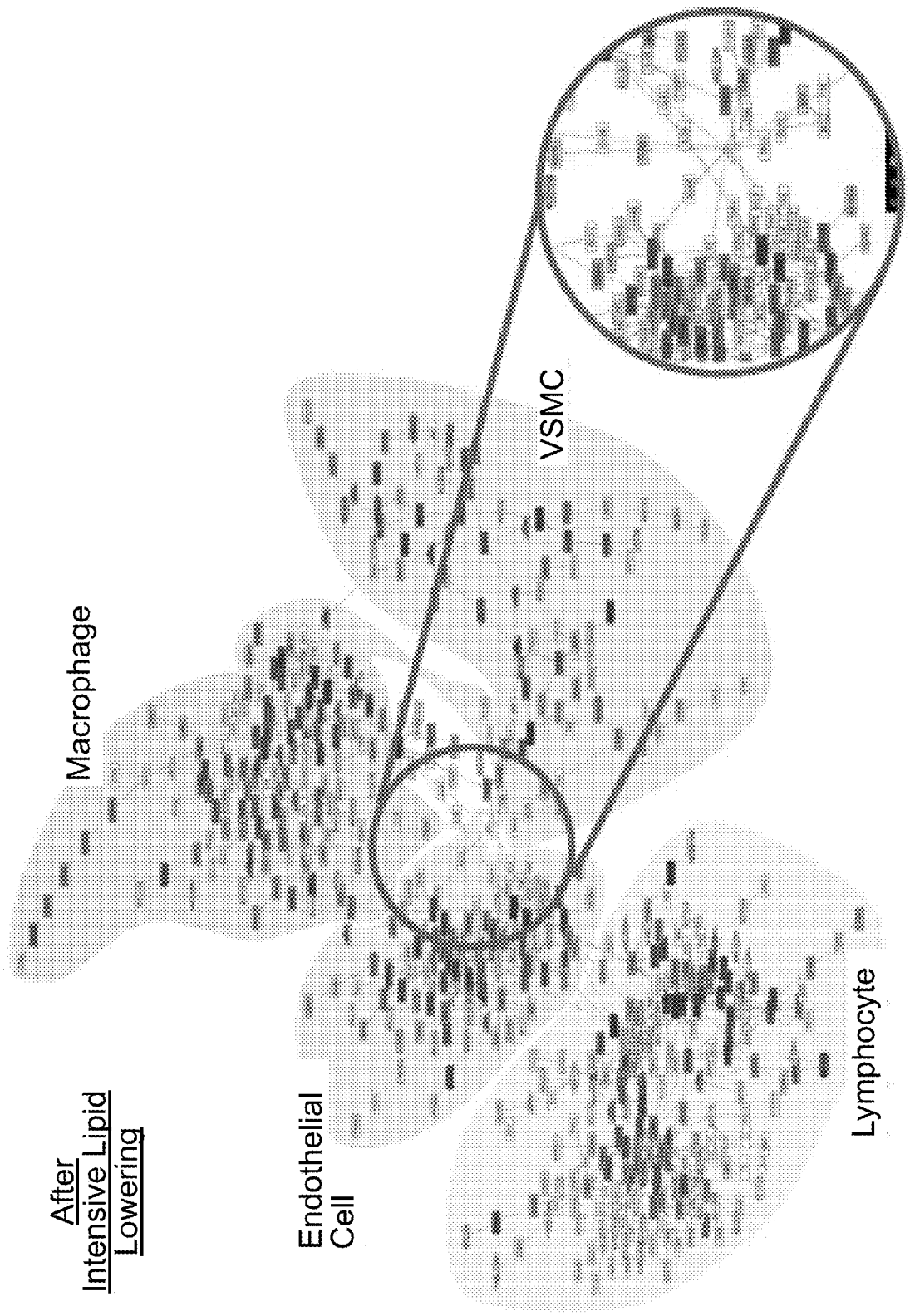

FIGS. 19A-19B is an illustration of the intima model at the "core" scope before and after simulation of treatment with intensive lipid lowering. The "untreated or baseline" panel, shown in FIG. 19A indicates protein levels after calibration for the unstable patient in FIGS. 3A and 3D. LDL is at the center of the layout, and both direct as well as indirect effects of lowering LDL levels by simulated therapy can be identified. Simulations with intensive lipid lowering demonstrated changes in protein levels stemming from the decrease in LDL level and its end products (e.g., oxLDL), both with respect to directly affected proteins as well effects propagated through networks. Intensive lipid lowering was seen to decrease the levels of many proteins related to plaque instability, while increasing some proteins estimated to confer stability (FIG. 19B).

The anti-inflammatory treatment was modeled by holding IL1β level to a minimum level observed across proteins in the dataset. The anti-diabetic treatment was modelled by holding MTOR, NFKβ1, ICAM1, and VCAM1 (based on documented effects of Metformin) to the minimum level observed across proteins in the dataset (Ally et al., Role of neuronal nitric oxide synthase on cardiovascular functions in physiological and pathophysiological states. Nitric Oxide 102, 52-73 (2020); Parton et al., New models of atherosclerosis and multi-drug therapeutic interventions. *Bioinformatics* 35, 2449-2457, doi:10.1093/bioinformatics/bty980 (2018)). "Minimum level" refers to the lowest number in the test subject data across molecules, determined as a function of the process.

The results from this specific example showed that simulation with intensive lipid lowering therapy was generally the most effective at decreasing plaque instability, with marginal improvement in simulated combination therapy. Anti-inflammatory and anti-diabetic therapies provided mixed results from patient to patient, manifesting as overall inferior performance compared with intensive lipid lowering. The combination therapy that included intensive lipid lowering and an anti-diabetic drug was in general the best for patients starting out from highly unstable proteomic signatures. This example illustrates that the invention can be an effective strategy for selected patients. Moreover, the fact that some initially unstable patients did not show appreciable response to the simulated pharmacotherapies suggested an ability of the modelling approach to identify individuals best treated surgically rather than medically. Patients with initially stable signatures showed less improvement by the simulated therapies, indicating sufficient preventive efficacy on standard medical treatment alone. In addition, some patients starting with unstable signatures did not benefit from simulated pharmacotherapy and should likely receive preventive surgery, suggesting a potential of the modelling approach to identify high-risk individuals and improve decision making between procedural intervention and pharmacotherapy. The individualized patient treatment recommendations differed widely across patients, highlighting the importance of individual predictions and more refined patient stratifications, as enabled by the defined systems biology model of our study. Given the dominating inflammatory proteomic signature of unstable plaques, the subtle effects observed by simulation with anti-inflammatory therapy are worth considering. This finding may be due to the fact that only a single dose of treatment was simulated whereas effective inhibition of inflammatory pathways would possibly require not only sustained presence of the antagonist but also reduction in the driving cause. In addition, the chosen treatment targeted IL1β, as this strategy has been shown to be effective at the group level and even more effectively in subgroups with enhanced systemic inflammation, which were not included in our cohort and may thus not be well represented in the resulting model. In different cohorts or settings, response to anti-inflammatory treatment may exceed intensive lipid lowering on patients with CVD as a comorbidity rather than as a primary indication. Nevertheless, for clinical applicability, the model should ideally capture such phenotypes. Inclusion of patients from these subgroups would improve efficacy, and if necessary, the model could be revised using indicators of enhanced systemic inflammation such as CRP. In any case, the demonstrated superior effect of combination therapy over intensive lipid lowering alone, suggests an ability of the modelling approach of the study to adequately simulate effects of drugs targeting different pathways in disease pathophysiology.

Prediction of Subject-Specific Drug Response

Drug response was then simulated in silico. In our study, the first category of simulated treatment was intensive lipid lowering, anti-inflammatory drugs (i.e., canakinumab), anti-diabetics (i.e., metformin), and a combination of intensive lipid lowering and anti-diabetic.

Two control simulations for each subject were also computed as a check on the mathematical formalism to prevent inadvertent design or coding defects. The first control simulation represented no change in treatment, where the expected result was to be the same as the baseline case but derived as if it was a treatment and running through the same simulation; if the output was found to differ from the baseline case, a logic or mathematical error would be detected. The second control simulation was named "multiple insult," which simulated a condition of a "perfect storm" of atherosclerosis risk factors causing know disease drivers. In this control, the expected result was to see degraded stability, roughly in proportion to the original stability, that is, the farther the subject started form these adverse conditions the worse their relative impact should be. If this did not result, a logic and/or mathematical error would be detected.

Multi-Level Analysis of Simulated Treatment Effect

Figure 20:
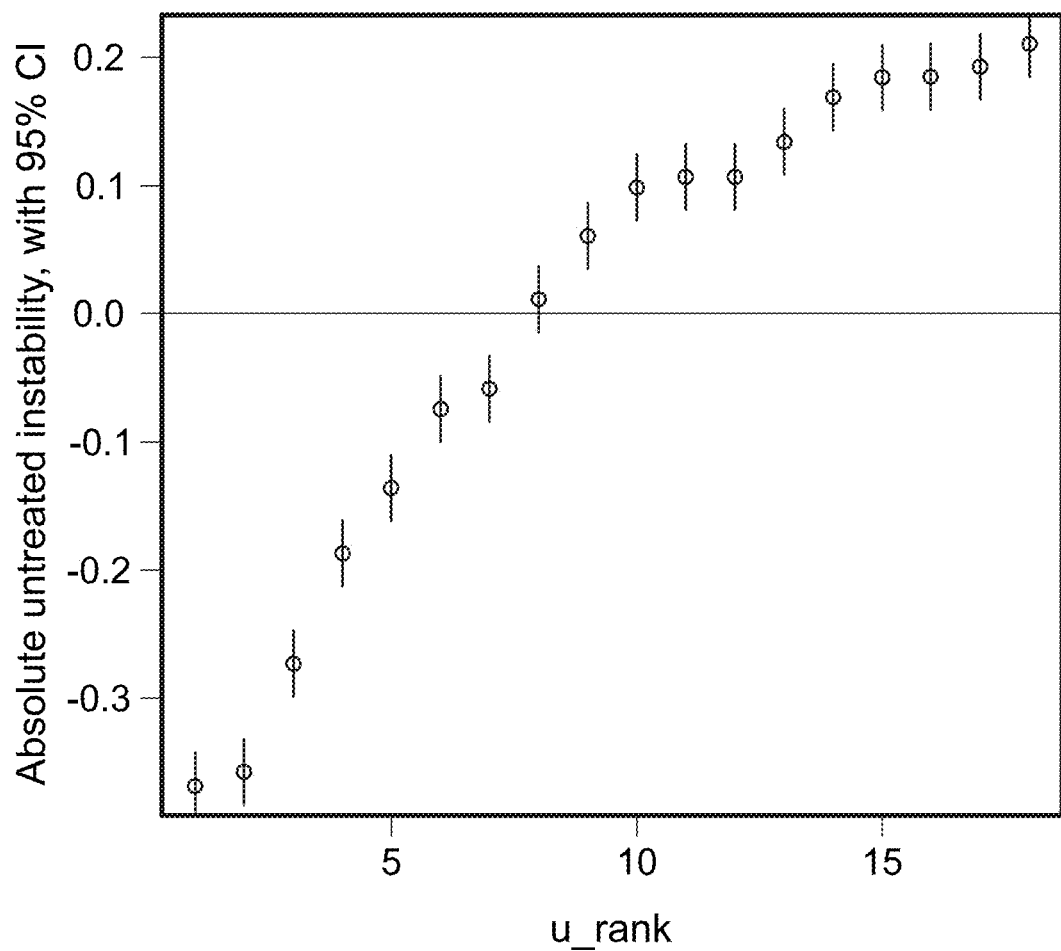
FIG. 20 is a "caterpillar" chart indicting how different subjects can vary in terms of their specific plaque instability.
Figure 21A:
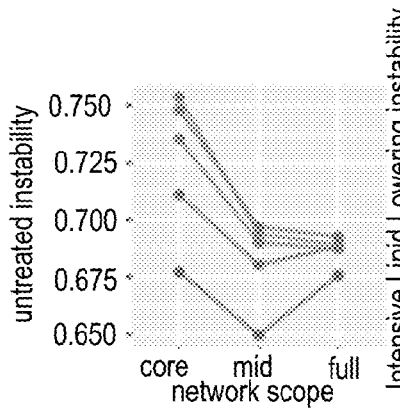
FIGS. 21A-21G are a series of plots showing mean absolute cohort-level instability from multi-level analysis across cell types and scopes.
Figure 21B:
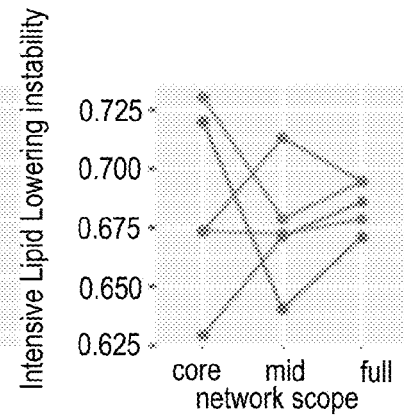
Figure 21C:
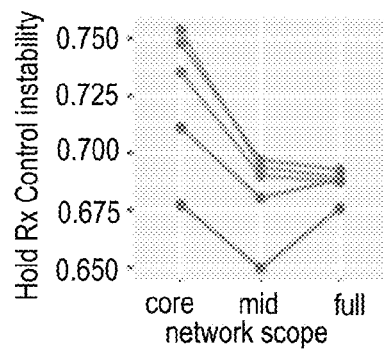
Figure 21D:
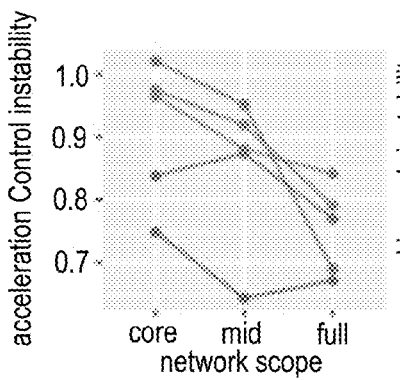
Figure 21E:
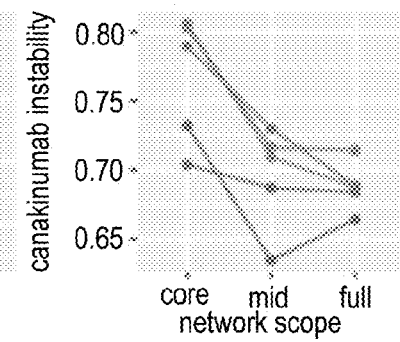
Figure 21F:
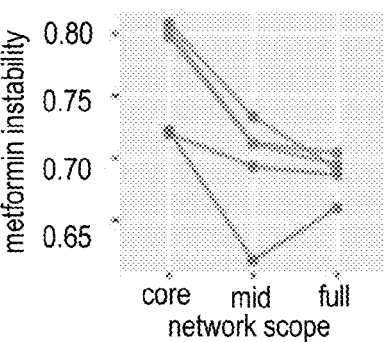
Figure 21G:
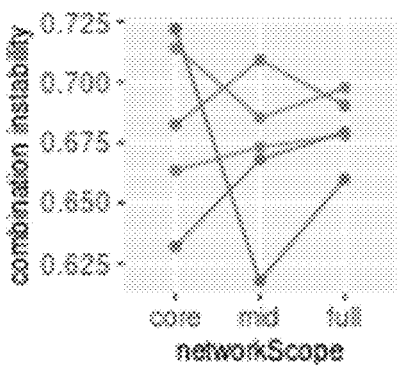
Figure 22A:
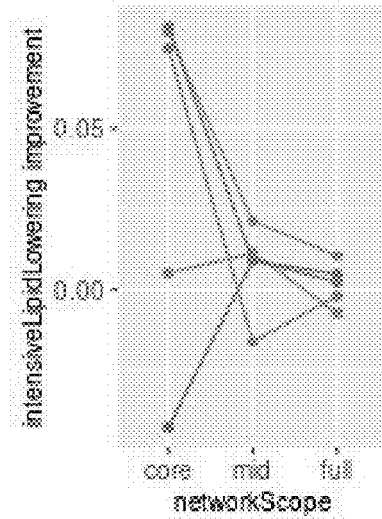
FIGS. 22A-22F are plots showing mean relative treatment effects (positive meaning that the instability decreased).
Figure 22B:
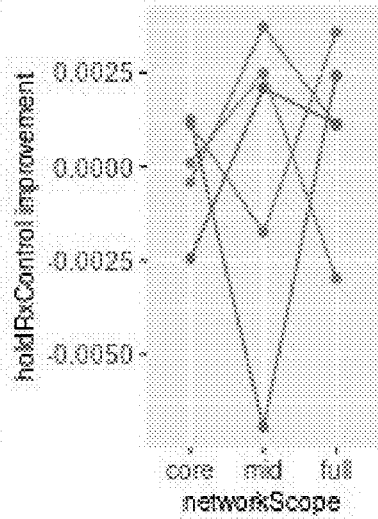
Figure 22C:
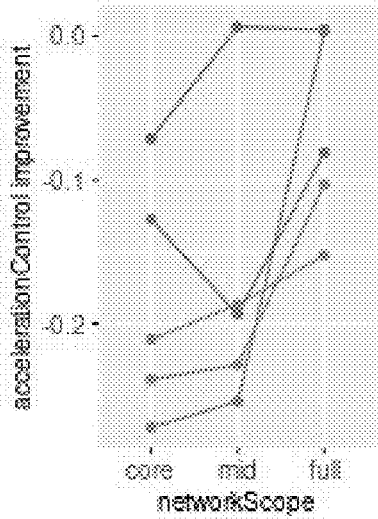
Figure 22D:
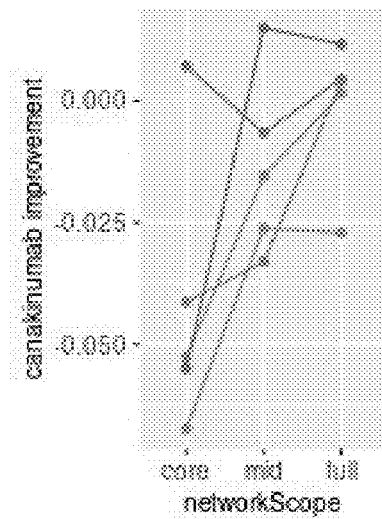
Figure 22E:
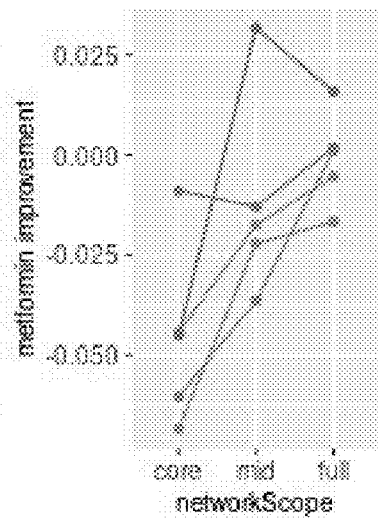
Figure 22F:
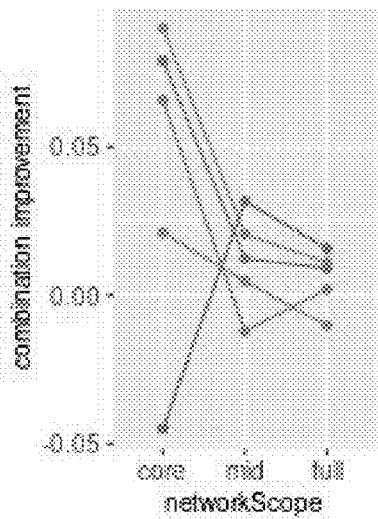

The simulated treated and baseline conditions were evaluated using multi-level analysis. Mean absolute cohort-level instability demonstrated coherent estimation across cell types and scopes. The variation across individuals is shown in FIG. 20, with mean effects setting intercepts and individual variations defined by patient-specific effects.

Further, the distribution of absolute baseline instability demonstrated a wide range across the experimental cohort (FIGS. 21A-21G). Specifically, in FIGS. 21A-21G each line indicates the particular therapy, with the response being shown as points for each network scope. Each panel represents either the baseline condition (FIG. 21A) or the simulated result (FIGS. 21B-21G) after the network is perturbed to reflect the effects. The use of multiple scopes is illustrated, as each represents a differing sensitivity or specificity to the simulated effect; too sensitive can produce false positive results mitigated by the higher scope networks, but the higher scope networks can miss the effect, given their more inclusive set of pathways. High numbers indicate "more" unstable, i.e., a lower instability is desirable from a subject's or patient's point of view. The plots are shown as an example, other network scopes or candidate treatments are to be understood without loss of generality.

Additionally, results demonstrated the mean relative treatment effects (positive indicate decreased instability our improved by treatment), across cohort, cell types, and network scopes (FIGS. 22A-22F). Specifically, FIGS. 22A-22F are plots showing a different way of representing the data that is also shown on the absolute charts, with a better visualization of the change, not just the net effect, of the treatments, respectively. The plots are shown as an example, network scopes or candidate treatments are to be understood without loss of generality.

In FIGS. 21 and 22, the panels represent results for each simulated therapy as well as computational controls. Each curve plots the absolute instability (FIG. 21) or the relative improvement (FIG. 22) at each cell type and scope. In general it may be seen that the core scope networks tend to show greater response to therapy than the full scope networks, which is expected based on the assignment of pathways where the more comprehensive the network the less sensitive to perturbation. Likewise, different cell type respond differently based on the nature of the therapeutic mechanism of action and its effect on the different types. The multi-level statistical analysis uses the differences in response by cell type and scope to determine the significance or certainty in the result and calculates the magnitude of effect based on the values of the various responses, which is done to build a robust calculation of response that is less sensitive to errors in individual molecular levels or missing biological knowledge in the several pathways and their assignments to cell types.

The multi-level analysis across cell types and scopes also demonstrated coherent estimation of mean absolute cohort-level response to treatment in the mathematical controls.

Treatment effects ranged from an improvement of 20% to no improvement. Not only did improvement vary from patient to patient, but the range of improvement observed differed based on how instability was estimated. Whereas improvement in clinically symptomatic patients ranged from −8% to +20% and from −22% to +13% for asymptomatic patients; these ranges tighten to −2% to +20% for patients with relatively unstable protein levels vs. −22% to +7% for patients with more stable protein levels. There are two important points raised by this; first, the ability to distinguish for a given patient rather than a group is motivated, and second, this is critically important as an improvement vs. standard clinical practice of using symptomatology to guide treatment.

Intensive lipid lowering had the strongest effect particularly in patients starting out with unstable plaque signatures and morphology. The simulated treatment predictions showed distinct variation between subjects. For example, patients P491 and P773 were initially characterized by highly unstable proteomic signatures, and where the best effect of treatment simulation would be expected. Indeed, whereas simulation with intensive lowering exceeded the other monotherapies, both anti-inflammatory and anti-lipid diabetic therapies conferred improvement, as well as simulation with the combination therapy that exceeded the benefit of intensive lipid lowering (Table 11, FIG. 23, and FIG. 24).

Table 11, below, shows the absolute and relative improvement for baseline and treated cases. Bold patient IDs were annotated using histology and clinical symptomatology as unstable. Key: Bas=baseline; ILL=Intensive Lipid Lowering; −IL1B=anti-IL1B (anti-inflammatory); Met=Metformin (anti-diabetic); Comb=Combination; Imp=improvement. p values: **<0.0001, *<0.001, **<0.01. Each patient is represented as a row, with quantitative assessment of absolute instability for the baseline conditions and each simulated condition followed by the quantitative relative improvement. The relative improvement cells are based on the significance of improvement, as judged by a net decrease of instability; +7% and above signifying statistically significant improvement relative to baseline, −5% to +6% signifying the absence of any statistically significant effect, and −7% and below signifying statistically significant degradation relative to baseline state. Rows are sorted by baseline instability. Patients P834, P821, P298, P187, and P491 (all categorized as unstable from histological reference) are seen to benefit the most from treatment, all starting from a position of very unstable and ending up at stable post treatment. Patients P853, P450, and P737 represent highly unstable plaques showing a lack of treatment effects, indicating that these cases could be viewed as the most to benefit from surgical intervention, given their highly unstable phenotypes and lack of improvement by pharmacotherapy. Patients P472, P265, and P682 represent patients for which neither pharmacotherapy will help nor can be needed, given the stability of the plaque.

TABLE 11

Simulated treatment effects for the Individual Subjects

| | Absolute Instability | | | | | Relative Improvement | | | | | | | |
| --- | --- | --- | --- | --- | --- | --- | --- | --- | --- | --- | --- | --- | --- |
| | | | | | | ILL | | −IL1B | | Met | | Comb | |
| Patient | Bas | ILL | −IL1B | Met | Comb | Imp | p | Imp | p | Imp | p | Imp | p |
| P450 | 96% | 85% | 96% | 96% | 84% | +11% | ** | −0% | 0.5 | +0% | 0.5 | +12% | ** |
| P491 | 95% | 75% | 88% | 87% | 74% | +19% | **** | +7% | *0.05 | +7% | *0.05 | +20% | **** |
| P853 | 94% | 76% | 89% | 88% | 75% | +18% | ** | +5% | 0.41 | +6% | 0.41 | +19% | ** |
| P834 | 94% | 81% | 93% | 92% | 80% | +13% | **** | +1% | 0.12 | +1% | 0.08 | +13% | **** |
| P737 | 92% | 79% | 91% | 91% | 78% | +13% | ** | +1% | 0.41 | +1% | 0.41 | +13% | ** |
| P773 | 89% | 70% | 82% | 82% | 69% | +18% | **** | +7% | *0.05 | +7% | *0.05 | +20% | **** |
| P187 | 86% | 72% | 85% | 84% | 71% | +14% | *** | +1% | 0.41 | +2% | 0.32 | +15% | *** |
| P549 | 86% | 76% | 88% | 87% | 75% | +10% | ** | −2% | 0.32 | −1% | 0.41 | +11% | ** |
| P821 | 85% | 73% | 86% | 85% | 72% | +12% | ** | −1% | 0.41 | +0% | 0.5 | +13% | ** |
| P298 | 81% | 69% | 78% | 78% | 68% | +13% | ** | +3% | 0.24 | +3% | 0.24 | +13% | ** |
| P762 | 76% | 66% | 80% | 79% | 64% | +11% | ** | −3% | 0.24 | −2% | 0.32 | +12% | ** |
| P836 | 69% | 65% | 79% | 78% | 64% | +5% | 0.12 | −9% | *0.02 | −8% | *0.03 | +6% | 0.08 |
| P504 | 68% | 62% | 78% | 77% | 61% | +6% | 0.08 | −10% | ** | −9% | *0.02 | +7% | *0.05 |
| P946 | 62% | 61% | 75% | 74% | 60% | +1% | 0.41 | −13% | ** | −12% | ** | +2% | 0.32 |
| P864 | 57% | 61% | 75% | 73% | 60% | −4% | 0.17 | −18% | **** | −16% | **** | −3% | 0.24 |
| P472 | 48% | 51% | 67% | 65% | 48% | −2% | 0.32 | −18% | **** | −17% | **** | +0% | 0.5 |
| P682 | 40% | 48% | 62% | 61% | 47% | −8% | *0.03 | −21% | **** | −21% | **** | −7% | *0.05 |
| P265 | 39% | 46% | 61% | 61% | 44% | −7% | *0.05 | −22% | **** | −21% | **** | −5% | 0.12 |

Figure 23:
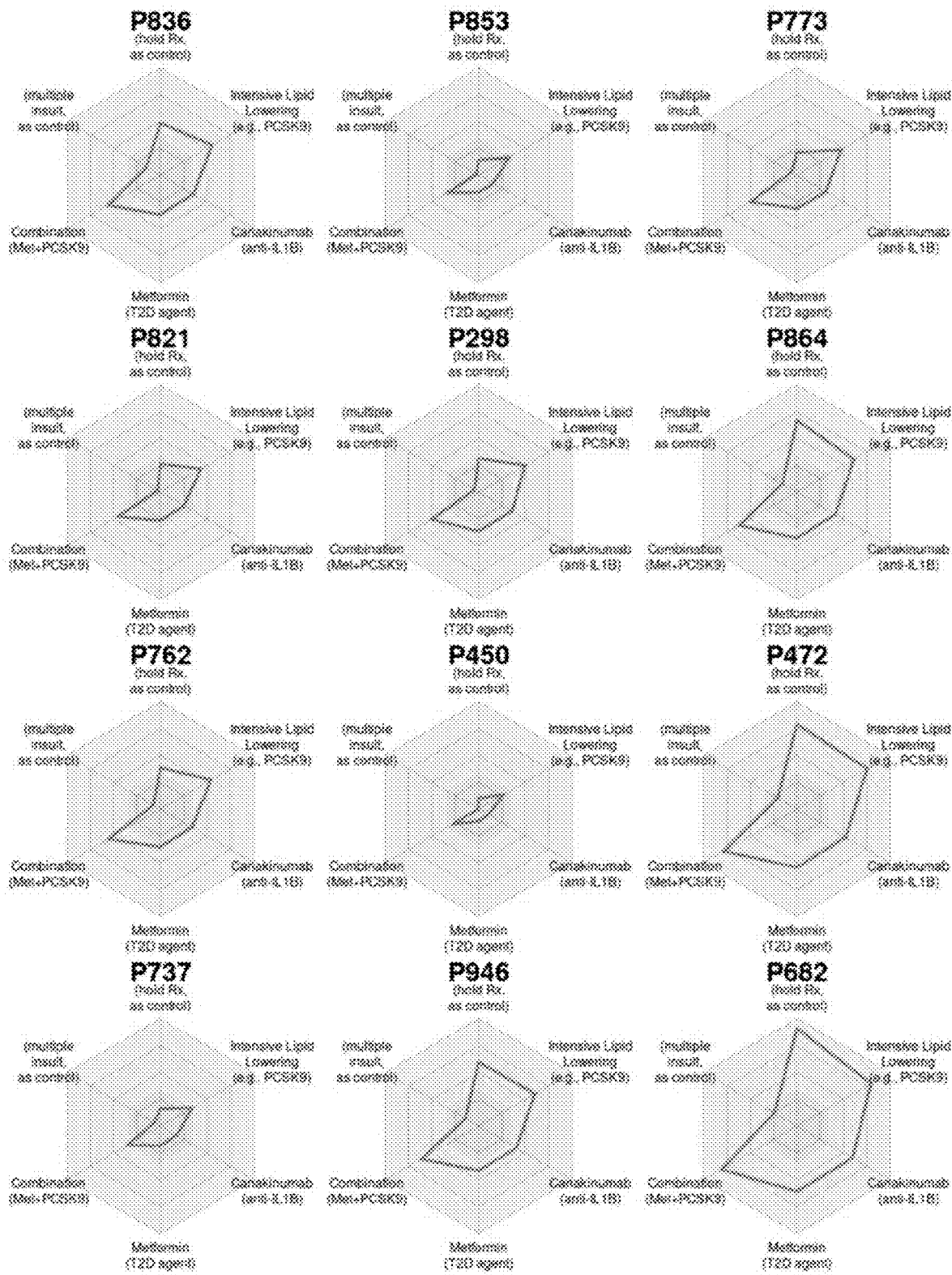
FIG. 23 are radar charts representing degrees of absolute atherosclerotic plaque stability for an example of a set of patients. Outer lines are better for the patient, with green signifying minimal disease, yellow stable plaque, and red unstable plaque.
Figure 23:
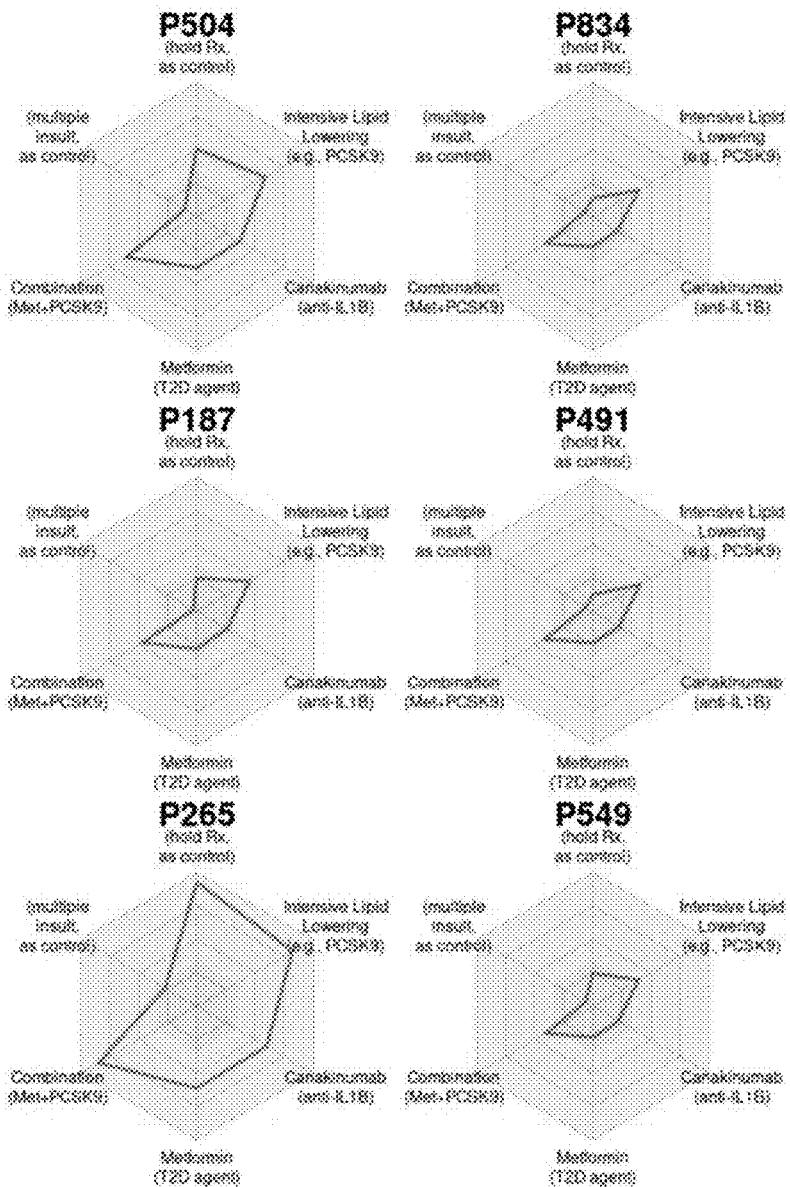

Radar charts, shown in FIG. 23, represent the degree of absolute atherosclerotic plaque stability. Four potential treatments and mathematical two controls were simulated for each patient. The outer section (or green) indicates protein level signatures with minimal disease, light gray (or yellow) indicates stable plaque, and dark gray (or red) indicates unstable plaque. The treatments included intensive lipid lowering, anti-inflammatory and anti-diabetics and a combination of intensive lipid lowering and anti-diabetics. The two controls were done to exclude mathematical errors in the model as well as to simulate the anticipated effect of multiple insults representing maximum disease progression. Each of these conditions was plotted as the absolute effect on stability.

Figure 24:
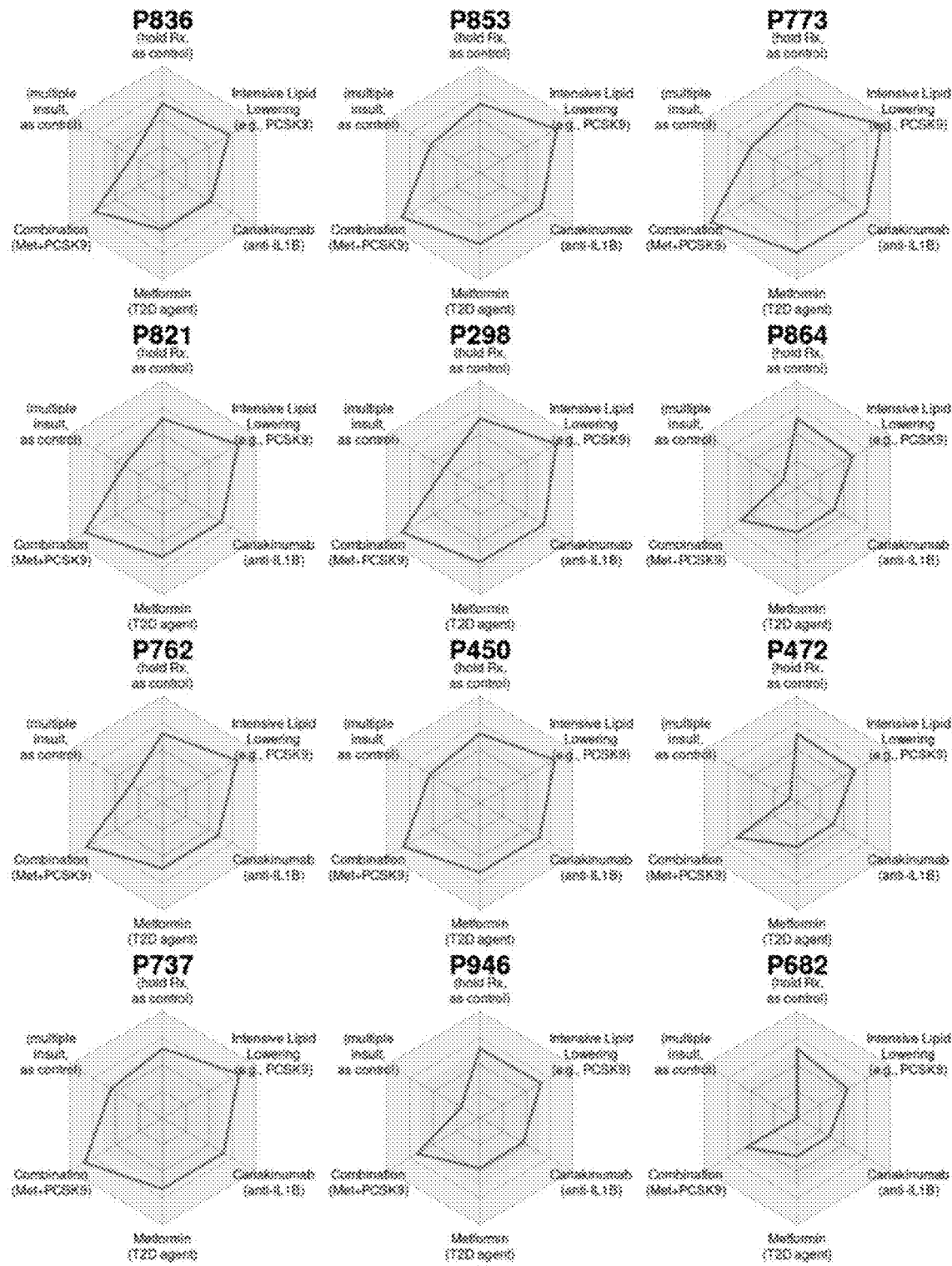
FIG. 24 are radar charts representing relative improvement after treatment simulation for an example of a set of patients. These are a different way of representing the data that is also shown on the absolute charts, with a better visualization of the change, not just the net effect, of the treatments respectively. Here, outer lines represent more pronounced effect, with green signifying improvement and red signifying worsening disease.
Figure 24:
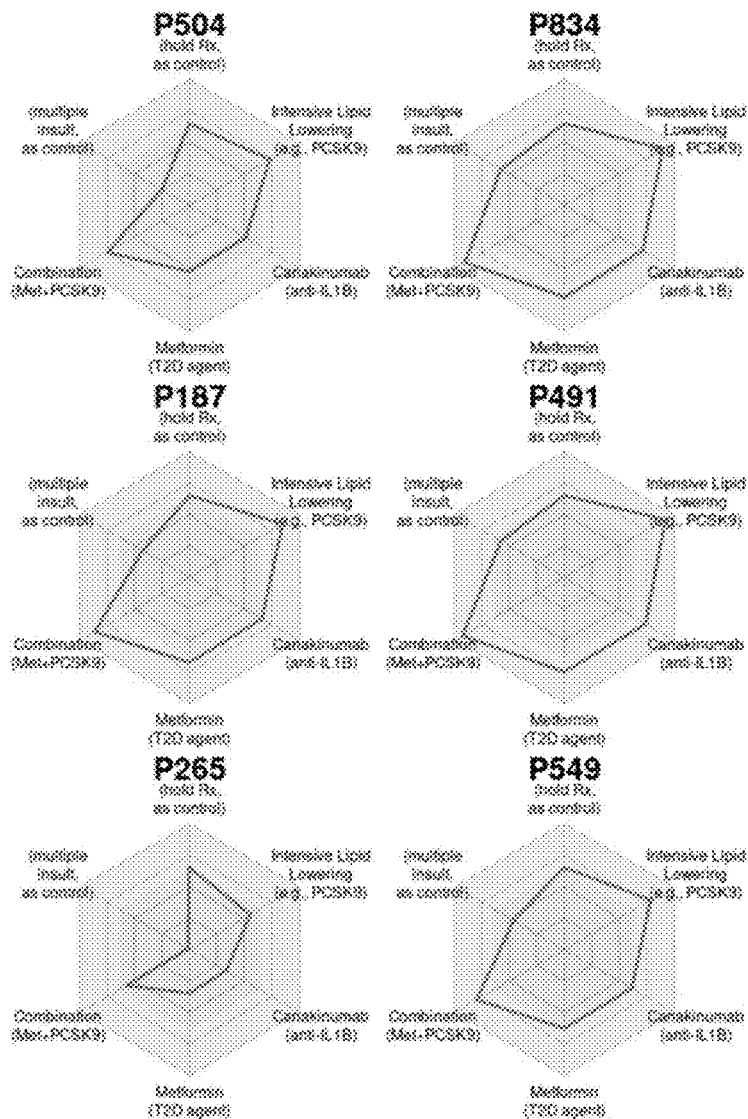

Radar charts, shown in FIG. 24, represent the relative improvement after treatment simulation. For each patient, four potential treatments and two mathematical controls were simulated. The light gray outer region (or green) indicates protein level signatures conferring increased stability, and inner, dark gray region (or red) indicates decreased stability. The treatments included intensive lipid lowering, anti-inflammatory and anti-diabetics and a combination of intensive lipid lowering and anti-diabetics. The two controls were done to exclude mathematical errors in the model as well as to simulate the anticipated effect of multiple insults representing maximum disease progression. Each of these conditions was plotted as the relative improvement as compared to the untreated or baseline condition.

We next observed a relatively well-defined threshold of absolute instability level of approximately 76%, where subjects with greater instability in the baseline state showed benefit from intensive lipid lowering and improved further with combination therapy but did not benefit when anti-inflammatory or anti-diabetic agents alone were simulated.

One set of patients that were initially characterized as highly unstable, did not show any response to the simulated pharmacotherapies. Importantly, this finding suggested an ability of the modelling approach of the study to identify individuals with a high risk, rather suitable for surgical treatment than pharmacotherapy. Further, we found that patients with initially more stable plaque signatures either did not improve, regardless of treatment category simulated. In this proof-of-concept setting, combinatory treatment or intensive lipid lowering alone had a generally beneficial effect on stability, with combination therapy providing incremental benefit for many patients.

Full results including summary of mean effects, confidence intervals, and assessment of contribution variance are provided in Table 12 and Table 13, shown below.

TABLE 12

Absolute Instability, Treated and Baseline, with Confidence Intervals

| Patient | Baseline | Intensive Lipid Lowering | Canakinumab | Metformin | Combination |
|---|---|---|---|---|---|
| P450 | 0.96 [0.94, 0.99] | 0.85 [0.82, 0.88] | 0.96 [0.93, 0.99] | 0.96 [0.93, 0.99] | 0.84 [0.81, 0.87] |
| P491 | 0.95 [0.92, 0.97] | 0.75 [0.72, 0.78] | 0.88 [0.85, 0.91] | 0.87 [0.84, 0.9] | 0.74 [0.71, 0.77] |
| P853 | 0.94 [0.91, 0.96] | 0.81 [0.78, 0.84] | 0.93 [0.9, 0.96] | 0.92 [0.89, 0.95] | 0.8 [0.77, 0.83] |
| P834 | 0.94 [0.91, 0.96] | 0.76 [0.73, 0.79] | 0.89 [0.86, 0.92] | 0.88 [0.85, 0.91] | 0.75 [0.72, 0.78] |
| P737 | 0.92 [0.9, 0.95] | 0.79 [0.76, 0.82] | 0.91 [0.88, 0.94] | 0.91 [0.88, 0.94] | 0.78 [0.76, 0.81] |
| P773 | 0.89 [0.86, 0.91] | 0.7 [0.67, 0.73] | 0.82 [0.79, 0.85] | 0.82 [0.78, 0.85] | 0.69 [0.66, 0.72] |
| P187 | 0.86 [0.84, 0.89] | 0.72 [0.69, 0.74] | 0.85 [0.82, 0.88] | 0.84 [0.81, 0.87] | 0.71 [0.68, 0.74] |
| P549 | 0.86 [0.83, 0.89] | 0.76 [0.73, 0.79] | 0.88 [0.85, 0.91] | 0.87 [0.84, 0.9] | 0.75 [0.72, 0.78] |
| P821 | 0.85 [0.83, 0.88] | 0.73 [0.7, 0.76] | 0.86 [0.83, 0.89] | 0.85 [0.82, 0.88] | 0.72 [0.69, 0.75] |
| P298 | 0.81 [0.79, 0.84] | 0.69 [0.66, 0.72] | 0.78 [0.75, 0.81] | 0.78 [0.75, 0.81] | 0.68 [0.65, 0.71] |
| P762 | 0.76 [0.74, 0.79] | 0.66 [0.63, 0.68] | 0.8 [0.77, 0.83] | 0.79 [0.76, 0.82] | 0.64 [0.61, 0.67] |
| P836 | 0.69 [0.67, 0.72] | 0.65 [0.62, 0.67] | 0.79 [0.76, 0.82] | 0.78 [0.75, 0.81] | 0.64 [0.61, 0.67] |
| P504 | 0.68 [0.65, 0.7] | 0.62 [0.59, 0.65] | 0.78 [0.75, 0.81] | 0.77 [0.74, 0.8] | 0.61 [0.58, 0.64] |
| P946 | 0.62 [0.59, 0.64] | 0.61 [0.58, 0.64] | 0.75 [0.72, 0.78] | 0.74 [0.71, 0.77] | 0.6 [0.57, 0.63] |
| P864 | 0.57 [0.54, 0.59] | 0.61 [0.58, 0.64] | 0.75 [0.71, 0.78] | 0.73 [0.7, 0.76] | 0.6 [0.57, 0.63] |
| P472 | 0.48 [0.46, 0.51] | 0.51 [0.48, 0.54] | 0.67 [0.64, 0.7] | 0.65 [0.62, 0.68] | 0.48 [0.46, 0.51] |
| P682 | 0.4 [0.37, 0.42] | 0.48 [0.45, 0.51] | 0.62 [0.59, 0.65] | 0.61 [0.58, 0.64] | 0.47 [0.44, 0.5] |
| P265 | 0.39 [0.36, 0.41] | 0.46 [0.43, 0.49] | 0.61 [0.58, 0.64] | 0.61 [0.57, 0.64] | 0.44 [0.41, 0.47] |

TABLE 13

Relative Improvement, with Confidence Intervals

| | Relative Improvement | | | | | | | |
|---|---|---|---|---|---|---|---|---|
| | Intensive Lipid Lowering | | Canakinumab | | Metformin | | Combination | |
| Patient | Improvement | p | Improvement | p | Improvement | p | Improvement | p |
| P450 | +0.11 [0.09, 0.14] | **<0.01 | 0 [−0.03, 0.02] | 0.5 | 0 [−0.02, 0.03] | 0.5 | +0.12 [0.1, 0.15] | **<0.01 |
| P491 | +0.19 [0.17, 0.22] | ****<0.0001 | +0.07 [0.04, 0.09] | *0.05 | +0.07 [0.05, 0.1] | *0.05 | +0.2 [0.17, 0.23] | ****<0.0001 |
| P853 | +0.13 [0.1, 0.15] | **<0.01 | +0.01 [−0.02, 0.03] | 0.41 | +0.01 [−0.01, 0.04] | 0.41 | +0.13 [0.11, 0.16] | **<0.01 |
| P834 | +0.18 [0.15, 0.2] | ****<0.0001 | +0.05 [0.02, 0.07] | 0.12 | +0.06 [0.03, 0.08] | 0.08 | +0.19 [0.16, 0.21] | ****<0.0001 |
| P737 | +0.13 [0.1, 0.15] | **<0.01 | +0.01 [−0.02, 0.03] | 0.41 | +0.01 [−0.01, 0.04] | 0.41 | +0.13 [0.11, 0.16] | **<0.01 |
| P773 | +0.18 [0.16, 0.21] | ****<0.0001 | +0.07 [0.04, 0.09] | *0.05 | +0.07 [0.04, 0.1] | *0.05 | +0.2 [0.17, 0.22] | ****<0.0001 |
| P187 | +0.14 [0.12, 0.17] | ***<0.001 | +0.01 [−0.02, 0.03] | 0.41 | +0.02 [−0.01, 0.05] | 0.32 | +0.15 [0.13, 0.18] | ***<0.001 |
| P549 | +0.1 [0.07, 0.13] | **<0.01 | −0.02 [−0.05, 0] | 0.32 | −0.01 [−0.04, 0.01] | 0.41 | +0.11 [0.08, 0.14] | **<0.01 |
| P821 | +0.12 [0.09, 0.15] | **<0.01 | −0.01 [−0.03, 0.02] | 0.41 | 0 [−0.03, 0.03] | 0.5 | +0.13 [0.11, 0.16] | **<0.01 |
| P298 | +0.13 [0.1, 0.15] | **<0.01 | +0.03 [0, 0.06] | 0.24 | +0.03 [0.01, 0.06] | 0.24 | +0.13 [0.11, 0.16] | **<0.01 |

TABLE 13-continued

Relative Improvement, with Confidence Intervals

| Pa-tient | Intensive Lipid Lowering | | Canakinumab | | Metformin | | Combination | |
|---|---|---|---|---|---|---|---|---|
| | Improvement | p | Improvement | p | Improvement | p | Improvement | p |
| P762 | +0.11 [0.08, 0.13] | **<0.01 | −0.03 [−0.06, −0.01] | 0.24 | −0.02 [−0.05, 0] | 0.32 | +0.12 [0.09, 0.15] | **<0.01 |
| P836 | +0.05 [0.02, 0.08] | 0.12 | −0.09 [−0.12, −0.06] | *0.02 | −0.08 [−0.11, −0.05] | *0.03 | +0.06 [0.03, 0.08] | 0.08 |
| P504 | +0.06 [0.03, 0.09] | 0.08 | −0.1 [−0.12, −0.07] | **<0.01 | −0.09 [−0.11, −0.06] | *0.02 | +0.07 [0.04, 0.1] | *0.05 |
| P946 | +0.01 [−0.02, 0.03] | 0.41 | −0.13 [−0.16, −0.1] | **<0.01 | −0.12 [−0.15, −0.1] | **<0.01 | +0.02 [−0.01, 0.04] | 0.32 |
| P864 | −0.04 [−0.06, −0.01] | 0.17 | −0.18 [−0.2, −0.15] | ****<0.0001 | −0.16 [−0.19, −0.14] | ****<0.0001 | −0.03 [−0.06, 0] | 0.24 |
| P472 | −0.02 [−0.05, 0] | 0.32 | −0.18 [−0.21, −0.16] | ****<0.0001 | −0.17 [−0.19, −0.14] | ****<0.0001 | 0 [−0.03, 0.03] | 0.5 |
| P682 | −0.08 [−0.1, −0.05] | *0.03 | −0.21 [−0.24, −0.19] | ****<0.0001 | −0.21 [−0.23, −0.18] | ****<0.0001 | −0.07 [−0.09, −0.04] | *0.05 |
| P265 | −0.07 [−0.09, −0.04] | *0.05 | −0.22 [−0.25, −0.2] | ****<0.0001 | −0.21 [−0.24, −0.19] | ****<0.0001 | −0.05 [−0.08, −0.03] | 0.12 |

Personalized treatment recommendations were then composed based on the in-silico results for each patient using an automated decision algorithm where simulations of different pharmacotherapies were incorporated. The recommendations combined the level of instability achieved on the selected drug choices and the controls, with a text statement automatically generated to reflect the best therapy for that patient (FIGS. 25A-25C). Specifically, FIGS. 25A-25C show personalized patient treatment recommendations for the three example patients, as might be printed by a clinical decision support system incorporating the technique from this study. A printed or digital recommendation such as this could be used in a patient-doctor consultation. Recommendations generated by the software include one or more of the individual's absolute and relative radar plots, a statement on the benefit available through pharmacotherapy, and one or two heatmaps representing treated and untreated or baseline protein signatures.

Patient "John Doe" is an example of a patient with a highly unstable initial condition that can be improved with high confidence by pharmacotherapy (FIG. 25A). The simulated treatments for patient P491 demonstrated statistically significant benefit on combination therapy. The top five baseline protein levels matched four out of five unstable exemplars and one stable, thus providing strong support for an unstable state. After recommended treatment, two minimal disease, two stable, and only one unstable exemplar were matched, reflecting improvement by treatment.

Patient "Bill Smith" represents a patient starting from a more stable initial condition where pharmacotherapy would not be recommended (FIG. 25B). Patient P265's baseline protein levels showed matches with four minimal disease and one stable exemplar, indicating stability, with no improvement after simulated treatments. The recommended therapy would be to maintain the current therapy rather than any of the simulated therapies.

Patient "David Jones" represents a patient that would receive only marginal improvement from pharmacotherapy, but based on the highly unstable starting point, one would choose a procedural intervention as the best course (FIG. 25C). The simulated treatments for patient P450 demonstrated statistically significant benefit on combination therapy.

Heatmaps were also included for specific protein level signatures, including the protein expression for the baseline condition, and adding the treated condition in cases where statistically significant treatment improvement was found. The degree to which this would be clinically significant is determined from the difference in clinical presentation; treatments demonstrate a strength commensurate with the difference between being asymptomatic vs. symptomatic. The results for P491 and P265 illustrate the range over which the simulation capability can be applied (FIGS. 25A-25C).

OTHER EMBODIMENTS

It is to be understood that while the invention has been described in conjunction with the detailed description thereof, the foregoing description is intended to illustrate and not limit the scope of the invention, which is defined by the scope of the appended claims. The following are numbered embodiments intended to further illustrate, but not limit, the scope of the invention.

Other aspects, advantages, and modifications are within the scope of the following claims.

What is claimed is:

1. A method of providing a recommendation of an anti-diabetic therapy for a patient with known or suspected atherosclerotic cardiovascular disease, the method comprising:
   receiving a first input of non-invasively obtained imaging data related to a plaque from a set of test subjects;
   receiving a second input of molecular expression data from the set of test subjects;
   creating a training set comprising the first input and the second input;
   training a neural network using the training set, the neural network configured to predict molecule levels based on the non-invasively obtained imaging data from the set of test subjects;
   receiving non-invasively obtained imaging data related to a plaque from the patient;
   generating virtual 'omics data that include predicted molecule levels of the patient, by applying the neural network to the non-invasively obtained imaging data from the patient;
   providing the virtual 'omics data to a systems biology model of atherosclerotic cardiovascular disease to generate a patient-specific systems biology model, wherein
   (i) the systems biology model represents a plurality of pathways associated with atherosclerotic cardiovascular disease,
   (ii) each pathway in the plurality of pathways corresponds to one or more of MTOR, NFκβ1, ICAM1, or VCAM1,
   (iii) the systems biology model includes a disease-associated molecule level for each molecule in the systems biology model, and (iv) the patient-specific systems biology model includes predicted molecule levels that are updated from the disease-associated molecule level;

updating the patient-specific systems biology model with information relating to an effect on glucose levels by an anti-diabetic agent based on a known mechanism of action of the anti-diabetic agent; and simulating a therapeutic response by the patient to the anti-diabetic agent in the updated patient-specific systems biology model to obtain a simulated therapeutic effect, wherein the simulated therapeutic effect is based on change in the predicted molecule levels in the updated patient-specific systems biology model with and without the anti-diabetic agent.

2. The method of claim 1, wherein the molecule is a gene, a protein, or a metabolite.

3. The method of claim 1, wherein simulating the therapeutic response comprises setting decreased levels of molecules related to plaque instability and setting increased levels of molecules related to plaque stability in the patient-specific systems biology model.

4. The method of claim 1, wherein the predicted molecule levels comprise disease gene transcript levels, disease protein levels, or a combination of both derived from the non-invasively obtained data.

5. The method of claim 1, wherein the imaging data is radiological imaging data obtained by computed tomography (CT), dual energy computed tomography (DECT), spectral computed tomography (spectral CT), computed tomography angiography (CTA), cardiac computed tomography angiography (CCTA), magnetic resonance imaging (MRI), multi-contrast magnetic resonance imaging (multi-contrast MRI), ultrasound (US), positron emission tomography (PET), intra-vascular ultrasound (IVUS), optical coherence tomography (OCT), near-infrared radiation spectroscopy (NIRS), or single-photon emission tomography (SPECT) diagnostic images, or any combination thereof.

6. The method of claim 1, further comprising processing the non-invasively obtained imaging data to obtain quantitative plaque morphology data including structural anatomy data, tissue composition data, or both.

7. The method of claim 6, wherein the structural anatomy data comprises data relating to a level of any one or more of remodeling, wall thickening, ulceration, stenosis, dilation, or plaque burden.

8. The method of claim 6, wherein the tissue composition data comprises data relating to a level of any one or more of calcification, lipid-rich necrotic core (LRNC), intraplaque hemorrhage (IPH), matrix, fibrous cap, or perivascular adipose tissue (PVAT).

9. The method of claim 1, wherein the pathways are compartmentalized into cell-specific networks.

10. The method of claim 9, wherein the cell-specific networks include at least an endothelial cell network, a macrophage network, and a vascular smooth muscle cell network.

11. The method of claim 1, wherein the anti-diabetic agent is metformin.

12. The method of claim 1, further comprising recommending a combination of the anti-diabetic agent and one or both of a lipid-lowering drug and an anti-inflammatory drug.

13. The method of claim 1, wherein simulating the therapeutic response for the anti-diabetic agent in the patient-specific systems biology model comprises:

determining a set of molecules known to be affected by the anti-diabetic agent;

defining a therapeutic effect molecule level for each molecule in the set of molecules based on one or more known mechanisms of action of the anti-diabetic agent on the set of molecules; and estimating a therapeutic effect molecule level for molecules represented in the patient-specific systems biology model other than in the set of molecules, based on a simulated effect of the defined therapeutic effect molecule levels of the set of molecules on one or more of the other molecules represented in the network.

14. The method of claim 1, wherein the systems biology model includes one or more pathways represented in Table 5 or Table 6 that are affected by glucose levels.

15. A method of identifying one or more contraindications associated with an anti-diabetic therapy for a patient diagnosed with atherosclerotic cardiovascular disease, the method comprising:

receiving a first input of non-invasively obtained imaging data related to a plaque from a set of test subjects;

receiving a second input of molecular expression data from the set of test subjects;

creating a training set comprising the first input and the second input;

training a neural network using the training set, the neural network configured to predict molecule levels based on the non-invasively obtained imaging data from the set of test subjects;

receiving non-invasively obtained imaging data related to a plaque from the patient;

generating virtual 'omics data that include predicted molecule levels of the patient, by applying the neural network to the non-invasively obtained imaging data from the patient;

providing the virtual 'omics data to a systems biology model of atherosclerotic cardiovascular disease to generate a patient-specific systems biology model, wherein (i) the systems biology model represents a plurality of pathways associated with atherosclerotic cardiovascular disease, (ii) each pathway in the plurality of pathways corresponds to one or more of MTOR, NFκβ1, ICAM1, or VCAM1, (iii) the systems biology model includes a disease-associated molecule level for each molecule in the systems biology model, and (iv) the patient-specific systems biology model includes predicted molecule levels that are updated from the disease-associated molecule level;

updating the patient-specific systems biology model with information relating to an effect on glucose levels by an anti-diabetic agent based on a known mechanism of action of the anti-diabetic agent;

simulating a therapeutic response by the patient to the anti-diabetic agent in the updated patient-specific systems biology model to obtain a simulated therapeutic effect, wherein the simulated therapeutic effect is based on change in the predicted molecule levels in the updated patient-specific systems biology model with and without the anti-diabetic agent; and identifying one or more contraindications associated with the anti-diabetic agent based on change in the predicted molecule levels in the patient-specific systems biology model with and without the anti-diabetic agent.

16. The method of claim 15, wherein the molecule is a gene, a protein, or a metabolite.

17. The method of claim 15, wherein the anti-diabetic agent is metformin.

18. The method of claim 15, wherein the systems biology model includes one or more pathways represented in Table 5 or Table 6 that are affected by glucose levels.

19. A method of screening a candidate anti-diabetic agent for atherosclerotic cardiovascular disease, the method comprising:
receiving a first input of non-invasively obtained imaging data related to a plaque from a first set of test subjects;
receiving a second input of molecular expression data from the first set of test subjects;
creating a training set comprising the first input and the second input;
training a neural network using the training set, the neural network configured to predict molecule levels based on the non-invasively obtained imaging data from the first set of test subjects;
receiving non-invasively obtained imaging data related to a plaque from each of a second set of test subjects who have been diagnosed with atherosclerotic cardiovascular disease;
for each test subject of the second set of test subjects:
generating virtual 'omics data that include predicted molecule levels of a respective test subject, by applying the neural network to the non-invasively obtained imaging data from the respective test subject;
providing the virtual 'omics data to a systems biology model of atherosclerotic cardiovascular disease to generate a test subject-specific systems biology model for the respective test subject, wherein
(i) the systems biology model represents a plurality of pathways associated with atherosclerotic cardiovascular disease,
(ii) the plurality of pathways include one or more pathways corresponding to potential targets of the candidate anti-diabetic agent,
(iii) the systems biology model includes a disease-associated molecule level for each molecule in the systems biology model, and
(iv) the test subject-specific systems biology model includes predicted molecule levels that are updated from the disease-associated molecule level;
updating the test subject-specific systems biology model with information relating to an effect on glucose levels by a candidate anti-diabetic agent based on a known mechanism of action of the candidate anti-diabetic agent; and
simulating a therapeutic response by the respective test subject to the anti-diabetic agent in the updated test subject-specific systems biology model to obtain a simulated therapeutic effect, wherein the simulated therapeutic effect is based on change in the predicted molecule levels in the updated test subject-specific systems biology model with and without the candidate anti-diabetic agent.

20. The method of claim 19, wherein the molecule is a gene, a protein, or a metabolite.

21. The method of claim 19, wherein the anti-diabetic agent is metformin.

22. The method of claim 19, wherein the systems biology model includes one or more pathways represented in Table 5 or Table 6 that are affected by glucose levels.

23. A method of screening a potential subject for enrollment in a clinical trial testing safety or efficacy, or both, of a candidate anti-diabetic agent for atherosclerotic cardiovascular disease, the method comprising:
receiving a first input of non-invasively obtained imaging data related to a plaque from a set of test subjects;
receiving a second input of molecular expression data from the set of test subjects;
creating a training set comprising the first input and the second input;
training a neural network using the training set, the neural network configured to predict molecule levels based on the non-invasively obtained imaging data from the set of test subjects;
receiving non-invasively obtained imaging data related to a plaque from the potential subject;
generating virtual 'omics data that include predicted molecule levels of the potential subject, by applying the neural network to the non-invasively obtained imaging data from the potential subject;
providing the virtual 'omics data to a systems biology model of atherosclerotic cardiovascular disease to generate a subject-specific systems biology model, wherein
(i) the systems biology model represents a plurality of pathways associated with atherosclerotic cardiovascular disease,
(ii) each pathway in the plurality of pathways corresponds to one or more of MTOR, NFκβ1, ICAM1, or VCAM1,
(iii) the systems biology model includes a disease-associated molecule level for each molecule in the systems biology model, and
(iv) the subject-specific systems biology model includes predicted molecule levels that are updated from the disease-associated molecule level;
updating the subject-specific systems biology model with predicted molecular levels derived from information relating to an effect on glucose by a candidate anti-diabetic agent based on a known mechanism of action of the candidate anti-diabetic agent; and
simulating a therapeutic response by the potential subject to the candidate anti-diabetic agent in the updated subject-specific systems biology model to obtain a simulated therapeutic effect, wherein the simulated therapeutic effect is based on change in the predicted molecule levels in the updated subject-specific systems biology model with and without the candidate anti-diabetic agent.

24. The method of claim 1, further comprising:
providing a report, in response to determining that the simulated therapeutic effect indicates an improvement for the patient, recommending the anti-diabetic agent for the patient.

* * * * *

UNITED STATES PATENT AND TRADEMARK OFFICE
CERTIFICATE OF CORRECTION

PATENT NO. : 11,887,713 B2
APPLICATION NO. : 17/838147
DATED : January 30, 2024
INVENTOR(S) : Andrew J. Buckler et al.

Page 1 of 4

It is certified that error appears in the above-identified patent and that said Letters Patent is hereby corrected as shown below:

On the Title Page

Page 2, Column 2 (Other Publications), Line 4, delete ""Antiinflammatory" and insert -- "Anti-inflammatory --.

Page 2, Column 2 (Other Publications), Line 27, delete "BioImage" and insert -- BioImage --.

Page 5, Column 2 (Other Publications), Line 7, delete "Appin." and insert -- Appln. --.

Page 5, Column 2 (Other Publications), Line 9, delete "Pathway" and insert -- Pathways --.

In the Specification

Column 1, Line 25, delete "worldwide worldwide" and insert -- worldwide --.

Column 5, Line 6, delete "single-photon emission tomography (SPECT)", and insert -- single-photon emission computed tomography (SPECT) --.

Column 13, Line 3, delete "lipid lowering" and insert -- lipid-lowering --.

Column 13, Line 6, delete "indicting" and insert -- indicating --.

Column 15, Line 65, delete "CTDIvol16cm" and insert -- CTDIvol 16 cm --.

Column 15, Line 66, delete "CTDIvol32cm" and insert -- CTDIvol 32 cm --.

Column 22, Line 50, delete "(2018))." and insert -- (2018). --.

Column 23, Line 50, delete "(2018))." and insert -- (2018). --.

Signed and Sealed this
Fourth Day of June, 2024

Katherine Kelly Vidal
*Director of the United States Patent and Trademark Office*

CERTIFICATE OF CORRECTION (continued)
U.S. Pat. No. 11,887,713 B2

Column 28, Line 23, delete "(MM)," and insert -- (MRI), --.

Column 30, Line 59, delete "(MM)," and insert -- (MRI), --.

Column 31, Line 32, delete "lipid lowering" and insert -- lipid-lowering --.

Column 33, Line 57, delete "computer-or" and insert -- computer- or --.

Column 34, Line 22, below "other." delete "The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.".

Column 37, Line 38, delete "adrenomedul-lin," and insert -- adrenomedullin, --.

Column 37, Line 66, delete "inucleic" and insert -- nucleic --.

Column 38, Line 10, delete "lipid lowering" and insert -- lipid-lowering --.

Column 38, Line 18, delete "lipid lowering" and insert -- lipid-lowering --.

Column 38, Line 21, delete "lipid lowering" and insert -- lipid-lowering --.

Column 38, Line 43, delete "lipid lowering" and insert -- lipid-lowering --.

Column 38, Line 47, delete "lipid lowering" and insert -- lipid-lowering --.

Column 40, Line 23, delete "lipid lowering" and insert -- lipid-lowering --.

Column 40, Line 25, delete "lipid lowering" and insert -- lipid-lowering --.

Column 40, Line 27, delete "lipid lowering" and insert -- lipid-lowering --.

Column 43, Line 59, delete "kosapent" and insert -- Icosapent --.

Column 43, Line 62, delete "kosapent" and insert -- Icosapent --.

Column 43, Line 65, delete "kosapent" and insert -- Icosapent --.

Column 44, Line 21, delete "I. halal," and insert -- I. Jialal, --.

Column 47, Line 48, delete "'omics))," and insert -- 'omics), --.

CERTIFICATE OF CORRECTION (continued)
U.S. Pat. No. 11,887,713 B2

Column 49, Line 25, Table 3, delete "(mmol/)" and insert -- (mmol/l) --.

Column 51, Line 20, delete "(Raj sheker," and insert -- (Rajsheker, --.

Column 55, Line 4, Table 6, delete "ap07042" and insert -- map07042 --.

Column 57, Line 47, delete "lipid lowering" and insert -- lipid-lowering --.

Column 61, Line 16, delete "Simulator)(Shalhoub," and insert -- Simulator) (Shalhoub, --.

Column 64, Line 37, delete "lipid lowering" and insert -- lipid-lowering --.

Column 64, Line 40, delete "mo1.0000000000000773(2021))" and insert -- mol.0000000000000773(2021)) --.

Column 64, Line 41, delete "IL 1β" and insert -- IL1β --.

Column 64, Line 56, delete "lipid lowering" and insert -- lipid-lowering --.

Column 65, Line 3, delete "lipid lowering" and insert -- lipid-lowering --.

Column 65, Line 8, delete "lipid lowering" and insert -- lipid-lowering --.

Column 65, Line 12, delete "lipid lowering" and insert -- lipid-lowering --.

Column 65, Line 31, delete "lipid lowering" and insert -- lipid-lowering --.

Column 65, Line 36, delete "lipid lowering" and insert -- lipid-lowering --.

Column 65, Line 37, delete "lipid lowering" and insert -- lipid-lowering --.

Column 66, Line 5, delete "lipid lowering" and insert -- lipid-lowering --.

Column 66, Line 13, delete "lipid lowering" and insert -- lipid-lowering --.

Column 66, Line 22, delete "lipid lowering" and insert -- lipid-lowering --.

Column 68, Line 1, delete "lipid lowering" and insert -- lipid-lowering --.

Column 68, Line 8, before "lowering" insert -- lipid- --.

Column 68, Line 9, delete "anti-lipid diabetic" and insert -- anti-diabetic --.

Column 68, Line 12, delete "lipid lowering" and insert -- lipid-lowering --.

Column 68, Line 17, delete "Lipid Lowering" and insert -- Lipid-Lowering --.

CERTIFICATE OF CORRECTION (continued)
U.S. Pat. No. 11,887,713 B2

Column 69, Line 7, delete "lipid lowering" and insert -- lipid-lowering --.

Column 69, Line 9, delete "lipid lowering" and insert -- lipid-lowering --.

Column 69, Line 4, Table 12, delete "[0.93,0.99]" and insert -- [0.93, 0.99] --.

Column 69, Line 21, delete "lipid lowering" and insert -- lipid-lowering --.

Column 69, Line 22, delete "lipid lowering" and insert -- lipid-lowering --.

Column 70, Line 7, delete "lipid lowering" and insert -- lipid-lowering --.

Column 70, Line 20, delete "lipid lowering" and insert -- lipid-lowering --.

Column 70, Line 26, Table 12, delete "Lipid Lowering" and insert -- Lipid-Lowering --.

In the Claims

Column 73, Line 37, Claim 5, delete "single-photon emission tomography (SPECT)", and insert -- single-photon emission computed tomography (SPECT) --.